(12) United States Patent
Chene et al.

(10) Patent No.: US 12,263,210 B2
(45) Date of Patent: *Apr. 1, 2025

(54) IMMUNOGENIC COMPOUNDS FOR CANCER THERAPY

(71) Applicant: ENTEROME S.A., Paris (FR)

(72) Inventors: Laurent Chene, Neuville aux Bois (FR); Alban Mathieu, Saint Foy les Lyon (FR); Matthieu Pichaud, Cambridge, MA (US); Francesco Strozzi, Paris (FR)

(73) Assignee: ENTEROME S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/823,117

(22) Filed: Aug. 30, 2022

(65) Prior Publication Data

US 2023/0201322 A1 Jun. 29, 2023

Related U.S. Application Data

(63) Continuation of application No. 16/338,953, filed as application No. PCT/EP2017/075673 on Oct. 9, 2017, now Pat. No. 11,478,537.

(30) Foreign Application Priority Data

Oct. 7, 2016 (EP) .................... 161929484

(51) Int. Cl.
| | | |
|---|---|---|
| *A61K 39/00* | (2006.01) | |
| *A61K 39/385* | (2006.01) | |
| *A61P 35/00* | (2006.01) | |
| *C07K 7/06* | (2006.01) | |

(52) U.S. Cl.
CPC ........ *A61K 39/0011* (2013.01); *A61K 39/385* (2013.01); *A61P 35/00* (2018.01); *C07K 7/06* (2013.01); *A61K 2039/5154* (2013.01); *A61K 2039/6031* (2013.01)

(58) Field of Classification Search
CPC .............. A61K 39/0011; A61K 39/385; A61K 2039/5154; A61K 2039/6031; A61K 2039/55566; A61P 35/00; C07K 7/06
See application file for complete search history.

(56) References Cited

U.S. PATENT DOCUMENTS

| | | |
|---|---|---|
| 2007/0087411 A1 | 4/2007 | Sharma et al. |
| 2008/0166374 A1 | 7/2008 | Debinski et al. |
| 2011/0110955 A1 | 5/2011 | Debinski et al. |
| 2012/0052080 A1 | 3/2012 | Okada |
| 2014/0141044 A1* | 5/2014 | Bhatt ..................... C12Q 1/689 424/234.1 |
| 2018/0078627 A1* | 3/2018 | Zeng ................. A61K 39/4615 |
| 2018/0133339 A1 | 5/2018 | Derouazi et al. |
| 2019/0388532 A1 | 12/2019 | Chene et al. |
| 2020/0025774 A1 | 1/2020 | Chene et al. |
| 2020/0113983 A1 | 4/2020 | Chene et al. |
| 2020/0256877 A1 | 8/2020 | Chene et al. |
| 2021/0106652 A1 | 4/2021 | Chene et al. |
| 2021/0113678 A1 | 4/2021 | Chene et al. |
| 2022/0323561 A1 | 10/2022 | Chene et al. |

FOREIGN PATENT DOCUMENTS

| | | |
|---|---|---|
| CN | 1954217 A | 4/2007 |
| CN | 104774261 A | 7/2015 |
| EP | 1587532 A2 | 10/2005 |
| EP | 2189471 A1 | 5/2010 |
| EP | 3536334 A1 | 9/2019 |
| JP | 2003524016 A | 8/2003 |
| JP | 2006517529 A | 7/2006 |
| JP | 2015518835 A | 7/2015 |
| WO | WO-1995021862 | 8/1995 |
| WO | WO-2001000225 | 1/2001 |
| WO | WO-2001/058479 A1 | 8/2001 |
| WO | WO-2001062776 | 8/2001 |
| WO | WO-2003/092717 A1 | 11/2003 |
| WO | WO-2004031211 | 4/2004 |
| WO | WO-2004067023 A2 | 8/2004 |
| WO | WO-2006034334 A2 | 3/2006 |
| WO | WO-2008073463 A2 | 6/2008 |
| WO | WO-2010/018136 A1 | 2/2010 |
| WO | 2010/129033 A3 | 3/2011 |
| WO | WO-2011140284 A2 | 11/2011 |
| WO | WO-2012027379 A2 | 3/2012 |
| WO | WO-2013135553 A1 | 9/2013 |
| WO | WO-2013142477 A1 | 9/2013 |
| WO | WO-2013148147 A1 | 10/2013 |
| WO | WO-2013173411 A1 | 11/2013 |
| WO | WO-2014088432 A1 | 6/2014 |
| WO | WO-2014089375 A1 | 6/2014 |
| WO | WO-2017203526 A1 | 11/2017 |

(Continued)

OTHER PUBLICATIONS

Tian, et al., Microbiome 2020 vol. 8 Article 51 (Year: 2020).*
Cania, et al., Environmental Microbiome 2019 14:1 (Year: 2019).*
Dill, et al., PNAS 2011 108(44): 17876 (Year: 2011).*
Aglietta, et al., Biol Blood Marrow Transplant 2009 15:326 (Year: 2009).*
Office Action from corresponding U.S. Appl. No. 16/338,953 dated Jul. 20, 2021.
Office Action from corresponding U.S. Appl. No. 16/338,955 dated May 14, 2021.
Office Action from corresponding U.S. Appl. No. 16/338,955 dated Oct. 8, 2021.

(Continued)

*Primary Examiner* — Karen A. Canella
*Assistant Examiner* — Sydney Van Druff
(74) *Attorney, Agent, or Firm* — Harness Dickey & Pierce P.L.C.

(57) ABSTRACT

The invention relates to an immunogenic compound comprising an antigenic peptide having amino acid similarity with a tumor antigen, which antigenic peptide is selected in the group consisting of sequences described in the specification.

19 Claims, 3 Drawing Sheets

Specification includes a Sequence Listing.

(56) References Cited

FOREIGN PATENT DOCUMENTS

| WO | WO-2019072871 A2 | 4/2019 |
|---|---|---|
| WO | WO-2021074389 A1 | 4/2021 |
| WO | WO-2021094562 A2 | 5/2021 |

OTHER PUBLICATIONS

Office Action from corresponding U.S. Appl. No. 16/338,955 dated May 20, 2022.
Office Action issued in corresponding CN Appln. No. 201780074779.3 dated Oct. 14, 2022.
Search Report issued in corresponding CN Appln. No. 201780074779.3 dated Oct. 8, 2022.
Office action issued in corresponding U.S. Appl. No. 16/338,954 dated Mar. 3, 2022.
Restriction requirement issued in corresponding U.S. Appl. No. 16/338,954 dated Jun. 24, 2022.
Notice of Allowance issued in corresponding U.S. Appl. No. 16/338,954 dated Dec. 1, 2022.
Restriction Requirement issued in corresponding U.S. Appl. No. 16/338,953 dated Apr. 5, 2021.
Notice of Allowance issued in corresponding U.S. Appl. No. 16/338,953 dated Mar. 2, 2022.
Notice of Allowance issued in corresponding U.S. Appl. No. 16/338,953 dated Apr. 5, 2022.
Notice of Allowance issued in corresponding U.S. Appl. No. 16/338,953 dated Jun. 15, 2022.
Restriction Requirement issued in corresponding U.S. Appl. No. 16/338,955 dated Mar. 9, 2021.
Notice of Allowance issued in corresponding U.S. Appl. No. 16/338,955 dated Aug. 8, 2022.
Notice of Allowance issued in corresponding U.S. Appl. No. 16/338,955 dated Aug. 31, 2022.
Office Action issued in corresponding RU Appln. No. 2020135927 dated Nov. 3, 2022.
Baryšnikov A. Û, "The Interation of Tumor and Immune System of the Organism," Praktičeskaâ Onkologiâ[Practical Oncology] 4(3), p. 127-130 (2003).
Dhanik, et al. "In-silico discovery of cancer-specific peptide-HLA complexes for targeted therapy," BCM Bioinformatics 17:286 (2016), 14 pages.
Xiao et al., "Peptide-Based Treatment: A Promising Cancer Therapy," Journal of Immunology Research, Vo. 2015, Article ID 761820, 13 pages.
Fichtner-Feigl et al., "IL-13 signaling through the IL-13alpha2 receptor is involved in induction of TGF-beta1 production and fibrosis," Nature Medicine, 12(1): 99-106 (2006).
Hirsova et al., "Emerging Roles of T Cells in the Pathogenesis of Nonalcoholic Steatohepatitis and Hepatocellular Carcinoma," Front. Endocrinol. 12(760860): 1-14 (2021).
Office action issued in U.S. Appl. No. 17/043,197 dated Jun. 1, 2023.
Dosset et al. (2012). Universal cancer peptide-based therapeutic vaccine breaks tolerance against telomerase and eradicates established tumor, Clinical Cancer Res, 18(22): 6284-95.
Flugel and Fischer (2014). Simian Virus Tumor Antigen: A virus-specific and preexisting cell protein. Journal of the National Cancer Institute, 55(4): 899-901.
Restriction Requirement issued in U.S. Appl. No. 16/753,657 dated Aug. 9, 2023.
Office Action issued in U.S. Appl. No. 17/929,063 dated Nov. 9, 2023.
Office Action issued in Chinese Application No. CN201880065726.X dated Jan. 20, 2023.
Search Report issued in Chinese Application No. 201880065726.X dated Jan. 17, 2023.

Office Action from U.S. Appl. No. 17/043,197 dated Jan. 16, 2024.
Attallah et al. (2016) Interferon-gamma is associated with hepatic dysfunction in fibrosis, cirrhosis, and hepatocellular carcinoma. J Immunoassay Immunochem, 37(6): 597-610.
Office Action from U.S. Appl. No. 16/753,657 dated Jan. 19, 2024.
Baylot, V., et al., "Chapter 13: TCTP Has a Crucial Role in the Different Stages of Prostate Cancer Malignant Progression," Springer International Publishing AG, 2017, p. 255-261.
Badri, H., et al., "Optimization of radiation dosing schedules for proneural glioblastoma," J. Math. Biol., 72: 1301-1336 (2016).
Office Action from corresponding Russian Application No. 2020135927 dated Jun. 16, 2023.
Accession No. C2MB65, version 17, Heavy metal efflux pump, CzcA family, Database Uniprot [online], (2016).
Accession No. F4KLC2, version 28, Acriflavin resistance protein, Database Uniprot [online] (2016).
Andrews, A., et al., "IL-13 receptor alpha 2: A regulator of IL-13 and IL-4 signal transduction in primary human fibroblasts," Journal of Allergy and Clinical Immuno., 118(4): 858-865, (2006).
Buhrman, J.D., and Slansky, J.E., "Improving T cell responses to modified peptides in tumor vaccines," Immunol Res 55: 34-47 (2013).
Carter, J., "Conjugation of Peptides to Carrier Proteins via Glutaraldehyde," The Protein Protocols Handbook, 117: 679-687 (1996).
Cuzick, J., et al., "Tamoxifen for prevention of breast cancer: extended long-term follow-up of the IBIS-I breast cancer prevention trial," Lancet Oncol, 16(1): 67-75 (2015).
Database UniParc (Online) Apr. 6, 2016 (Apr. 6, 2016), XP002777564, Database accession No. UPI0008B57C7B abstract.
Database UniParc [Online] Jun. 4, 2016 (Jun. 4, 2016), XP002777565, Database accession No. UPI000ADDED27 abstract.
Database UniParc [Online] Apr. 6, 2016 (Apr. 6, 2016), XP002777566, Database accession No. UPI000AFC0494 abstract.
Database UniParc [Online] Nov. 6, 2017 (Nov. 6, 2017), XP002777567, Database accession No. UPI000B513427 abstract.
Database UniParc XP-002777564 (2016).
Database UniParc XP-002777565 (2016).
Database UniParc XP-002777566 (2016).
Database UniParc XP-002777567 (2017).
Database UniParc XP-002790579 (2013).
Database UniParc XP-002794914 (2017).
Eguchi, J., et al., "Identification of Interleukin-13 Receptor x2 Peptide Analogues Capable of Inducing Improved Antiglioma CTL Responses," Cancer Res. 66(11): 5883-5891 (2006).
Fikes, John, "The Rational Design of T-Cell Epitopes With Enhanced Immunogenicity," Handbook of Cancer Vaccines, Humana Press, pp. 11-17 (2004).
Huarte, E., et al., "Enhancing Immunogenicity of a CTL Epitope from Carcinoembryonic Antigen by Selective Amino Acid Replacements", Clinical Cancer Research, 8: 2336-2344 (2002).
International Search Report and Written Opinion issued in PCT/EP2017/075673, Apr. 30, 2018, 17 pgs.
International Search Report and Written Opinion issued in PCT/EP2017/075676, Jun. 15, 2018, 18 pgs.
International Search Report and Written Opinion issued in PCT/EP2017/075683, Apr. 4, 2018, 20 pages.
International Search Report from corresponding PCT Application No. PCT/EP2020/079226 dated Mar. 19, 2021.
International Search Report from PCT Application No. PCT/EP2018/077515 dated May 6, 2019.
International Search Report from PCT Application No. PCT/EP2019/059319 dated Dec. 17, 2019.
International Search Report from PCT Application No. PCT/EP2019/059329 dated Oct. 28, 2019.
Ma, W., et al., "PLGA nanoparticle-mediated delivery of tumor antigenic peptides elicits effective immune responses," International Journal of Nanomedicine, 7: 1475-1487 (2012).
Nakashima, Hideyuki et al., "A Novel Combination Immunotherapy for Cancer by IL-13R α2 -Targeted DNA Vaccine and Immunotoxin in Murine Tumor Models," The Journal of Immunology, 2011, 187(10): 4935-4946.
Nakashima, Hideyuki et al., "IL-13 receptor-directed cancer vaccines and immunotherapy," Immunotherapy, 2012, 4(4): 443-451.

(56) References Cited

OTHER PUBLICATIONS

Noedominguez-Romero, A., et al., "Variable epitope library carrying heavily mutated survivin-derived CTL epitope variants as a new class of efficient vaccine immunogen tested in a mouse model of breat cancer," Human Vaccines & Immunotherapeutics, 10(11): 3201-3213 (2014).

Papewalis, C., et al., "Chromogranin A as potential target for immunotherapy of malignant pheochromocytoma," Molecular and Cellular Endocrinology, 335: 569-77 (2011).

Parkhurst et al., "Improved Induction of Melanoma-Reactive CTL with Peptides from the Melanoma Antigen gp100 Modified at HLA-A*0201-Binding Residues," The American Association of Immunologists, 1996, 157(6): 2539-2548.

Rodeberg, David et al., "Recognition of Six-Transmembrane Epithelial Antigen of the Prostate—Expressing Tumor Cells by Peptide Antigen—Induced Cytotoxic T Lymphocytes," Clinical Cancer Research, 2005, 11(12): 4545-4552.

Scardino, A., et al., "HER-2/neu and hTERT Cryptic Epitopes as Novel Targets for Broad Spectrum Tumor Immunotherapy," The Journal of Immunology, 168(11): 5900-5906 (2000).

Shah, R., et al., "Pathogenesis, prevention, diagnosis and treatment of breast cancer," World J Clin Oncol, 5(3): 283-298 (2014).

Tourdot, Sophie et al., "A general strategy to enhance immunogenicity of low-affinity HLA-A2.1-associated peptides: implication in the identification of cryptic tumor epitopes," European Journal of Immunology, 2000, 30(1): 3411-3421.

Vertuani, Simona et al., "Improved Immunogenicity of an Immunodominant Epitope of the Her-2/neu Protooncogene by Alterations of MHC Contact Residues," Journal of Immunology, 2004, 172(6): 3501-3508.

Written Opinion from corresponding PCT Application No. PCT/EP2020/079226 dated Mar. 19, 2021.

Written Opinion from PCT Application No. PCT/EP2018/077515 dated May 6, 2019.

Written Opinion from PCT Application No. PCT/EP2019/059319 dated Dec. 17, 2019.

Written Opinion from PCT Application No. PCT/EP2019/059329 dated Oct. 28, 2019.

Yokomine, K., et al., "The forkhead box M1 transcription factor as a candidate of target for anti-cancer immunotherapy," Int. J. Cancer, 126: 2153-2163 (2010).

Office Action from corresponding U.S. Appl. No. 16/338,953 dated Nov. 23, 2021.

Office Action from Japanese Application No. 2023-191203 dated Nov. 26, 2024.

\* cited by examiner

SEQUENCE LISTING

```
Sequence total quantity: 144
SEQ ID NO: 1             moltype = AA  length = 9
FEATURE                  Location/Qualifiers
REGION                   1..9
                         note = peptide
source                   1..9
                         mol_type = protein
                         organism = synthetic construct
SEQUENCE: 1
SLAGTITGV                                                                 9

SEQ ID NO: 2             moltype = AA  length = 9
FEATURE                  Location/Qualifiers
REGION                   1..9
                         note = peptide
source                   1..9
                         mol_type = protein
                         organism = synthetic construct
SEQUENCE: 2
LLMKLADLV                                                                 9

SEQ ID NO: 3             moltype = AA  length = 9
FEATURE                  Location/Qualifiers
REGION                   1..9
                         note = peptide
source                   1..9
                         mol_type = protein
                         organism = synthetic construct
SEQUENCE: 3
LLYKIADLV                                                                 9

SEQ ID NO: 4             moltype = AA  length = 10
FEATURE                  Location/Qualifiers
REGION                   1..10
                         note = peptide
source                   1..10
                         mol_type = protein
```

```
                                        organism = synthetic construct
SEQUENCE: 4
SLALSVILRV                                                                              10

SEQ ID NO: 5           moltype = AA   length = 10
FEATURE                Location/Qualifiers
REGION                 1..10
                       note = peptide
source                 1..10
                       mol_type = protein
                       organism = synthetic construct
SEQUENCE: 5
SLAVSVILRA                                                                              10

SEQ ID NO: 6           moltype = AA   length = 9
FEATURE                Location/Qualifiers
REGION                 1..9
                       note = peptide
source                 1..9
                       mol_type = protein
                       organism = synthetic construct
SEQUENCE: 6
KLLDAVISL                                                                                9

SEQ ID NO: 7           moltype = AA   length = 9
FEATURE                Location/Qualifiers
REGION                 1..9
                       note = peptide
source                 1..9
                       mol_type = protein
                       organism = synthetic construct
SEQUENCE: 7
KLLDALLSL                                                                                9

SEQ ID NO: 8           moltype = AA   length = 9
FEATURE                Location/Qualifiers
REGION                 1..9
                       note = peptide
source                 1..9
                       mol_type = protein
                       organism = synthetic construct
SEQUENCE: 8
KMLDALIDL                                                                                9

SEQ ID NO: 9           moltype = AA   length = 9
FEATURE                Location/Qualifiers
REGION                 1..9
                       note = peptide
source                 1..9
                       mol_type = protein
                       organism = synthetic construct
SEQUENCE: 9
KILDSLISL                                                                                9

SEQ ID NO: 10          moltype = AA   length = 9
FEATURE                Location/Qualifiers
REGION                 1..9
                       note = peptide
source                 1..9
                       mol_type = protein
                       organism = synthetic construct
SEQUENCE: 10
KFLDALIGV                                                                                9

SEQ ID NO: 11          moltype = AA   length = 9
FEATURE                Location/Qualifiers
REGION                 1..9
                       note = peptide
source                 1..9
                       mol_type = protein
                       organism = synthetic construct
SEQUENCE: 11
KFLDSLISV                                                                                9

SEQ ID NO: 12          moltype = AA   length = 9
FEATURE                Location/Qualifiers
REGION                 1..9
                       note = peptide
source                 1..9
```

```
                            mol_type = protein
                            organism = synthetic construct
SEQUENCE: 12
GVLAGVALV                                                                    9

SEQ ID NO: 13               moltype = AA  length = 9
FEATURE                     Location/Qualifiers
REGION                      1..9
                            note = peptide
source                      1..9
                            mol_type = protein
                            organism = synthetic construct
SEQUENCE: 13
GMLVGVALI                                                                    9

SEQ ID NO: 14               moltype = AA  length = 9
FEATURE                     Location/Qualifiers
REGION                      1..9
                            note = peptide
source                      1..9
                            mol_type = protein
                            organism = synthetic construct
SEQUENCE: 14
GLLMGVALI                                                                    9

SEQ ID NO: 15               moltype = AA  length = 9
FEATURE                     Location/Qualifiers
REGION                      1..9
                            note = peptide
source                      1..9
                            mol_type = protein
                            organism = synthetic construct
SEQUENCE: 15
GVLVGLALV                                                                    9

SEQ ID NO: 16               moltype = AA  length = 9
FEATURE                     Location/Qualifiers
REGION                      1..9
                            note = peptide
source                      1..9
                            mol_type = protein
                            organism = synthetic construct
SEQUENCE: 16
GVLAGIALI                                                                    9

SEQ ID NO: 17               moltype = AA  length = 9
FEATURE                     Location/Qualifiers
REGION                      1..9
                            note = peptide
source                      1..9
                            mol_type = protein
                            organism = synthetic construct
SEQUENCE: 17
GILVGVALV                                                                    9

SEQ ID NO: 18               moltype = AA  length = 9
FEATURE                     Location/Qualifiers
REGION                      1..9
                            note = peptide
source                      1..9
                            mol_type = protein
                            organism = synthetic construct
SEQUENCE: 18
GLLIGVALI                                                                    9

SEQ ID NO: 19               moltype = AA  length = 9
FEATURE                     Location/Qualifiers
REGION                      1..9
                            note = peptide
source                      1..9
                            mol_type = protein
                            organism = synthetic construct
SEQUENCE: 19
GVLLGVALV                                                                    9

SEQ ID NO: 20               moltype = AA  length = 9
FEATURE                     Location/Qualifiers
REGION                      1..9
                            note = peptide
```

```
source                    1..9
                          mol_type = protein
                          organism = synthetic construct
SEQUENCE: 20
GVLTGIALI                                                                       9

SEQ ID NO: 21             moltype = AA  length = 9
FEATURE                   Location/Qualifiers
REGION                    1..9
                          note = peptide
source                    1..9
                          mol_type = protein
                          organism = synthetic construct
SEQUENCE: 21
GILVGLALI                                                                       9

SEQ ID NO: 22             moltype = AA  length = 9
FEATURE                   Location/Qualifiers
REGION                    1..9
                          note = peptide
source                    1..9
                          mol_type = protein
                          organism = synthetic construct
SEQUENCE: 22
GVIVGVALV                                                                       9

SEQ ID NO: 23             moltype = AA  length = 9
FEATURE                   Location/Qualifiers
REGION                    1..9
                          note = peptide
source                    1..9
                          mol_type = protein
                          organism = synthetic construct
SEQUENCE: 23
GVFVGLALI                                                                       9

SEQ ID NO: 24             moltype = AA  length = 9
FEATURE                   Location/Qualifiers
REGION                    1..9
                          note = peptide
source                    1..9
                          mol_type = protein
                          organism = synthetic construct
SEQUENCE: 24
GVLIGVALV                                                                       9

SEQ ID NO: 25             moltype = AA  length = 9
FEATURE                   Location/Qualifiers
REGION                    1..9
                          note = peptide
source                    1..9
                          mol_type = protein
                          organism = synthetic construct
SEQUENCE: 25
YLFGHSWYK                                                                       9

SEQ ID NO: 26             moltype = AA  length = 9
FEATURE                   Location/Qualifiers
REGION                    1..9
                          note = peptide
source                    1..9
                          mol_type = protein
                          organism = synthetic construct
SEQUENCE: 26
TMNGKSSPV                                                                       9

SEQ ID NO: 27             moltype = AA  length = 9
FEATURE                   Location/Qualifiers
REGION                    1..9
                          note = peptide
source                    1..9
                          mol_type = protein
                          organism = synthetic construct
SEQUENCE: 27
FMAEDETLL                                                                       9

SEQ ID NO: 28             moltype = AA  length = 9
FEATURE                   Location/Qualifiers
REGION                    1..9
```

```
                        note = peptide
source                  1..9
                        mol_type = protein
                        organism = synthetic construct
SEQUENCE: 28
ITSDVPFSV                                                                       9

SEQ ID NO: 29           moltype = AA  length = 9
FEATURE                 Location/Qualifiers
REGION                  1..9
                        note = peptide
source                  1..9
                        mol_type = protein
                        organism = synthetic construct
SEQUENCE: 29
IMSAVIGIL                                                                       9

SEQ ID NO: 30           moltype = AA  length = 9
FEATURE                 Location/Qualifiers
REGION                  1..9
                        note = peptide
source                  1..9
                        mol_type = protein
                        organism = synthetic construct
SEQUENCE: 30
ILSAVIGIL                                                                       9

SEQ ID NO: 31           moltype = AA  length = 9
FEATURE                 Location/Qualifiers
REGION                  1..9
                        note = peptide
source                  1..9
                        mol_type = protein
                        organism = synthetic construct
SEQUENCE: 31
ILSAVVGVL                                                                       9

SEQ ID NO: 32           moltype = AA  length = 9
FEATURE                 Location/Qualifiers
REGION                  1..9
                        note = peptide
source                  1..9
                        mol_type = protein
                        organism = synthetic construct
SEQUENCE: 32
IMSAVVGIL                                                                       9

SEQ ID NO: 33           moltype = AA  length = 9
FEATURE                 Location/Qualifiers
REGION                  1..9
                        note = peptide
source                  1..9
                        mol_type = protein
                        organism = synthetic construct
SEQUENCE: 33
FISAVVGVL                                                                       9

SEQ ID NO: 34           moltype = AA  length = 9
FEATURE                 Location/Qualifiers
REGION                  1..9
                        note = peptide
source                  1..9
                        mol_type = protein
                        organism = synthetic construct
SEQUENCE: 34
ILSAVVGIL                                                                       9

SEQ ID NO: 35           moltype = AA  length = 9
FEATURE                 Location/Qualifiers
REGION                  1..9
                        note = peptide
source                  1..9
                        mol_type = protein
                        organism = synthetic construct
SEQUENCE: 35
IISAVIGIV                                                                       9

SEQ ID NO: 36           moltype = AA  length = 9
FEATURE                 Location/Qualifiers
```

```
                              -continued

REGION                  1..9
                        note = peptide
source                  1..9
                        mol_type = protein
                        organism = synthetic construct
SEQUENCE: 36
IISAIVGLL                                                                    9

SEQ ID NO: 37           moltype = AA  length = 9
FEATURE                 Location/Qualifiers
REGION                  1..9
                        note = peptide
source                  1..9
                        mol_type = protein
                        organism = synthetic construct
SEQUENCE: 37
IISAIVGIV                                                                    9

SEQ ID NO: 38           moltype = AA  length = 9
FEATURE                 Location/Qualifiers
REGION                  1..9
                        note = peptide
source                  1..9
                        mol_type = protein
                        organism = synthetic construct
SEQUENCE: 38
IISAVVGVV                                                                    9

SEQ ID NO: 39           moltype = AA  length = 9
FEATURE                 Location/Qualifiers
REGION                  1..9
                        note = peptide
source                  1..9
                        mol_type = protein
                        organism = synthetic construct
SEQUENCE: 39
IISAVVGIV                                                                    9

SEQ ID NO: 40           moltype = AA  length = 9
FEATURE                 Location/Qualifiers
REGION                  1..9
                        note = peptide
source                  1..9
                        mol_type = protein
                        organism = synthetic construct
SEQUENCE: 40
LISAVVGLL                                                                    9

SEQ ID NO: 41           moltype = AA  length = 9
FEATURE                 Location/Qualifiers
REGION                  1..9
                        note = peptide
source                  1..9
                        mol_type = protein
                        organism = synthetic construct
SEQUENCE: 41
ILYGGAYSL                                                                    9

SEQ ID NO: 42           moltype = AA  length = 9
FEATURE                 Location/Qualifiers
REGION                  1..9
                        note = peptide
source                  1..9
                        mol_type = protein
                        organism = synthetic construct
SEQUENCE: 42
KLYGSLAFL                                                                    9

SEQ ID NO: 43           moltype = AA  length = 9
FEATURE                 Location/Qualifiers
REGION                  1..9
                        note = peptide
source                  1..9
                        mol_type = protein
                        organism = synthetic construct
SEQUENCE: 43
KIFGTLAFM                                                                    9

SEQ ID NO: 44           moltype = AA  length = 9
```

```
FEATURE                 Location/Qualifiers
REGION                  1..9
                        note = peptide
source                  1..9
                        mol_type = protein
                        organism = synthetic construct
SEQUENCE: 44
PLADIISAV                                                                      9

SEQ ID NO: 45           moltype = AA  length = 9
FEATURE                 Location/Qualifiers
REGION                  1..9
                        note = peptide
source                  1..9
                        mol_type = protein
                        organism = synthetic construct
SEQUENCE: 45
PLASIFSAV                                                                      9

SEQ ID NO: 46           moltype = AA  length = 9
FEATURE                 Location/Qualifiers
REGION                  1..9
                        note = peptide
source                  1..9
                        mol_type = protein
                        organism = synthetic construct
SEQUENCE: 46
PLSSILSAV                                                                      9

SEQ ID NO: 47           moltype = AA  length = 9
FEATURE                 Location/Qualifiers
REGION                  1..9
                        note = peptide
source                  1..9
                        mol_type = protein
                        organism = synthetic construct
SEQUENCE: 47
RLLEETDLV                                                                      9

SEQ ID NO: 48           moltype = AA  length = 9
FEATURE                 Location/Qualifiers
REGION                  1..9
                        note = peptide
source                  1..9
                        mol_type = protein
                        organism = synthetic construct
SEQUENCE: 48
TLNDITGYL                                                                      9

SEQ ID NO: 49           moltype = AA  length = 9
FEATURE                 Location/Qualifiers
REGION                  1..9
                        note = peptide
source                  1..9
                        mol_type = protein
                        organism = synthetic construct
SEQUENCE: 49
TLEEITNFL                                                                      9

SEQ ID NO: 50           moltype = AA  length = 9
FEATURE                 Location/Qualifiers
REGION                  1..9
                        note = peptide
source                  1..9
                        mol_type = protein
                        organism = synthetic construct
SEQUENCE: 50
TVDEITGYL                                                                      9

SEQ ID NO: 51           moltype = AA  length = 9
FEATURE                 Location/Qualifiers
REGION                  1..9
                        note = peptide
source                  1..9
                        mol_type = protein
                        organism = synthetic construct
SEQUENCE: 51
VMLGVVFGV                                                                      9
```

```
SEQ ID NO: 52           moltype = AA  length = 9
FEATURE                 Location/Qualifiers
REGION                  1..9
                        note = peptide
source                  1..9
                        mol_type = protein
                        organism = synthetic construct
SEQUENCE: 52
VLLGVVFGV                                                                9

SEQ ID NO: 53           moltype = AA  length = 9
FEATURE                 Location/Qualifiers
REGION                  1..9
                        note = peptide
source                  1..9
                        mol_type = protein
                        organism = synthetic construct
SEQUENCE: 53
MVLGVVFGV                                                                9

SEQ ID NO: 54           moltype = AA  length = 9
FEATURE                 Location/Qualifiers
REGION                  1..9
                        note = peptide
source                  1..9
                        mol_type = protein
                        organism = synthetic construct
SEQUENCE: 54
VMLGIVFGI                                                                9

SEQ ID NO: 55           moltype = AA  length = 9
FEATURE                 Location/Qualifiers
REGION                  1..9
                        note = peptide
source                  1..9
                        mol_type = protein
                        organism = synthetic construct
SEQUENCE: 55
VMLGVVFGI                                                                9

SEQ ID NO: 56           moltype = AA  length = 9
FEATURE                 Location/Qualifiers
REGION                  1..9
                        note = peptide
source                  1..9
                        mol_type = protein
                        organism = synthetic construct
SEQUENCE: 56
ILLGVVFGI                                                                9

SEQ ID NO: 57           moltype = AA  length = 9
FEATURE                 Location/Qualifiers
REGION                  1..9
                        note = peptide
source                  1..9
                        mol_type = protein
                        organism = synthetic construct
SEQUENCE: 57
VLLGVIFGI                                                                9

SEQ ID NO: 58           moltype = AA  length = 9
FEATURE                 Location/Qualifiers
REGION                  1..9
                        note = peptide
source                  1..9
                        mol_type = protein
                        organism = synthetic construct
SEQUENCE: 58
VLFGVVFGI                                                                9

SEQ ID NO: 59           moltype = AA  length = 9
FEATURE                 Location/Qualifiers
REGION                  1..9
                        note = peptide
source                  1..9
                        mol_type = protein
                        organism = synthetic construct
SEQUENCE: 59
IVLGVVFGV                                                                9
```

```
SEQ ID NO: 60            moltype = AA  length = 9
FEATURE                  Location/Qualifiers
REGION                   1..9
                         note = peptide
source                   1..9
                         mol_type = protein
                         organism = synthetic construct
SEQUENCE: 60
VVLGVLFGV                                                                9

SEQ ID NO: 61            moltype = AA  length = 9
FEATURE                  Location/Qualifiers
REGION                   1..9
                         note = peptide
source                   1..9
                         mol_type = protein
                         organism = synthetic construct
SEQUENCE: 61
VVLGVMFGV                                                                9

SEQ ID NO: 62            moltype = AA  length = 9
FEATURE                  Location/Qualifiers
REGION                   1..9
                         note = peptide
source                   1..9
                         mol_type = protein
                         organism = synthetic construct
SEQUENCE: 62
VVLGVIFGV                                                                9

SEQ ID NO: 63            moltype = AA  length = 9
FEATURE                  Location/Qualifiers
REGION                   1..9
                         note = peptide
source                   1..9
                         mol_type = protein
                         organism = synthetic construct
SEQUENCE: 63
VVLGAVFGV                                                                9

SEQ ID NO: 64            moltype = AA  length = 9
FEATURE                  Location/Qualifiers
REGION                   1..9
                         note = peptide
source                   1..9
                         mol_type = protein
                         organism = synthetic construct
SEQUENCE: 64
VVLGLVFGV                                                                9

SEQ ID NO: 65            moltype = AA  length = 9
FEATURE                  Location/Qualifiers
REGION                   1..9
                         note = peptide
source                   1..9
                         mol_type = protein
                         organism = synthetic construct
SEQUENCE: 65
VVIGVVFGV                                                                9

SEQ ID NO: 66            moltype = AA  length = 9
FEATURE                  Location/Qualifiers
REGION                   1..9
                         note = peptide
source                   1..9
                         mol_type = protein
                         organism = synthetic construct
SEQUENCE: 66
VVLGIVFGV                                                                9

SEQ ID NO: 67            moltype = AA  length = 9
FEATURE                  Location/Qualifiers
REGION                   1..9
                         note = peptide
source                   1..9
                         mol_type = protein
                         organism = synthetic construct
SEQUENCE: 67
```

```
TVLGVVFGV                                                                          9

SEQ ID NO: 68          moltype = AA   length = 9
FEATURE                Location/Qualifiers
REGION                 1..9
                       note = peptide
source                 1..9
                       mol_type = protein
                       organism = synthetic construct
SEQUENCE: 68
VVLGVVFGV                                                                          9

SEQ ID NO: 69          moltype = AA   length = 9
FEATURE                Location/Qualifiers
REGION                 1..9
                       note = peptide
source                 1..9
                       mol_type = protein
                       organism = synthetic construct
SEQUENCE: 69
AILGVVFGI                                                                          9

SEQ ID NO: 70          moltype = AA   length = 9
FEATURE                Location/Qualifiers
REGION                 1..9
                       note = peptide
source                 1..9
                       mol_type = protein
                       organism = synthetic construct
SEQUENCE: 70
AVLGVMFGI                                                                          9

SEQ ID NO: 71          moltype = AA   length = 9
FEATURE                Location/Qualifiers
REGION                 1..9
                       note = peptide
source                 1..9
                       mol_type = protein
                       organism = synthetic construct
SEQUENCE: 71
FLPFGFILV                                                                          9

SEQ ID NO: 72          moltype = AA   length = 9
FEATURE                Location/Qualifiers
REGION                 1..9
                       note = peptide
source                 1..9
                       mol_type = protein
                       organism = synthetic construct
SEQUENCE: 72
KMLHYVIKV                                                                          9

SEQ ID NO: 73          moltype = AA   length = 9
FEATURE                Location/Qualifiers
REGION                 1..9
                       note = peptide
source                 1..9
                       mol_type = protein
                       organism = synthetic construct
SEQUENCE: 73
EMNPIGHLY                                                                          9

SEQ ID NO: 74          moltype = AA   length = 9
FEATURE                Location/Qualifiers
REGION                 1..9
                       note = peptide
source                 1..9
                       mol_type = protein
                       organism = synthetic construct
SEQUENCE: 74
RVDPIGNLY                                                                          9

SEQ ID NO: 75          moltype = AA   length = 9
FEATURE                Location/Qualifiers
REGION                 1..9
                       note = peptide
source                 1..9
                       mol_type = protein
                       organism = synthetic construct
```

```
SEQUENCE: 75
VTELVNFLL                                                                      9

SEQ ID NO: 76           moltype = AA   length = 9
FEATURE                 Location/Qualifiers
REGION                  1..9
                        note = peptide
source                  1..9
                        mol_type = protein
                        organism = synthetic construct
SEQUENCE: 76
HVDPATNTY                                                                      9

SEQ ID NO: 77           moltype = AA   length = 9
FEATURE                 Location/Qualifiers
REGION                  1..9
                        note = peptide
source                  1..9
                        mol_type = protein
                        organism = synthetic construct
SEQUENCE: 77
KLVEWLAML                                                                      9

SEQ ID NO: 78           moltype = AA   length = 9
FEATURE                 Location/Qualifiers
REGION                  1..9
                        note = peptide
source                  1..9
                        mol_type = protein
                        organism = synthetic construct
SEQUENCE: 78
SLSYALLSL                                                                      9

SEQ ID NO: 79           moltype = AA   length = 9
FEATURE                 Location/Qualifiers
REGION                  1..9
                        note = peptide
source                  1..9
                        mol_type = protein
                        organism = synthetic construct
SEQUENCE: 79
SISHTLLSL                                                                      9

SEQ ID NO: 80           moltype = AA   length = 9
FEATURE                 Location/Qualifiers
REGION                  1..9
                        note = peptide
source                  1..9
                        mol_type = protein
                        organism = synthetic construct
SEQUENCE: 80
VSSFFSYVF                                                                      9

SEQ ID NO: 81           moltype = AA   length = 9
FEATURE                 Location/Qualifiers
REGION                  1..9
                        note = peptide
source                  1..9
                        mol_type = protein
                        organism = synthetic construct
SEQUENCE: 81
ALNDVEEKV                                                                      9

SEQ ID NO: 82           moltype = AA   length = 9
FEATURE                 Location/Qualifiers
REGION                  1..9
                        note = peptide
source                  1..9
                        mol_type = protein
                        organism = synthetic construct
SEQUENCE: 82
ALSDVEDRV                                                                      9

SEQ ID NO: 83           moltype = AA   length = 9
FEATURE                 Location/Qualifiers
REGION                  1..9
                        note = peptide
source                  1..9
                        mol_type = protein
```

```
                              -continued organism = synthetic construct
SEQUENCE: 83
ALSDAEERV                                                             9

SEQ ID NO: 84         moltype = AA  length = 9
FEATURE               Location/Qualifiers
REGION                1..9
                      note = peptide
source                1..9
                      mol_type = protein
                      organism = synthetic construct
SEQUENCE: 84
ATSTLMLVF                                                             9

SEQ ID NO: 85         moltype = AA  length = 9
FEATURE               Location/Qualifiers
REGION                1..9
                      note = peptide
source                1..9
                      mol_type = protein
                      organism = synthetic construct
SEQUENCE: 85
TTSTLYLVF                                                             9

SEQ ID NO: 86         moltype = AA  length = 9
FEATURE               Location/Qualifiers
REGION                1..9
                      note = peptide
source                1..9
                      mol_type = protein
                      organism = synthetic construct
SEQUENCE: 86
PLFESVISK                                                             9

SEQ ID NO: 87         moltype = AA  length = 9
FEATURE               Location/Qualifiers
REGION                1..9
                      note = peptide
source                1..9
                      mol_type = protein
                      organism = synthetic construct
SEQUENCE: 87
PLLETTISK                                                             9

SEQ ID NO: 88         moltype = AA  length = 9
FEATURE               Location/Qualifiers
REGION                1..9
                      note = peptide
source                1..9
                      mol_type = protein
                      organism = synthetic construct
SEQUENCE: 88
ILTAILGVL                                                             9

SEQ ID NO: 89         moltype = AA  length = 9
FEATURE               Location/Qualifiers
REGION                1..9
                      note = peptide
source                1..9
                      mol_type = protein
                      organism = synthetic construct
SEQUENCE: 89
ILTVILGVV                                                             9

SEQ ID NO: 90         moltype = AA  length = 9
FEATURE               Location/Qualifiers
REGION                1..9
                      note = peptide
source                1..9
                      mol_type = protein
                      organism = synthetic construct
SEQUENCE: 90
ALFAVTSAV                                                             9

SEQ ID NO: 91         moltype = AA  length = 9
FEATURE               Location/Qualifiers
REGION                1..9
                      note = peptide
source                1..9
```

```
                        mol_type = protein
                        organism = synthetic construct
SEQUENCE: 91
ALFALTSAA                                                                        9

SEQ ID NO: 92           moltype = AA   length = 9
FEATURE                 Location/Qualifiers
REGION                  1..9
                        note = peptide
source                  1..9
                        mol_type = protein
                        organism = synthetic construct
SEQUENCE: 92
SLPPDVQEV                                                                        9

SEQ ID NO: 93           moltype = AA   length = 9
FEATURE                 Location/Qualifiers
REGION                  1..9
                        note = peptide
source                  1..9
                        mol_type = protein
                        organism = synthetic construct
SEQUENCE: 93
SLPPDVQQV                                                                        9

SEQ ID NO: 94           moltype = AA   length = 9
FEATURE                 Location/Qualifiers
REGION                  1..9
                        note = peptide
source                  1..9
                        mol_type = protein
                        organism = synthetic construct
SEQUENCE: 94
VAMPFATPV                                                                        9

SEQ ID NO: 95           moltype = AA   length = 9
FEATURE                 Location/Qualifiers
REGION                  1..9
                        note = peptide
source                  1..9
                        mol_type = protein
                        organism = synthetic construct
SEQUENCE: 95
ALDVYSALL                                                                        9

SEQ ID NO: 96           moltype = AA   length = 9
FEATURE                 Location/Qualifiers
REGION                  1..9
                        note = peptide
source                  1..9
                        mol_type = protein
                        organism = synthetic construct
SEQUENCE: 96
ALDMYNALL                                                                        9

SEQ ID NO: 97           moltype = AA   length = 9
FEATURE                 Location/Qualifiers
REGION                  1..9
                        note = peptide
source                  1..9
                        mol_type = protein
                        organism = synthetic construct
SEQUENCE: 97
ALDIYNSLL                                                                        9

SEQ ID NO: 98           moltype = AA   length = 9
FEATURE                 Location/Qualifiers
REGION                  1..9
                        note = peptide
source                  1..9
                        mol_type = protein
                        organism = synthetic construct
SEQUENCE: 98
FLFFLFFFL                                                                        9

SEQ ID NO: 99           moltype = AA   length = 9
FEATURE                 Location/Qualifiers
REGION                  1..9
                        note = peptide
```

```
source                      1..9
                            mol_type = protein
                            organism = synthetic construct
SEQUENCE: 99
TLMSSMTNM                                                                        9

SEQ ID NO: 100              moltype = AA   length = 9
FEATURE                     Location/Qualifiers
REGION                      1..9
                            note = peptide
source                      1..9
                            mol_type = protein
                            organism = synthetic construct
SEQUENCE: 100
MLAVFLPMV                                                                        9

SEQ ID NO: 101              moltype = AA   length = 9
FEATURE                     Location/Qualifiers
REGION                      1..9
                            note = peptide
source                      1..9
                            mol_type = protein
                            organism = synthetic construct
SEQUENCE: 101
MLAVFLPLV                                                                        9

SEQ ID NO: 102              moltype = AA   length = 9
FEATURE                     Location/Qualifiers
REGION                      1..9
                            note = peptide
source                      1..9
                            mol_type = protein
                            organism = synthetic construct
SEQUENCE: 102
YLAVFLPIV                                                                        9

SEQ ID NO: 103              moltype = AA   length = 9
FEATURE                     Location/Qualifiers
REGION                      1..9
                            note = peptide
source                      1..9
                            mol_type = protein
                            organism = synthetic construct
SEQUENCE: 103
SLGYLFLLM                                                                        9

SEQ ID NO: 104              moltype = AA   length = 9
FEATURE                     Location/Qualifiers
REGION                      1..9
                            note = peptide
source                      1..9
                            mol_type = protein
                            organism = synthetic construct
SEQUENCE: 104
SLGFLFLLM                                                                        9

SEQ ID NO: 105              moltype = AA   length = 9
FEATURE                     Location/Qualifiers
REGION                      1..9
                            note = peptide
source                      1..9
                            mol_type = protein
                            organism = synthetic construct
SEQUENCE: 105
SLGFLFLLF                                                                        9

SEQ ID NO: 106              moltype = AA   length = 9
FEATURE                     Location/Qualifiers
REGION                      1..9
                            note = peptide
source                      1..9
                            mol_type = protein
                            organism = synthetic construct
SEQUENCE: 106
MLFAVLMCL                                                                        9

SEQ ID NO: 107              moltype = AA   length = 9
FEATURE                     Location/Qualifiers
REGION                      1..9
```

```
                        note = peptide
source                  1..9
                        mol_type = protein
                        organism = synthetic construct
SEQUENCE: 107
SVASTITGV                                                                    9

SEQ ID NO: 108          moltype = AA   length = 9
FEATURE                 Location/Qualifiers
REGION                  1..9
                        note = peptide
source                  1..9
                        mol_type = protein
                        organism = synthetic construct
SEQUENCE: 108
LLYKLADLI                                                                    9

SEQ ID NO: 109          moltype = AA   length = 10
FEATURE                 Location/Qualifiers
REGION                  1..10
                        note = peptide
source                  1..10
                        mol_type = protein
                        organism = synthetic construct
SEQUENCE: 109
QLAVSVILRV                                                                  10

SEQ ID NO: 110          moltype = AA   length = 9
FEATURE                 Location/Qualifiers
REGION                  1..9
                        note = peptide
source                  1..9
                        mol_type = protein
                        organism = synthetic construct
SEQUENCE: 110
KFLDALISL                                                                    9

SEQ ID NO: 111          moltype = AA   length = 9
FEATURE                 Location/Qualifiers
REGION                  1..9
                        note = peptide
source                  1..9
                        mol_type = protein
                        organism = synthetic construct
SEQUENCE: 111
GVLVGVALI                                                                    9

SEQ ID NO: 112          moltype = AA   length = 9
FEATURE                 Location/Qualifiers
REGION                  1..9
                        note = peptide
source                  1..9
                        mol_type = protein
                        organism = synthetic construct
SEQUENCE: 112
HLFGYSWYK                                                                    9

SEQ ID NO: 113          moltype = AA   length = 9
FEATURE                 Location/Qualifiers
REGION                  1..9
                        note = peptide
source                  1..9
                        mol_type = protein
                        organism = synthetic construct
SEQUENCE: 113
TMNGSKSPV                                                                    9

SEQ ID NO: 114          moltype = AA   length = 9
FEATURE                 Location/Qualifiers
REGION                  1..9
                        note = peptide
source                  1..9
                        mol_type = protein
                        organism = synthetic construct
SEQUENCE: 114
FMVEDETVL                                                                    9

SEQ ID NO: 115          moltype = AA   length = 9
FEATURE                 Location/Qualifiers
```

```
REGION                    1..9
                          note = peptide
source                    1..9
                          mol_type = protein
                          organism = synthetic construct
SEQUENCE: 115
ITDQVPFSV                                                                 9

SEQ ID NO: 116            moltype = AA  length = 9
FEATURE                   Location/Qualifiers
REGION                    1..9
                          note = peptide
source                    1..9
                          mol_type = protein
                          organism = synthetic construct
SEQUENCE: 116
IISAVVGIL                                                                 9

SEQ ID NO: 117            moltype = AA  length = 9
FEATURE                   Location/Qualifiers
REGION                    1..9
                          note = peptide
source                    1..9
                          mol_type = protein
                          organism = synthetic construct
SEQUENCE: 117
ILHNGAYSL                                                                 9

SEQ ID NO: 118            moltype = AA  length = 9
FEATURE                   Location/Qualifiers
REGION                    1..9
                          note = peptide
source                    1..9
                          mol_type = protein
                          organism = synthetic construct
SEQUENCE: 118
KIFGSLAFL                                                                 9

SEQ ID NO: 119            moltype = AA  length = 9
FEATURE                   Location/Qualifiers
REGION                    1..9
                          note = peptide
source                    1..9
                          mol_type = protein
                          organism = synthetic construct
SEQUENCE: 119
PLTSIISAV                                                                 9

SEQ ID NO: 120            moltype = AA  length = 9
FEATURE                   Location/Qualifiers
REGION                    1..9
                          note = peptide
source                    1..9
                          mol_type = protein
                          organism = synthetic construct
SEQUENCE: 120
RLLQETELV                                                                 9

SEQ ID NO: 121            moltype = AA  length = 9
FEATURE                   Location/Qualifiers
REGION                    1..9
                          note = peptide
source                    1..9
                          mol_type = protein
                          organism = synthetic construct
SEQUENCE: 121
TLEEITGYL                                                                 9

SEQ ID NO: 122            moltype = AA  length = 9
FEATURE                   Location/Qualifiers
REGION                    1..9
                          note = peptide
source                    1..9
                          mol_type = protein
                          organism = synthetic construct
SEQUENCE: 122
VVLGVVFGI                                                                 9

SEQ ID NO: 123            moltype = AA  length = 9
```

```
FEATURE              Location/Qualifiers
REGION               1..9
                     note = peptide
source               1..9
                     mol_type = protein
                     organism = synthetic construct
SEQUENCE: 123
WLPFGFILI                                                                    9

SEQ ID NO: 124       moltype = AA  length = 9
FEATURE              Location/Qualifiers
REGION               1..9
                     note = peptide
source               1..9
                     mol_type = protein
                     organism = synthetic construct
SEQUENCE: 124
KVLEYVIKV                                                                    9

SEQ ID NO: 125       moltype = AA  length = 9
FEATURE              Location/Qualifiers
REGION               1..9
                     note = peptide
source               1..9
                     mol_type = protein
                     organism = synthetic construct
SEQUENCE: 125
EVDPIGHLY                                                                    9

SEQ ID NO: 126       moltype = AA  length = 9
FEATURE              Location/Qualifiers
REGION               1..9
                     note = peptide
source               1..9
                     mol_type = protein
                     organism = synthetic construct
SEQUENCE: 126
VAELVHFLL                                                                    9

SEQ ID NO: 127       moltype = AA  length = 9
FEATURE              Location/Qualifiers
REGION               1..9
                     note = peptide
source               1..9
                     mol_type = protein
                     organism = synthetic construct
SEQUENCE: 127
EVDPASNTY                                                                    9

SEQ ID NO: 128       moltype = AA  length = 9
FEATURE              Location/Qualifiers
REGION               1..9
                     note = peptide
source               1..9
                     mol_type = protein
                     organism = synthetic construct
SEQUENCE: 128
KVVEFLAML                                                                    9

SEQ ID NO: 129       moltype = AA  length = 9
FEATURE              Location/Qualifiers
REGION               1..9
                     note = peptide
source               1..9
                     mol_type = protein
                     organism = synthetic construct
SEQUENCE: 129
SFSYTLLSL                                                                    9

SEQ ID NO: 130       moltype = AA  length = 9
FEATURE              Location/Qualifiers
REGION               1..9
                     note = peptide
source               1..9
                     mol_type = protein
                     organism = synthetic construct
SEQUENCE: 130
VSSFFSYTL                                                                    9
```

-continued

| | | |
|---|---|---|
| SEQ ID NO: 131<br>FEATURE<br>REGION<br><br>source | moltype = AA   length = 9<br>Location/Qualifiers<br>1..9<br>note = peptide<br>1..9<br>mol_type = protein<br>organism = synthetic construct | |
| SEQUENCE: 131<br>ALKDVEERV | | 9 |
| SEQ ID NO: 132<br>FEATURE<br>REGION<br><br>source | moltype = AA   length = 9<br>Location/Qualifiers<br>1..9<br>note = peptide<br>1..9<br>mol_type = protein<br>organism = synthetic construct | |
| SEQUENCE: 132<br>ASSTLYLVF | | 9 |
| SEQ ID NO: 133<br>FEATURE<br>REGION<br><br>source | moltype = AA   length = 9<br>Location/Qualifiers<br>1..9<br>note = peptide<br>1..9<br>mol_type = protein<br>organism = synthetic construct | |
| SEQUENCE: 133<br>PLLENVISK | | 9 |
| SEQ ID NO: 134<br>FEATURE<br>REGION<br><br>source | moltype = AA   length = 9<br>Location/Qualifiers<br>1..9<br>note = peptide<br>1..9<br>mol_type = protein<br>organism = synthetic construct | |
| SEQUENCE: 134<br>ILTVILGVL | | 9 |
| SEQ ID NO: 135<br>FEATURE<br>REGION<br><br>source | moltype = AA   length = 9<br>Location/Qualifiers<br>1..9<br>note = peptide<br>1..9<br>mol_type = protein<br>organism = synthetic construct | |
| SEQUENCE: 135<br>ALLALTSAV | | 9 |
| SEQ ID NO: 136<br>FEATURE<br>REGION<br><br>source | moltype = AA   length = 9<br>Location/Qualifiers<br>1..9<br>note = peptide<br>1..9<br>mol_type = protein<br>organism = synthetic construct | |
| SEQUENCE: 136<br>GLPPDVQRV | | 9 |
| SEQ ID NO: 137<br>FEATURE<br>REGION<br><br>source | moltype = AA   length = 9<br>Location/Qualifiers<br>1..9<br>note = peptide<br>1..9<br>mol_type = protein<br>organism = synthetic construct | |
| SEQUENCE: 137<br>LAMPFATPM | | 9 |
| SEQ ID NO: 138<br>FEATURE<br>REGION<br><br>source | moltype = AA   length = 9<br>Location/Qualifiers<br>1..9<br>note = peptide<br>1..9<br>mol_type = protein<br>organism = synthetic construct | |
| SEQUENCE: 138<br>ALDVYNGLL | | 9 |

```
SEQ ID NO: 139          moltype = AA   length = 9
FEATURE                 Location/Qualifiers
REGION                  1..9
                        note = peptide
source                  1..9
                        mol_type = protein
                        organism = synthetic construct
SEQUENCE: 139
FLFLLFFWL                                                               9

SEQ ID NO: 140          moltype = AA   length = 9
FEATURE                 Location/Qualifiers
REGION                  1..9
                        note = peptide
source                  1..9
                        mol_type = protein
                        organism = synthetic construct
SEQUENCE: 140
TLMSAMTNL                                                               9

SEQ ID NO: 141          moltype = AA   length = 9
FEATURE                 Location/Qualifiers
REGION                  1..9
                        note = peptide
source                  1..9
                        mol_type = protein
                        organism = synthetic construct
SEQUENCE: 141
MIAVFLPIV                                                               9

SEQ ID NO: 142          moltype = AA   length = 9
FEATURE                 Location/Qualifiers
REGION                  1..9
                        note = peptide
source                  1..9
                        mol_type = protein
                        organism = synthetic construct
SEQUENCE: 142
SLGWLFLLL                                                               9

SEQ ID NO: 143          moltype = AA   length = 9
FEATURE                 Location/Qualifiers
REGION                  1..9
                        note = peptide
source                  1..9
                        mol_type = protein
                        organism = synthetic construct
SEQUENCE: 143
MLLAVLYCL                                                               9

SEQ ID NO: 144          moltype = AA   length = 20
FEATURE                 Location/Qualifiers
REGION                  1..20
                        note = peptide
source                  1..20
                        mol_type = protein
                        organism = synthetic construct
SEQUENCE: 144
MAKTIAYDEE ARRGLERGLN                                                  20
```

IMMUNOGENIC COMPOUNDS FOR CANCER THERAPY

FIELD OF THE INVENTION

The present invention is in the field of cancer therapy, more particularly through immunotherapeutic methods.

REFERENCE TO AN ELECTRONIC SEQUENCE LISTING

The contents of the electronic sequence listing (ST26_SL_Conversion_8_18_22.xml; Size: 173 KB; and Date of Creation: 18 Aug. 2022) is herein incorporated by reference in its entirety.

BACKGROUND OF THE INVENTION

Cancer is one of the leading causes of death across the world. According to the World Health Organization, in 2012 only, 14 million new cases and 8.2 million cancer-related deaths were reported worldwide, and it is expected that the number of new cancer cases will rise by about 70% within the next two decades. So far, more than 60% of world's total new annual cases occur in Africa, Asia and Central and South America. These regions also account for 70% of the world's cancer deaths. Among men, the five most common sites of cancer are lung, prostate, colorectum, stomach and liver; while in women, those are breast, colorectum, lung, cervix, and stomach.

Cancer has long been managed with surgery, radiation therapy, cytotoxic chemotherapy, and endocrine manipulation, which are typically combined in sequential order so as to best control the disease. However, major limitations to the true efficacy of these standard therapies are their imprecise specificity, which leads to the collateral damage of normal tissues incurred with treatment, a low cure rate, and intrinsic drug resistance.

In the last years, there has been a tremendous increase in the development of cancer therapies due notably to great advances in the expression profiling of tumors and normal cells, and recent researches and first clinical results in immunotherapy, or molecular targeted therapy, have started to change our perception of this disease.

Promising anticancer immunotherapies have now become a reality and evidences that the host immune system can recognize tumor antigens have led to the development of anticancer drugs, which are now approved by regulatory agencies as the US Food and Drug Administration (FDA) and European Medicines Agency (EMA). Various therapeutic approaches include, among others, adoptive transfer of ex vivo expanded tumor-infiltrating lymphocytes, cancer cell vaccines, immunostimulatory cytokines and variants thereof, Pattern recognition receptor (PRR) agonists, and immunomodulatory monoclonal antibodies targeting tumor antigens or immune checkpoints (Galuzzi et al., Classification of current anticancer immunotherapies. Oncotarget. 2014 Dec. 30;5 (24): 12472-508).

Unfortunately, a significant percentage of patients can still present an intrinsic resistance to some of these immunotherapies or even acquire resistance during the course of treatment. For example, the three-year survival rate has been reported to be around 20% with the anti-CTLA-4 antibody Ipilumumab in unresectable or metastatic melanoma (Snyder et al., Genetic basis for clinical response to CTLA-4 blockade in melanoma. N Engl J Med. 2014 Dec. 4;371 (23): 2189-2199; Schadendorf et al., Pooled Analysis of Long-Term Survival Data From Phase II and Phase III Trials of Ipilimumab in Unresectable or Metastatic Melanoma. J Clin Oncol. 2015 Jun. 10;33 (17): 1889-94), while the three-year survival rate with another check point inhibitor, Nivolumab targeting PD1, has been reported to be of 44% in renal cell carcinoma (RCC) and 18% in NSCLC (Mc Dermott et al., Survival, Durable Response, and Long-Term Safety in Patients With Previously Treated Advanced Renal Cell Carcinoma Receiving Nivolumab. J Clin Oncol. 2015 Jun. 20;33 (18): 2013-20; Gettinger et al., Overall Survival and Long-Term Safety of Nivolumab (Anti-Programmed Death 1 Antibody, BMS-936558, ONO-4538) in Patients With Previously Treated Advanced Non-Small-Cell Lung Cancer. J Clin Oncol. 2015 Jun. 20;33 (18): 2004-12). Fundamental drug resistance thus represents a fixed barrier to the efficacy of these immunotherapies. It is thus clear that a different approach to cancer treatment is needed to break this barrier.

Absence of response in a large number of subjects treated with these immunotherapies might be associated with a deficient anti-tumor immune response (as defect in antigen presentation by APC or antigen recognition by T cells). In other words, positive response to immunotherapy correlates with the ability of the immune system to develop specific lymphocytes subsets able to recognize MHC class I-restricted antigens that are expressed by human cancer cells (Kvistborg et al., Human cancer regression antigens. Curr Opin Immunol. 2013 April; 25 (2): 284-90). This hypothesis is strongly supported by data demonstrating that response to adoptive transfer of tumor-infiltrating lymphocytes, is directly correlated with the numbers of CD8 T-cells transfused to the patient (Besser et al., Adoptive transfer of tumor-infiltrating lymphocytes in patients with metastatic melanoma: intent-to-treat analysis and efficacy after failure to prior immunotherapies. Clin Cancer Res. 2013 Sep. 1;19 (17): 4792-800). A potent anti-tumoral response will thus depend on the presentation of immunoreactive peptides and the presence of a sufficient number of reactive cells "trained" to recognize these antigens.

Tumor antigen-based vaccination represent a unique approach to cancer therapy that has gained considerable interest as it can enlist the patient's own immune system to recognize, attack and destroy tumors, in a specific and durable manner. Tumor cells are indeed known to express a large number of peptide antigens susceptible to be recognized by the immune system. Vaccines based on such antigens thus provide great opportunities not only to improve patient's overall survival but also for the monitoring of immune responses and the preparation of GMP-grade product thanks to the low toxicity and low molecular weight of tumor antigens. Examples of tumor antigens include, among others, by-products of proteins transcribed from normally silent genes or overexpressed genes and from proteins expressed by oncovirus (Kvistborg et al., Human cancer regression antigens. Curr Opin Immunol. 2013 April; 25 (2): 284-90), and neo-antigens, resulting from point mutations of cellular proteins. The later are of particular interest as they have been shown to be directly associated with increased overall survival in patient treated with CTLA4 inhibitors (Snyder et al., Genetic basis for clinical response to CTLA-4 blockade in melanoma. N Engl J Med. 2014 Dec. 4;371 (23): 2189-2199; Brown et al., Neo-antigens predicted by tumor genome meta-analysis correlate with increased patient survival. Genome Res. 2014 May;24 (5): 743-50).

Nevertheless, the number of human tumor antigens on which cancer vaccines can be developed is limited. In particular, antigens derived from mutated or modified self-proteins may induce immune tolerance and/or undesired autoimmunity side effects.

There is thus a need in the art to identify alternative cancer therapeutics, which can overcome the limitations encountered in this field, notably resistance to immunotherapies that are currently available.

The invention has for objective to meet the aforementioned needs.

SUMMARY OF THE INVENTION

The invention relates to an antigenic peptide having amino acid similarity with a tumor antigen, which antigenic peptide is selected in the group consisting of SEQ ID NO: 1 to 106. In other words, the present invention relates to an antigenic peptide having an amino acid sequence as set forth in any one of SEQ ID NO: 1 to 106. An antigenic peptide according to the invention can be in the form of an immunogenic compound.

Thus, according to certain embodiments, the invention relates to an immunogenic compound comprising an antigenic peptide having amino acid similarity with a tumor antigen, which antigenic peptide is selected in the group consisting of SEQ ID NO: 1 to 106, and in particular SEQ ID NO:71. In other words, the present invention relates to an immunogenic compound comprising an antigenic peptide having an amino acid sequence as set forth in any one of SEQ ID NO:1 to 106.

More particularly, the invention relates to an immunogenic compound as defined above, wherein the said antigenic peptide is linked to a carrier protein.

The present invention relates also to a nanoparticle loaded with at least antigenic peptide according to the present invention or with at least one immunogenic compound according to the present invention, and, optionally, with an adjuvant.

The invention also relates to a composition comprising an antigenic peptide or an immunogenic compound as above defined, the said composition preferably further comprising one or more pharmaceutically acceptable excipients.

Thus, according to certain embodiments, the invention relates to an immunogenic composition comprising an antigenic peptide or an immunogenic compound as above defined and one or more pharmaceutically acceptable excipients, Preferably, the said immunogenic composition may further comprise one or more immunostimulatory agents.

The said one or more immunostimulatory agents may be selected in a group comprising (or consisting of) immunoadjuvants and antigen-presenting cells.

The said antigen-presenting cells may consist of dendritic cells.

According to other embodiments, the invention relates to an antigenic peptide as above defined or an immunogenic compound as above defined, for use in the prevention or in the treatment of a cancer.

According to further embodiments, the invention relates to an immunogenic composition for use in the prevention or in the treatment of a cancer.

This invention also pertains to the use of an antigenic peptide as above defined or of an immunogenic compound as above defined, for preparing a medicament for treating or preventing a cancer.

This invention also concerns a method for preventing or treating a cancer in an individual in need thereof, wherein the said method comprises a step of administering to the said individual an antigenic peptide as above defined or an immunogenic compound as above defined or an immunogenic composition as above defined or a nanoparticle according to the present invention or a nucleic acid according to the present invention or a combination according to the present invention.

According to yet further embodiments, the invention relates to a nucleic acid coding for an antigenic peptide or an immunogenic compound as above defined.

Furthermore, the present invention also relates to a combination of two distinct immunogenic compounds according to the present invention for use in the prevention and/or treatment of a cancer. Furthermore, the present invention also relates to a combination of two distinct antigenic peptides according to the present invention for use in the prevention and/or treatment of a cancer. Furthermore, the present invention also relates to a combination of two distinct nanoparticles according to the present invention for use in the prevention and/or treatment of a cancer. Furthermore, the present invention also relates to a combination of two distinct nucleic acids according to the present invention for use in the prevention and/or treatment of a cancer.

In certain embodiments, the two distinct components of the combination for use according to the present invention are comprised in the same or distinct compositions.

In certain embodiments, the two distinct components of the combination for use according to the present invention are administered via the same or distinct routes of administration.

In certain embodiments, the two distinct components of the combination for use according to the present invention are administered at about the same time or consecutively.

Furthermore, the present invention also relates to a kit comprising
- an immunogenic compound according to the present invention,
- an antigenic peptide according to the present invention,
- a nanoparticle according to the present invention,
- a nucleic acid according to the present invention, or
- an immunogenic composition according to the present invention.

DETAILED DESCRIPTION OF THE INVENTION

Figure 1:
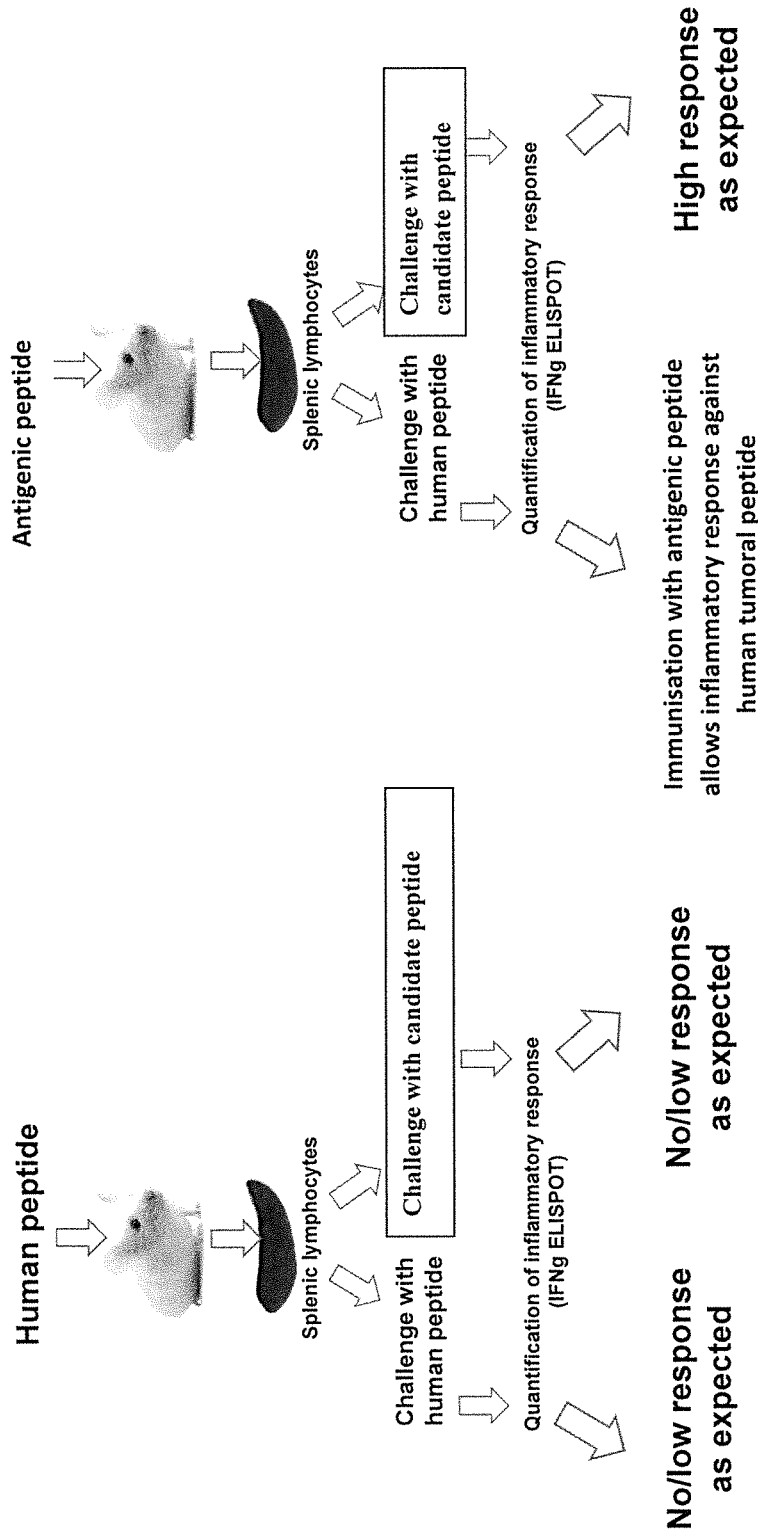
FIG. 1: General protocol for the validation of the Proof-of-concept of a tumor antigen-based immunotherapy targeting IL13RA2.

The inventors have identified a set of antigenic peptides that can be used to induce a specific immune response against tumor cells.

Those antigenic peptides all share the property of having amino acid similarity with tumor antigens encoded by the set of genes disclosed in Table 1A and Table 1B.

For instance, the Interleukin-13 receptor subunit alpha-2 (IL-13Rα2 or IL13RA2) is a membrane bound protein that in humans is encoded by the IL13RA2 gene. In a non-exhaustive manner, IL13RA2 has been reported as a potential immunotherapy target (see Beard et al.; Clin Cancer Res; 72 (11); 2012). The high expression of IL13RA2 has further been associated with invasion, liver metastasis and poor prognosis in colorectal cancer (Barderas et al.; Cancer Res; 72 (11); 2012).

Accordingly, the invention relates to antigenic peptides having amino acid similarity with a tumor antigen, which antigenic peptide is selected in the group consisting of SEQ ID NO: 1 to 106.

The expression "having amino acid similarity with a tumor antigen" as used herein, refer in particular to sequence variants of fragments of a (reference) tumor antigen, such as IL13RA2.

A sequence variant shares, in particular over the whole length of the sequence, at least 50% sequence identity with a reference sequence, namely, a fragment of a (reference) tumor antigen. Preferably, the sequence variant shares at least 60%, preferably at least 70%, preferably at least 75%, more preferably at least 80%, even more preferably at least 85%, still more preferably at least 90%, particularly preferably at least 95%, and most preferably at least 99% sequence identity with a reference sequence, namely, a fragment of a (reference) tumor antigen. Sequence identity may be calculated as described below. Preferably, a sequence variant preserves the specific function of the reference sequence, for example its function as epitope. In particular, an amino acid sequence variant has an altered sequence in which one or more of the amino acids in the reference sequence is deleted or substituted, or one or more amino acids are inserted into the sequence of the reference amino acid sequence. For example, variant sequences, which are at least 90% identical, have no more than 10 alterations, i.e. any combination of deletions, insertions or substitutions, per 100 amino acids of the reference sequence.

Methods for comparing the identity (similarity) of two or more sequences are well known in the art. The percentage to which two sequences are identical can, e.g., be determined using a mathematical algorithm. A preferred, but not limiting, example of a mathematical algorithm, which can be used, is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U.S.A 85, 2444-2448). Sequences that are identical to other sequences to a certain extent can be identified by these programmes. Furthermore, programs available in the Wisconsin Sequence Analysis Package, version 9.1 (Devereux et al., 1984, Nucleic Acids Res., 387-395), for example the programs BESTFIT and GAP, may also be used to determine the % identity between two polynucleotides and the % identity between two (poly)peptide sequences. BESTFIT uses the "local homology" algorithm of Smith and Waterman (1981), J. Mol. Biol. 147, 195-197 and finds the best single region of similarity between two sequences.

The "fragment" of the (reference) tumor antigen, which typically serves as reference sequence, comprises at least seven, preferably at least eight and most preferably (at least) nine amino acids or ten amino acids.

Advantageously, those antigenic peptides may be in the form of immunogenic compounds, in particular for use in the prevention or in the treatment of a cancer.

Thus, the invention also relates to an immunogenic compound comprising an antigenic peptide having amino acid similarity with a tumor antigen, which antigenic peptide is selected in the group consisting of SEQ ID NO:1 to 106. In other words, the present invention provides an antigenic peptide having an amino acid sequence as set forth in any one of SEQ ID NO:1 to 106. Preferably, the present invention provides (an immunogenic compound comprising) an antigenic peptide comprising or consisting of an amino acid sequence as set forth in any one of SEQ ID NOs: 17, 31, 32, 51, 52, 55, 56, 59, 68, 89, 94, 100, 101 or 102. It is also preferred that the present invention provides (an immunogenic compound comprising) an antigenic peptide comprising or consisting of an amino acid sequence as set forth in any one of SEQ ID NOs: 26, 28, 47, 51, 52, 55, 56, 77, 93, 101 or 102. More preferably, the present invention provides (an immunogenic compound comprising) an antigenic peptide comprising or consisting of an amino acid sequence as set forth in any one of SEQ ID NOs: 51, 52, 55, 56, 101 or 102. Even more preferably, the present invention provides (an immunogenic compound comprising) an antigenic peptide comprising or consisting of an amino acid sequence as set forth in any one of SEQ ID NOs: 51, 52, 55 or 56. It is also even more preferred that the present invention provides (an immunogenic compound comprising) an antigenic peptide comprising or consisting of an amino acid sequence as set forth in any one of SEQ ID NOs: 101 or 102.

As shown in the examples herein, the said specific antigenic peptides according to the present invention allow the raise of a strong immune response against themselves, and most importantly, allow the raise of a strong immune response against peptides having amino acid similarity therewith which are comprised in the IL13RA2 tumor antigen, although the said peptides comprised in the IL13RA2 tumor antigen are themselves tolerogenic.

Without wishing to be bound by any particular theory, the inventors believe that the high expression of gamma interferon which has been measured after an in vivo administration of an immunogenic composition comprising an antigenic peptide described herein illustrates the activation of antigenic peptide-specific T-cells, and especially the activation of antigenic peptide-specific CTLs, which cells are known in the art to be relevant immune effectors of an anti-cancer immune response.

Unless otherwise defined herein, scientific and technical terms used in connection with the present invention shall have the meanings that are commonly understood by those of ordinary skill in the art. Further, unless otherwise required by context, nomenclatures used herein, and techniques of cell and tissue culture are those well-known and commonly used in the art.

Such techniques are fully explained in the literature, such as Owen et al. (Kuby Immunology, 7th, edition, 2013-W. H. Freeman) and Sambrook et al. (Molecular cloning: A laboratory manual 4th edition, Cold Spring Harbor Laboratory Press-Cold Spring Harbor, NY, USA, 2012).

Nevertheless, with respect to the use of different terms throughout the current specification, the following definitions more particularly apply.

The terms "peptide", "polypeptide" and "protein" refer herein to a sequential chain of amino acids of any length linked together via peptide bonds (—NHCO—), and which can play a structural and/or functional role in a cell in vitro and/or in vivo. It encompasses amino acids chains in size ranging from 2 to at least about 1000 amino acid residues. The term "peptide" preferably encompasses herein amino acid chains in size of less than about amino acids, while the terms "polypeptide" and "protein" preferably encompass amino acid chains in size of at least 30 amino acids. The terms "polypeptide" and "protein" are used herein interchangeably. As well-known in the art, peptides, polypeptides and proteins can be encoded by nucleic acids.

The term "antigenic peptide" refers to a peptide, which preferably has amino acid similarity with a tumor protein, and which is prone to induce or maintain an immunological response against said peptide in a subject to whom it is administered.

The term "immunogenic compound" refers to a compound comprising an antigenic peptide as defined above, which is also able to induce or maintain an immunological response against said peptide from the subject for whom it is administered.

In some embodiments, immunogenic compounds comprise at least one antigenic peptide, or alternatively at least one compound comprising such an antigenic peptide, linked to a protein, which encompasses a carrier protein.

A carrier protein is usually a protein, which is able to transport a cargo, such as the antigenic peptide according to the present invention. For example, the carrier protein may transport its cargo across a membrane. In the context of the present invention, a carrier protein in particular (also) encompasses a peptide or a polypeptide that is able to elicit an immune response against the antigenic peptide that is linked thereto. Carrier proteins are known in the art.

In some embodiments, an antigenic peptide as described herein, or a polypeptide comprising the said antigenic peptide, may be linked, for example by covalent or non-covalent bond, to a protein having immuno-adjuvant properties, such as the HHD-DR3 peptide of sequence MAKTIAYDEE-ARRGLERGLN (SEQ ID NO:144).

Alternatively such carrier peptide or polypeptide may be co-administered in the form of immune adjuvant.

Preferably, the antigenic peptide as described herein, or a polypeptide comprising the antigenic peptide, may be co-administrated or linked, for example by covalent or non-covalent bond, to a protein/peptide having immuno-adjuvant properties, such as providing stimulation of CD4+Th1 cells. While the antigenic peptide as described herein preferably binds to MHC class I, CD4+ helper epitopes may be additionally used to provide an efficient immune response. Th1 helper cells are able to sustain efficient dendritic cell (DC) activation and specific CTL activation by secreting interferon-gamma (IFN-γ), tumor necrosis factor-alpha (TNF-α) and interleukine-2 (IL-2) and enhancing expression of costimulatory signal on DCs and T cells (Galaine et al., Interest of Tumor-Specific CD4 T Helper 1 Cells for Therapeutic Anticancer Vaccine. Vaccines (Basel). 2015 Jun. 30;3 (3): 490-502).

For example, the adjuvant peptide/protein may preferably be a non-tumor antigen that recalls immune memory or provides a non-specific help or could be a specific tumor-derived helper peptide. Several helper peptides have been described in the literature for providing a nonspecific T cell help, such as tetanus helper peptide, keyhole limpet hemocyanin peptide or PADRE peptide (Adotévi et al., Targeting antitumor CD4 helper T cells with universal tumor-reactive helper peptides derived from telomerase for cancer vaccine. Hum Vaccin Immunother. 2013 May;9 (5): 1073-7, Slingluff CL, The present and future of peptide vaccines for cancer: single or multiple, long or short, alone or in combination? Cancer J. 2011 September-Oct; 17 (5): 343-50). Accordingly, tetanus helper peptide, keyhole limpet hemocyanin peptide and PADRE peptide are preferred examples of such adjuvant peptide/proteins. Moreover, specific tumor derived helper peptides are preferred. Specific tumor derived helper peptides are typically presented by MHC class II, in particular by HLA-DR, HLA-DP or HLA-DQ. Specific tumor derived helper peptides may be fragments of sequences of shared overexpressed tumor antigens, such as HER2, NY-ESO-1, hTERT or IL13RA2. Such fragments have preferably a length of at least 10 amino acids, more preferably of at least 11 amino acids, even more preferably of at least 12 amino acids and most preferably of at least 13 amino acids.

In particular, fragments of shared overexpressed tumor antigens, such as HER2, NY-ESO-1, hTERT or IL13RA2, having a length of 13 to 24 amino acids are preferred. Preferred fragments bind to MHC class II and may, thus, be identified using, for example, the MHC class II binding prediction tools of IEDB (Immune epitope database and analysis resource; Supported by a contract from the National Institute of Allergy and Infectious Diseases, a component of the National Institutes of Health in the Department of Health and Human Services; www.iedb.org/; tools.iedb.org/mhcii/.

A composition as defined herein which comprises an immunogenic compound as defined above, and which further comprises one or more immuno-adjuvant substances, may also be termed an "immunogenic composition" or in some embodiments a "vaccine composition" in the present specification.

As used herein, the term "immunogenic composition" refers to a composition that is able to induce or maintain an immune response, in particular which induces an immune response, when it is administered to a mammal, and especially when it is administered to a human individual.

The terms "nucleic acid", "nucleic acid molecule", "nucleic acid sequence", "polynucleotide", "nucleotide sequence", which are used herein interchangeable, refer to a precise succession of natural nucleotides (e.g., A, T, G, C and U), or synthetic nucleotides, corresponding to a single-stranded or double-stranded DNA or RNA, such as cDNA, genomic DNA, ribosomal DNA, and the transcription product of said DNA, such as RNA, rRNA, mRNA; antisense DNA, antisense RNA; complementary RNA and/or DNA sequences; RNA and/or DNA sequences with or without expression elements, regulatory elements, and/or promoters; a vector; and combinations thereof. It is within the skill of the person in the art to determine nucleotide sequences that can encode a specific amino acid sequence.

The (poly)peptides and/or nucleic acids according to the invention may be prepared by any known method in the art including, but not limited to, any synthetic method, any recombinant method, any ex vivo generation method and the like, and any combination thereof. Such techniques are fully explained in the literature as mentioned above.

In the context of the present invention, the antigenic peptides according to the invention comprise antigens having similarity with a tumor antigen. As used herein, the term "tumor antigen" comprises tumor-specific antigens and tumor-associated antigens. In general., the term "tumor antigen" or "tumor protein" designates herein an antigenic substance produced in tumor cells, and sometimes also in normal cells, and which can trigger an immune response upon administration in a subject. In humans, those have been classified according to their expression pattern, function or genetic origin, and include without limitation, overexpressed self-antigens (such as HER2/neu and its variant dHER2, p53, Wilm's Tumor 1, Ephrin receptor, Proteinase-3, Mucin-1, Mesothelin, EGFR, CD20); cancer-testis (CT) antigens (such as MAGE-1, BAGE, GAGE, NY-ESO-1); mutational antigens, also known as neo-antigens (such as mutants from MUM-1, bcr-abl, ras, b-raf, p53, CDK-4, CDC27, beta-catenin, alpha-actenin-4); tissue-specific differentiation antigens (such as the melanoma antigens Melan A/MART-1, tyrosinase, TRP1/pg75, TRP2, gp100 and gangliosides GM3, GM2, GD2 and GD3; the prostate cancer antigens PSMA, PSA and PAP); viral antigens which are expressed by oncoviruses (such as HPV, EBV); oncofetal antigens (such as alphafetoprotein AFP and carcinoembryonic antigen CEA); and universal antigens (telomerase, hTERT, survivin, mdm-2, CYP-1B1) (Srinivasan and Wolchok, Tumor antigens for cancer immunotherapy: therapeutic potential of xenogeneic DNA vaccines. J Transl Med. 2004 Apr. 16;2 (1): 12).

According to the different aspects and embodiments of the invention described herein, a "subject" or "host" preferably refers to a mammal, and most preferably to a human being. Said subject may have, been suspected of having, or be at risk of developing cancer, for example melanoma, colorectal cancer or clear cell renal cell carcinoma.

By "pharmaceutically acceptable excipient", it is meant herein a compound of pharmaceutical grade which improves the delivery, stability or bioavailability of an active agent, and can be metabolized by, and is non-toxic to, a subject to whom it is administered. Preferred excipients according to the invention include any of the excipients commonly used in pharmaceutical products, such as, for example, water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable excipients may further comprise minor amounts of auxiliary substances such as wetting or emulsifying agents, or preservatives.

By "vaccine", it is meant herein a composition capable of stimulating the immune system of a living organism so that protection against a harmful antigen is provided, either through prophylaxis or through therapy.

The term "cancer", as used herein, refers to a malignant neoplasm. In particular, the term "cancer" refers herein to any member of a class of diseases or disorders that are characterized by uncontrolled division of cells and the ability of these cells to invade other tissues, either by direct growth into adjacent tissue through invasion or by implantation into distant sites by metastasis. Metastasis is defined as the stage in which cancer cells are transported through the bloodstream or lymphatic system. It encompasses, among others, esophageal cancer, gastric cancer, duodenal cancer, small intestinal cancer, appendiceal cancer, large bowel cancer, colon cancer, rectum cancer, colorectal cancer, anal cancer, pancreatic cancer, liver cancer, gallbladder cancer, spleen cancer, renal cancer, bladder cancer, prostatic cancer, testicular cancer, uterine cancer, endometrial cancer, ovarian cancer, vaginal cancer, vulvar cancer, breast cancer, pulmonary cancer, thyroid cancer, thymus cancer, brain cancer, nervous system cancer, oral cavity cancer, skin cancer, blood cancer, lymphomas, eye cancer, bone cancer, bone marrow cancer, muscle cancer, etc., In the context of the present invention, melanoma, head and neck, breast, colorectal cancer or clear cell renal cell carcinoma are preferred.

As used herein, the term "preventing", "prevention", "prophylaxis" or "prevent" generally means to avoid or minimize the onset or development of a disease or condition before its onset, while the term "treating", "treatment" or "treat" encompasses reducing, ameliorating or curing a disease or condition (or symptoms of a disease or condition) after its onset. In the context of the invention, the prevention and/or treatment of cancer can lead, for example, to the non-proliferation, weak, reduced or delayed proliferation of tumor cells within the subject, or to the complete or almost complete elimination of tumor cells within the subject. The term "preventing" encompasses "reducing the likelihood of occurrence of or «reducing the likelihood of reoccurrence».

An "effective amount" or "effective dose" as used herein is an amount which provides the desired effect. For therapeutic purposes, an effective amount is an amount sufficient to provide a beneficial or desired clinical result. The preferred effective amount for a given application can be easily determined by the skilled person taking into consideration, for example, the size, age, weight of the subject, the type of cancer to be prevented or treated, and the amount of time since the cancer began. In the context of the present invention, in terms of prevention or treatment, an effective amount of the composition is an amount that is sufficient to induce a humoral and/or cell-mediated immune response directed against cancer.

As used herein, the term "comprising" encompasses "consisting of".

Additional definitions are provided throughout the specification.

The present invention may be understood more readily by reference to the following detailed description, including preferred embodiments of the invention, and examples included herein.

Thus, the invention relates to an immunogenic compound comprising an antigenic peptide having amino acid similarity with a tumor antigen, which antigenic peptide is selected in the group consisting of SEQ ID NO:1 to 106. In other words, the present invention provides (an immunogenic compound comprising) an antigenic peptide having an amino acid sequence as set forth in any one of SEQ ID NO:1 to 106. Preferably, the present invention provides (an immunogenic compound comprising) an antigenic peptide comprising or consisting of an amino acid sequence as set forth in any one of SEQ ID NOs: 17, 31, 32, 51, 52, 55, 56, 59, 68, 89, 94, 100, 101 or 102. It is also preferred that the present invention provides (an immunogenic compound comprising) an antigenic peptide comprising or consisting of an amino acid sequence as set forth in any one of SEQ ID NOs: 26, 28, 47, 51, 52, 55, 56, 77, 93, 101 or 102. More preferably, the present invention provides (an immunogenic compound comprising) an antigenic peptide comprising or consisting of an amino acid sequence as set forth in any one of SEQ ID NOs: 51, 52, 55, 56, 101 or 102. Even more preferably, the present invention provides (an immunogenic compound comprising) an antigenic peptide comprising or consisting of an amino acid sequence as set forth in any one of SEQ ID NOs: 51, 52, 55 or 56. It is also even more preferred that the present invention provides (an immunogenic compound comprising) an antigenic peptide comprising or consisting of an amino acid sequence as set forth in any one of SEQ ID NOs: 101 or 102.

According to an exemplary embodiment, the antigenic peptide as above defined is a peptide of sequence SEQ ID NO: 71.

According to one embodiment, the antigenic peptide as above defined, or a polypeptide comprising the said antigenic peptide, is linked to a carrier protein, for example by a covalent or non-covalent bond.

According some embodiments, the invention relates to an immunogenic compound as above defined, comprising an antigenic peptide of formula (I):

PepNt-CORE-PepCt(I), wherein:

"PepNt" consists of a polypeptide having an amino acid length varying from 0 to 30 amino acid residues and located at the N-terminal end of the polypeptide of formula (I);

CORE consists of a polypeptide comprising, or alternatively consisting of, an amino acid sequence selected from the group consisting of SEQ ID NO:1 to 106 (which includes SEQ ID NO:71), in particular an amino acid sequence as set forth in any one of SEQ ID NOs: 26, 28, 47, 51, 52, 55, 56, 77, 93, 101 or 102 or an amino acid sequence as set forth in any one of 17, 31, 32, 51, 52, 55, 56, 59, 68, 89, 94, 100, 101 or 102, such as an amino acid sequence as set forth in any one of SEQ ID NOs: 51, 52, 55, 56, 101 or 102; and "PepCt" consists of a polypeptide having an amino acid length varying from 0 to 30 amino acid residues and located at the C-terminal end of the polypeptide of formula (I).

Preferably, the antigenic peptide of formula (I) is a fusion peptide or fusion protein, in particular a recombinant fusion peptide or protein. The term "recombinant" means that it does not occur in nature.

The invention further relates to a nanoparticle loaded with
  at least one of the immunogenic compounds according to the present invention, or
  at least one of the antigenic peptides according to the present invention;
  and, optionally, with an adjuvant The invention further relates to an immunogenic composition comprising
  an immunogenic compound according to the present invention,
  an antigenic peptide according to the present invention,
  a nanoparticle according to the present invention, or
  a nucleic acid according to the present invention,
  and one or more pharmaceutically acceptable excipients.

The immunogenic composition may further comprise one or more immunostimulatory agents.

In particular, the said immunostimulatory agent is selected in a group consisting of immuno-adjuvants and antigen-presenting cells.

More particularly, the antigen-presenting cells may consist of dendritic cells.

In particular, the immunogenic composition may comprise
  (i) two distinct immunogenic compounds according to the present invention;
  (ii) two distinct antigenic peptides according to the present invention;
  (iii) two distinct nanoparticle according to the present invention; or
  (iv) two distinct nucleic acid according to the present invention.

In this context, the two distinct components refer in particular to distinct antigenic peptides according to the present invention (which are comprised by the immunogenic compounds, the nanoparticles and/or the nucleic acids). Such two distinct components, in particular the two distinct antigenic peptides according to the invention (comprised in the two distinct components), relate preferably to the same type of cancer, for example to the same or distinct antigens associated with this cancer and/or to the same or distinct (reference) epitopes within an antigen associated with this cancer. More preferably, the two distinct components, in particular the two distinct antigenic peptides according to the invention (comprised in the two distinct components), relate to the same tumor (associated or specific) antigen. The two distinct components, in particular the two distinct antigenic peptides according to the invention (comprised in the two distinct components), may also relate to the same or distinct (reference) tumor (associated or specific) antigen(s).

The invention further relates to any one of
  the immunogenic compound according to the present invention,
  the antigenic peptide according to the present invention,
  the (host) cell according to the present invention,
  the nanoparticle according to the present invention,
  the nucleic acid according to the present invention, or
  the immunogenic composition according to the present invention, for use in the prevention or in the treatment of a cancer.

Among the different types of cancer, those which are more particularly considered for treatment and/or prevention, are detailed in Table 1B here below, in particular in view of the targeted tumor antigen.

TABLE 1B list of therapeutic indications associated with each gene

| Gene Name (Table 1A) | Cancers in which of the gene is involved |
|---|---|
| PLIN2 | Diseases associated with PLIN2 include lipid-rich carcinoma and acrodermatitis enteropathica and colorectal cancer |
| ALDH1A1 | Diseases associated with ALDH1A1 include lung cancer (including lung adenoma) and breast cancer |
| AFP | Diseases associated with AFP include liver cancer, hepatocellular cancer |
| PTPRC | Breast cancer |
| CEACAM5 | Diseases associated with CEACAM5 include gut carcinoma, colorectal cancer, urachal cancer, gastrointestinal cancer and pancreatic cancer |
| ENAH | Breast cancer |
| EZH2 | Diseases associated with EZH2 include many forms of cancers, including lung cancer and lymphoblastoma |
| PMEL | Melanoma |
| ERBB2 | Diseases associated with ERBB2 include numerous cancers, including breast cancer, glioma and ovarian cancer |

TABLE 1B-continued list of therapeutic indications associated with each gene

| Gene Name (Table 1A) | Cancers in which of the gene is involved |
| --- | --- |
| IL13RA2 | Diseases associated with IL13RA2 include colorectal cancer, ovarian cancer, testis cancer, renal cell carcinoma, prostate cancer, glioma, head and neck cancer, astrocytoma, melanoma and breast cancer metastasis |
| MAGEA1 | Diseases associated with MAGEA1 include melanoma and hemangioma of liver, non-small cell lung cancer, gastric cancer and melanoma |
| MAGEA3 | Diseases associated with MAGEA3 include many cancers, including renal cell carcinoma, bladder carcinoma, melanoma, non-small cell lung cancer, hematologic malignancies, among others |
| MAGEA4 | Diseases associated with MAGEA4 include melanoma and testicular leukemia, thyroid cancer, breast cancer including estrogen receptor negative breast cancer and non-small cell lung cancer |
| MAGEC1 | Diseases associated with MAGEC1 include breast cancer, ovarian carcinoma and prostate cancer |
| MAGEC2 | Diseases associated with MAGEC2 include hepatocellular carcinoma, melanoma gastrointestinal stromal tumors, breast cancer metastasis and prostate cancer |
| SCGB2A2 | Diseases associated with SCGB2A2 include breast cancer |
| MLANA | Diseases associated with MLANA include melanoma |
| MDK | Diseases associated with MDK include multiple cancer types, including breast cancer, thyroid cancer, pancreatic cancer, neuroblastoma, glioblastoma, Wilms' tumors, thyroid papillary carcinomas, colorectal, liver, ovary, bladder, breast, lung, esophageal, stomach, and prostate cancers |
| MMP2 | Diseases associated with MMP2 include many forms of cancer, including bladder cancer, colorectal, melanoma, breast cancer, lung cancer, ovarian cancer, and prostate cancer |
| CTAG1B | Diseases associated with CTAG1B include many cancers, including breast cancer, thyroid cancer, ovarian cancer, melanomas, sarcomas, lung cancer, head and neck cancer, prostate cancer, and bladder cancer |
| ACPP | Diseases associated with ACPP include prostate cancer, ovarian cancer and prostatic adenoma |
| STEAP1 | Diseases associated with STEAP1 include prostate cancer |
| TAG1 | Diseases associated with TAG1 include brain cancer, breast cancer, colon cancer, lung cancer, ovary cancer, pharynx cancer, tongue cancer, bladder cancer (including urothelial carcinoma of the bladder) |
| TYR | Diseases associated with TYR include skin cancer and melanoma |

Thus, according to one embodiment, the invention relates to any one of the antigenic peptides and immunogenic compounds described herein, as well as to any one of the immunogenic compositions described herein, for use in the prevention or in the treatment of a cancer selected from Table 1B.

The invention further relates to a nucleic acid coding for an antigenic peptide having amino acid similarity with a tumor antigen, wherein the peptide is selected in the group consisting of:
    antigenic peptides selected in the group consisting of SEQ ID NO:1 to 106; and/or
    antigenic peptides of formula (I), or (Ia), or (Ib), as described herein.

In particular, the nucleic acid as defined above may code for an antigenic peptide selected in the group consisting of peptides having amino acid similarity with IL13RA2, which includes SEQ ID NO:71.

The invention also concerns a method for preventing or treating a cancer or initiating, enhancing or prolonging an anti-tumor-response in a subject in need thereof comprising administering to the subject an antigenic peptide according to the present invention or an immunogenic compound according to the present invention or an immunogenic composition according to the present invention or a nanoparticle according to the present invention or a nucleic acid according to the present invention or a combination according to the present invention.

Furthermore, the invention relates to a nucleic acid coding for an antigenic peptide or an immunogenic compound as above defined.

Furthermore, the present invention also relates to a combination of two distinct immunogenic compounds according to the present invention for use in the prevention and/or treatment of a cancer.

Furthermore, the present invention also relates to a combination of two distinct antigenic peptides according to the present invention for use in the prevention and/or treatment of a cancer.

Furthermore, the present invention also relates to a combination of two distinct nanoparticles according to the present invention for use in the prevention and/or treatment of a cancer.

Furthermore, the present invention also relates to a combination of two distinct nucleic acids according to the present invention for use in the prevention and/or treatment of a cancer.

In certain embodiments, the two distinct components of the combination for use according to the present invention are comprised in the same or distinct compositions.

In certain embodiments, the two distinct components of the combination for use according to the present invention are administered via the same or distinct routes of administration.

In certain embodiments, the two distinct components of the combination for use according to the present invention are administered at about the same time (simultaneously) or consecutively.

Furthermore, the present invention also relates to a kit comprising

- an immunogenic compound according to the present invention,
- an antigenic peptide according to the present invention,
- a (host) cell according to the present invention,
- a nanoparticle according to the present invention,
- a nucleic acid according to the present invention, or
- an immunogenic composition according to the present invention.

Antigenic Peptides, Immunogenic Compounds, Nucleic Acids, Nanoparticles and Cells Unless reference to the contrary, all the passages referring to «antigenic peptides» may also be applied to «immunogenic compounds».

Antigenic peptides according to the invention are listed in Table 1A below, which also provides information regarding the corresponding "reference" human tumor antigens (epitopes) with the name of the gene encoding them, and in a non-limitative manner their reported localization in tumors. N.A. =Not Available. The sequence IDs SEQ ID NO:1 to 106 refer to the antigenic peptide.

TABLE 1A

Antigenic peptides according to the invention

| SEQ ID NO: | Gene coding for antigen | Antigenic Peptide | Reference | Tumor localization |
|---|---|---|---|---|
| 1 | PLIN2 | SLAGTITGV | SVASTITGV (SEQ ID NO: 107) | adipocytes, macrophages |
| 2 | ALDH1A1 | LLMKLADLV | LLYKLADLI (SEQ ID NO: 108) | mucosa, keratinocytes |
| 3 | ALDH1A1 | LLYKIADLV | LLYKLADLI (SEQ ID NO: 108) | mucosa, keratinocytes |
| 4 | AFP | SLALSVILRV | QLAVSVILRV (SEQ ID NO: 109) | liver |
| 5 | AFP | SLAVSVILRA | QLAVSVILRV (SEQ ID NO: 109) | liver |
| 6 | PTPRC | KLLDAVISL | KFLDALISL (SEQ ID NO: 110) | proliferating cells, testis, multiple tissues (low level) |
| 7 | PTPRC | KLLDALLSL | KFLDALISL (SEQ ID NO: 110) | proliferating cells, testis, multiple tissues (low level) |
| 8 | PTPRC | KMLDALIDL | KFLDALISL (SEQ ID NO: 110) | proliferating cells, testis, multiple tissues (low level) |
| 9 | PTPRC | KILDSLISL | KFLDALISL (SEQ ID NO: 110) | proliferating cells, testis, multiple tissues (low level) |
| 10 | PTPRC | KFLDALIGV | KFLDALISL (SEQ ID NO: 110) | proliferating cells, testis, multiple tissues (low level) |
| 11 | PTPRC | KFLDSLISV | KFLDALISL (SEQ ID NO: 110) | proliferating cells, testis, multiple tissues (low level) |
| 12 | CEACAM5 | GVLAGVALV | GVLVGVALI (SEQ ID NO: 111) | gut carcinoma |
| 13 | CEACAM5 | GMLVGVALI | GVLVGVALI (SEQ ID NO: 111) | gut carcinoma |
| 14 | CEACAM5 | GLLMGVALI | GVLVGVALI (SEQ ID NO: 111) | gut carcinoma |
| 15 | CEACAM5 | GVLVGLALV | GVLVGVALI (SEQ ID NO: 111) | gut carcinoma |
| 16 | CEACAM5 | GVLAGIALI | GVLVGVALI (SEQ ID NO: 111) | gut carcinoma |

TABLE 1A-continued

Antigenic peptides according to the invention

| SEQ ID NO: | Gene coding for antigen | Antigenic Peptide | Reference | Tumor localization |
|---|---|---|---|---|
| 17 | CEACAM5 | GILVGVALV | GVLVGVALI (SEQ ID NO: 111) | gut carcinoma |
| 18 | CEACAM5 | GLLIGVALI | GVLVGVALI (SEQ ID NO: 111) | gut carcinoma |
| 19 | CEACAM5 | GVLLGVALV | GVLVGVALI (SEQ ID NO: 111) | gut carcinoma |
| 20 | CEACAM5 | GVLTGIALI | GVLVGVALI (SEQ ID NO: 111) | gut carcinoma |
| 21 | CEACAM5 | GILVGLALI | GVLVGVALI (SEQ ID NO: 111) | gut carcinoma |
| 22 | CEACAM5 | GVIVGVALV | GVLVGVALI (SEQ ID NO: 111) | gut carcinoma |
| 23 | CEACAM5 | GVFVGLALI | GVLVGVALI (SEQ ID NO: 111) | gut carcinoma |
| 24 | CEACAM5 | GVLIGVALV | GVLVGVALI (SEQ ID NO: 111) | gut carcinoma |
| 25 | CEACAM5 | YLFGHSWYK | HLFGYSWYK (SEQ ID NO: 112) | gut carcinoma |
| 26 | ENAH | TMNGKSSPV | TMNGSKSPV (SEQ ID NO: 113) | breast, prostate stroma and epithelium of colon-rectum, pancreas, endometrium |
| 27 | EZH2 | FMAEDETLL | FMVEDETVL (SEQ ID NO: 114) | ubiquitous (low level) |
| 28 | PMEL | ITSDVPFSV | ITDQVPFSV (SEQ ID NO: 115) | melanoma |
| 29 | ERBB2 | IMSAVIGIL | IISAVVGIL (SEQ ID NO: 116) | ubiquitous (low level) |
| 30 | ERBB2 | ILSAVIGIL | IISAVVGIL (SEQ ID NO: 116) | ubiquitous (low level) |
| 31 | ERBB2 | ILSAVVGVL | IISAVVGIL (SEQ ID NO: 116) | ubiquitous (low level) |
| 32 | ERBB2 | IMSAVVGIL | IISAVVGIL (SEQ ID NO: 116) | ubiquitous (low level) |
| 33 | ERBB2 | FISAVVGVL | IISAVVGIL (SEQ ID NO: 116) | ubiquitous (low level) |
| 34 | ERBB2 | ILSAVVGIL | IISAVVGIL (SEQ ID NO: 116) | ubiquitous (low level) |
| 35 | ERBB2 | IISAVIGIV | IISAVVGIL (SEQ ID NO: 116) | ubiquitous (low level) |
| 36 | ERBB2 | IISAIVGLL | IISAVVGIL (SEQ ID NO: 116) | ubiquitous (low level) |
| 37 | ERBB2 | IISAIVGIV | IISAVVGIL (SEQ ID NO: 116) | ubiquitous (low level) |
| 38 | ERBB2 | IISAVVGVV | IISAVVGIL (SEQ ID NO: 116) | ubiquitous (low level) |
| 39 | ERBB2 | IISAVVGIV | IISAVVGIL (SEQ ID NO: 116) | ubiquitous (low level) |

TABLE 1A-continued

Antigenic peptides according to the invention

| SEQ ID NO: | Gene coding for antigen | Antigenic Peptide | Reference | Tumor localization |
|---|---|---|---|---|
| 40 | ERBB2 | LISAVVGLL | IISAVVGIL (SEQ ID NO: 116) | ubiquitous (low level) |
| 41 | ERBB2 | ILYGGAYSL | ILHNGAYSL (SEQ ID NO: 117) | ubiquitous (low level) |
| 42 | ERBB2 | KLYGSLAFL | KIFGSLAFL (SEQ ID NO: 118) | ubiquitous (low level) |
| 43 | ERBB2 | KIFGTLAFM | KIFGSLAFL (SEQ ID NO: 118) | ubiquitous (low level) |
| 44 | ERBB2 | PLADIISAV | PLTSIISAV (SEQ ID NO: 119) | ubiquitous (low level) |
| 45 | ERBB2 | PLASIFSAV | PLTSIISAV (SEQ ID NO: 119) | ubiquitous (low level) |
| 46 | ERBB2 | PLSSILSAV | PLTSIISAV (SEQ ID NO: 119) | ubiquitous (low level) |
| 47 | ERBB2 | RLLEETDLV | RLLQETELV (SEQ ID NO: 120) | ubiquitous (low level) |
| 48 | ERBB2 | TLNDITGYL | TLEEITGYL (SEQ ID NO: 121) | ubiquitous (low level) |
| 49 | ERBB2 | TLEEITNFL | TLEEITGYL (SEQ ID NO: 121) | ubiquitous (low level) |
| 50 | ERBB2 | TVDEITGYL | TLEEITGYL (SEQ ID NO: 121) | ubiquitous (low level) |
| 51 | ERBB2 | VMLGVVFGV | VVLGVVFGI (SEQ ID NO: 122) | ubiquitous (low level) |
| 52 | ERBB2 | VLLGVVFGV | VVLGVVFGI (SEQ ID NO: 122) | ubiquitous (low level) |
| 53 | ERBB2 | MVLGVVFGV | VVLGVVFGI (SEQ ID NO: 122) | ubiquitous (low level) |
| 54 | ERBB2 | VMLGIVFGI | VVLGVVFGI (SEQ ID NO: 122) | ubiquitous (low level) |
| 55 | ERBB2 | VMLGVVFGI | VVLGVVFGI (SEQ ID NO: 122) | ubiquitous (low level) |
| 56 | ERBB2 | ILLGVVFGI | VVLGVVFGI (SEQ ID NO: 122) | ubiquitous (low level) |
| 57 | ERBB2 | VLLGVIFGI | VVLGVVFGI (SEQ ID NO: 122) | ubiquitous (low level) |
| 58 | ERBB2 | VLFGVVFGI | VVLGVVFGI (SEQ ID NO: 122) | ubiquitous (low level) |
| 59 | ERBB2 | IVLGVVFGV | VVLGVVFGI (SEQ ID NO: 122) | ubiquitous (low level) |
| 60 | ERBB2 | VVLGVLFGV | VVLGVVFGI (SEQ ID NO: 122) | ubiquitous (low level) |
| 61 | ERBB2 | VVLGVMFGV | VVLGVVFGI (SEQ ID NO: 122) | ubiquitous (low level) |
| 62 | ERBB2 | VVLGVIFGV | VVLGVVFGI (SEQ ID NO: 122) | ubiquitous (low level) |
| 63 | ERBB2 | VVLGAVFGV | VVLGVVFGI (SEQ ID NO: 122) | ubiquitous (low level) |

TABLE 1A-continued

Antigenic peptides according to the invention

| SEQ ID NO: | Gene coding for antigen | Antigenic Peptide | Reference | Tumor localization |
|---|---|---|---|---|
| 64 | ERBB2 | VVLGLVFGV | VVLGVVFGI (SEQ ID NO: 122) | ubiquitous (low level) |
| 65 | ERBB2 | VVIGVVFGV | VVLGVVFGI (SEQ ID NO: 122) | ubiquitous (low level) |
| 66 | ERBB2 | VVLGIVFGV | VVLGVVFGI (SEQ ID NO: 122) | ubiquitous (low level) |
| 67 | ERBB2 | TVLGVVFGV | VVLGVVFGI (SEQ ID NO: 122) | ubiquitous (low level) |
| 68 | ERBB2 | VVLGVVFGV | VVLGVVFGI (SEQ ID NO: 122) | ubiquitous (low level) |
| 69 | ERBB2 | AILGVVFGI | VVLGVVFGI (SEQ ID NO: 122) | ubiquitous (low level) |
| 70 | ERBB2 | AVLGVMFGI | VVLGVVFGI (SEQ ID NO: 122) | ubiquitous (low level) |
| 71 | IL13RA2 | FLPFGFILV | WLPFGFILI (SEQ ID NO: 123) | NA |
| 72 | MAGEA1 | KMLHYVIKV | KVLEYVIKV (SEQ ID NO: 124) | NA |
| 73 | MAGEA3 | EMNPIGHLY | EVDPIGHLY (SEQ ID NO: 125) | NA |
| 74 | MAGEA3 | RVDPIGNLY | EVDPIGHLY (SEQ ID NO: 125) | NA |
| 75 | MAGEA3 | VTELVNFLL | VAELVHFLL (SEQ ID NO: 126) | NA |
| 76 | MAGEA4 | HVDPATNTY | EVDPASNTY (SEQ ID NO: 127) | NA |
| 77 | MAGEC1 | KLVEWLAML | KVVEFLAML (SEQ ID NO: 128) | NA |
| 78 | MAGEC1 | SLSYALLSL | SFSYTLLSL (SEQ ID NO: 129) | NA |
| 79 | MAGEC1 | SISHTLLSL | SFSYTLLSL (SEQ ID NO: 129) | NA |
| 80 | MAGEC1 | VSSFFSYVF | VSSFFSYTL (SEQ ID NO: 130) | NA |
| 81 | MAGEC2 | ALNDVEEKV | ALKDVEERV (SEQ ID NO: 131) | NA |
| 82 | MAGEC2 | ALSDVEDRV | ALKDVEERV (SEQ ID NO: 131) | NA |
| 83 | MAGEC2 | ALSDAEERV | ALKDVEERV (SEQ ID NO: 131) | NA |
| 84 | MAGEC2 | ATSTLMLVF | ASSTLYLVF (SEQ ID NO: 132) | NA |
| 85 | MAGEC2 | TTSTLYLVF | ASSTLYLVF (SEQ ID NO: 132) | NA |
| 86 | SCGB2A2 | PLFESVISK | PLLENVISK (SEQ ID NO: 133) | breast cancer |
| 87 | SCGB2A2 | PLLETTISK | PLLENVISK (SEQ ID NO: 133) | breast cancer |

TABLE 1A-continued

Antigenic peptides according to the invention

| SEQ ID NO: | Gene coding for antigen | Antigenic Peptide | Reference | Tumor localization |
|---|---|---|---|---|
| 88 | MLANA | ILTAILGVL | ILTVILGVL (SEQ ID NO: 134) | melanoma |
| 89 | MLANA | ILTVILGVV | ILTVILGVL (SEQ ID NO: 134) | melanoma |
| 90 | MDK | ALFAVTSAV | ALLALTSAV (SEQ ID NO: 135) | ubiquitous (low level) |
| 91 | MDK | ALFALTSAA | ALLALTSAV (SEQ ID NO: 135) | ubiquitous (low level) |
| 92 | MMP2 | SLPPDVQEV | GLPPDVQRV (SEQ ID NO: 136) | ubiquitous |
| 93 | MMP2 | SLPPDVQQV | GLPPDVQRV (SEQ ID NO: 136) | ubiquitous |
| 94 | CTAG1B | VAMPFATPV | LAMPFATPM (SEQ ID NO: 137) | NA |
| 95 | ACPP | ALDVYSALL | ALDVYNGLL (SEQ ID NO: 138) | prostate cancer |
| 96 | ACPP | ALDMYNALL | ALDVYNGLL (SEQ ID NO: 138) | prostate cancer |
| 97 | ACPP | ALDIYNSLL | ALDVYNGLL (SEQ ID NO: 138) | prostate cancer |
| 98 | ACPP | FLFFLFFFL | FLFLLFFWL (SEQ ID NO: 139) | prostate cancer |
| 99 | ACPP | TLMSSMTNM | TLMSAMTNL (SEQ ID NO: 140) | prostate cancer |
| 100 | STEAP1 | MLAVFLPMV | MIAVFLPIV (SEQ ID NO: 141) | prostate cancer |
| 101 | STEAP1 | MLAVFLPLV | MIAVFLPIV (SEQ ID NO: 141) | prostate cancer |
| 102 | STEAP1 | YLAVFLPIV | MIAVFLPIV (SEQ ID NO: 141) | prostate cancer |
| 103 | TAG1 | SLGYLFLLM | SLGWLFLLL (SEQ ID NO: 142) | NA |
| 104 | TAG1 | SLGFLFLLM | SLGWLFLLL (SEQ ID NO: 142) | NA |
| 105 | TAG1 | SLGFLFLLF | SLGWLFLLL (SEQ ID NO: 142) | NA |
| 106 | TYR | MLFAVLMCL | MLLAVLYCL (SEQ ID NO: 143) | melanoma |

Those 106 antigenic peptide sequences can be further defined based on the sequence of the reference tumor antigen, such as a tumor antigen derived from IL13RA2.

Thus, the invention relates to an immunogenic compound comprising an antigenic peptide having amino acid similarity with a tumor antigen, which antigenic peptide is selected in the group consisting of SEQ ID NO:1-106, which includes:

peptides having amino acid similarity with the tumor antigen encoded by gene PLIN2, the said antigenic peptide being selected in the group consisting of SEQ ID NO:1;

peptides having amino acid similarity with the tumor antigen encoded by gene ALDHIA1, the said antigenic peptide being selected in the group consisting of SEQ ID NO: 2-3;

peptides having amino acid similarity with the tumor antigen encoded by gene AFP, the said antigenic peptide being selected in the group consisting of SEQ ID NO:4-5;

peptides having amino acid similarity with the tumor antigen encoded by gene PTPRC, the said antigenic peptide being selected in the group consisting of SEQ ID NO:6-11;

peptides having amino acid similarity with the tumor antigen encoded by gene CEACAM5, the said antigenic peptide being selected in the group consisting of SEQ ID NO: 12-25;

peptides having amino acid similarity with the tumor antigen encoded by gene ENAH, the said antigenic peptide being selected in the group consisting of SEQ ID NO:26;

peptides having amino acid similarity with the tumor antigen encoded by gene EZH2, the said antigenic peptide being selected in the group consisting of SEQ ID NO:27;

peptides having amino acid similarity with the tumor antigen encoded by gene PMEL, the said antigenic peptide being selected in the group consisting of SEQ ID NO:28;

peptides having amino acid similarity with the tumor antigen encoded by gene ERBB2, the said antigenic peptide being selected in the group consisting of SEQ ID NO: 29-70;

peptides having amino acid similarity with the tumor antigen encoded by gene IL13RA2, the said antigenic peptide being selected in the group consisting of SEQ ID NO: 71;

peptides having amino acid similarity with the tumor antigen encoded by gene MAGEA1, the said antigenic peptide being selected in the group consisting of SEQ ID NO: 72;

peptides having amino acid similarity with the tumor antigen encoded by gene MAGEA3, the said antigenic peptide being selected in the group consisting of SEQ ID NO: 73-75;

peptides having amino acid similarity with the tumor antigen encoded by gene MAGEA4, the said antigenic peptide being selected in the group consisting of SEQ ID NO: 76;

peptides having amino acid similarity with the tumor antigen encoded by gene MAGEC1, the said antigenic peptide being selected in the group consisting of SEQ ID NO: 77-80;

peptides having amino acid similarity with the tumor antigen encoded by gene MAGEC2, the said antigenic peptide being selected in the group consisting of SEQ ID NO: 81-85;

peptides having amino acid similarity with the tumor antigen encoded by gene SCGB2A2, the said antigenic peptide being selected in the group consisting of SEQ ID NO: 86-87;

peptides having amino acid similarity with the tumor antigen encoded by gene MLANA, the said antigenic peptide being selected in the group consisting of SEQ ID NO: 88-89;

peptides having amino acid similarity with the tumor antigen encoded by gene MDK, the said antigenic peptide being selected in the group consisting of SEQ ID NO:90-91;

peptides having amino acid similarity with the tumor antigen encoded by gene MMP2, the said antigenic peptide being selected in the group consisting of SEQ ID NO: 92-93;

peptides having amino acid similarity with the tumor antigen encoded by gene CTAG1B, the said antigenic peptide being selected in the group consisting of SEQ ID NO: 94;

peptides having amino acid similarity with the tumor antigen encoded by gene ACPP, the said antigenic peptide being selected in the group consisting of SEQ ID NO:95-99;

peptides having amino acid similarity with the tumor antigen encoded by gene STEAP1, the said antigenic peptide being selected in the group consisting of SEQ ID NO: 100-102;

peptides having amino acid similarity with the tumor antigen encoded by gene TAG1, the said antigenic peptide being selected in the group consisting of SEQ ID NO: 103-105;

peptides having amino acid similarity with the tumor antigen encoded by gene TYR, the said antigenic peptide being selected in the group consisting of SEQ ID NO:106.

Accordingly, those 106 antigenic peptides may be further categorized in a plurality of distinct families according to their reference peptide:

Family «SVASTITGV» SEQ ID NO:107), which family includes the amino acid sequences of SEQ ID NO:1;

Family «LLYKLADLI» (SEQ ID NO:108) which family includes the amino acid sequences of SEQ ID NO:2-3;

Family «QLAVSVILRV» (SEQ ID NO:109) which family includes the amino acid sequences of SEQ ID NO:4-5;

Family «KFLDALISL» (SEQ ID NO:110) which family includes the amino acid sequences of SEQ ID NO:6-11;

Family «GVLVGVALI» (SEQ ID NO:111) which family includes the amino acid sequences of SEQ ID NO: 12-24;

Family «HLFGYSWYK» (SEQ ID NO:112) which family includes the amino acid sequences of SEQ ID NO:25;

Family «TMNGSKSPV» (SEQ ID NO:113) which family includes the amino acid sequences of SEQ ID NO:26;

Family «FMVEDETVL» (SEQ ID NO:114) which family includes the amino acid sequences of SEQ ID NO:27;

Family «ITDQVPFSV» (SEQ ID NO:115) which family includes the amino acid sequences of SEQ ID NO:28;

Family «IISAVVGIL» (SEQ ID NO: 116) which family includes the amino acid sequences of SEQ ID NO:29-40;

Family «ILHNGAYSL» SEQ ID NO:117) which family includes the amino acid sequences of SEQ ID NO:41;

Family «KIFGSLAFL» (SEQ ID NO:118) which family includes the amino acid sequences of SEQ ID NO:42-43;

Family «PLTSIISAV» (SEQ ID NO:119) which family includes the amino acid sequences of SEQ ID NO:44-46;

Family «RLLQETELV» (SEQ ID NO:120) which family includes the amino acid sequences of SEQ ID NO:47;

Family «TLEEITGYL» (SEQ ID NO:121) which family includes the amino acid sequences of SEQ ID NO:48-50;

Family «VVLGVVFGI» SEQ ID NO:122) which family includes the amino acid sequences of SEQ ID NO:51-70;

Family «WLPFGFILI» (SEQ ID NO:123) including sequence SEQ ID NO:71;

Family «KVLEYVIKV» (SEQ ID NO:124) which family includes the amino acid sequences of SEQ ID NO:72;

Family «EVDPIGHLY» (SEQ ID NO:125) which family includes the amino acid sequences of SEQ ID NO:73-74;

Family «VAELVHFLL» (SEQ ID NO:126) which family includes the amino acid sequences of SEQ ID NO:75;
Family «EVDPASNTY» SEQ ID NO:127) which family includes the amino acid sequences of SEQ ID NO:76;
Family «KVVEFLAML» (SEQ ID NO:128) which family includes the amino acid sequences of SEQ ID NO:77;
Family «SFSYTLLSL» (SEQ ID NO:129) which family includes the amino acid sequences of SEQ ID NO:78-79;
Family «VSSFFSYTL» (SEQ ID NO:130) which family includes the amino acid sequences of SEQ ID NO:80;
Family «ALKDVEERV» (SEQ ID NO:131) which family includes the amino acid sequences of SEQ ID NO:81-83;
Family «ASSTLYLVF» (SEQ ID NO:132) which family includes the amino acid sequences of SEQ ID NO:84-85;
Family «PLLENVISK» (SEQ ID NO:133) which family includes the amino acid sequences of SEQ ID NO:86-87;
Family «ILTVILGVL» (SEQ ID NO:134) which family includes the amino acid sequences of SEQ ID NO:88-89;
Family «ALLALTSAV» (SEQ ID NO:135) which family includes the amino acid sequences of SEQ ID NO:90-91;
Family «GLPPDVQRV» (SEQ ID NO:136) which family includes the amino acid sequences of SEQ ID NO:92-93;
Family «LAMPFATPM» (SEQ ID NO:137) which family includes the amino acid sequences of SEQ ID NO:94;
Family «ALDVYNGLL» (SEQ ID NO:138) which family includes the amino acid sequences of SEQ ID NO:95-97;
Family «FLFLLFFWL» (SEQ ID NO:139) which family includes the amino acid sequences of SEQ ID NO:98;
Family «TLMSAMTNL» (SEQ ID NO:140) which family includes the amino acid sequences of SEQ ID NO:99;
Family «MIAVFLPIV» (SEQ ID NO:141) which family includes the amino acid sequences of SEQ ID NO:100-102;
Family «SLGWLFLLL» (SEQ ID NO:142) which family includes the amino acid sequences of SEQ ID NO:103-105;
Family «MLLAVLYCL» (SEQ ID NO:143) which family includes the amino acid sequences of SEQ ID NO:106.

According to a preferred embodiment, an antigenic peptide of the invention is selected from the group consisting of peptides or polypeptides comprising, or consisting of, the amino acid sequence SEQ ID NO:71.

According to an exemplified embodiment, the antigenic peptide of the invention is a peptide or polypeptide comprising, or consisting of, the amino acid sequence of SEQ ID NO:71.

More preferably, the antigenic peptide of the invention is selected from the group consisting of peptides or polypeptides comprising or consisting of an amino acid sequence according to any one of SEQ ID NOs: 17, 31, 32, 51, 52, 55, 56, 59, 68, 89, 94, 100, 101 or 102. It is also more preferred that the antigenic peptide of the invention is selected from the group consisting of peptides or polypeptides comprising or consisting of an amino acid sequence according to any one of SEQ ID NOs: 26, 28, 47, 51, 52, 55, 56, 77, 93, 101 or 102. Even more preferably, the antigenic peptide of the invention is selected from the group consisting of peptides or polypeptides comprising or consisting of an amino acid sequence according to any one of SEQ ID NOs: 51, 52, 55, 56, 101 or 102. Still more preferably, the antigenic peptide of the invention is selected from the group consisting of peptides or polypeptides comprising or consisting of an amino acid sequence according to any one of SEQ ID NOs: 51, 52, 55 or 56. It is also still more preferred that the antigenic peptide of the invention is selected from the group consisting of peptides or polypeptides comprising or consisting of an amino acid sequence according to any one of SEQ ID NOs: 101 or 102.

According to some embodiments, the immunogenic compound comprises, or consists of, an antigenic peptide of formula (I):

PepNt-CORE-PepCt(I), wherein:

"PepNt" consists of a polypeptide having an amino acid length varying from 0 to 500 amino acid residues and located at the N-terminal end of the polypeptide of formula (I);

CORE consists of a polypeptide comprising, or alternatively consisting of, an amino acid sequence selected from the group consisting of SEQ ID NO:1 to 106 (which includes SEQ ID NO:71), in particular an amino acid sequence as set forth in any one of SEQ ID NOs: 26, 28, 47, 51, 52, 55, 56, 77, 93, 101 or 102 or an amino acid sequence as set forth in any one of 17, 31, 32, 51, 52, 55, 56, 59, 68, 89, 94, 100, 101 or 102, such as an amino acid sequence as set forth in any one of SEQ ID NOs: 51, 52, 55, 56, 101 or 102; and "PepCt" consists of a polypeptide having an amino acid length varying from 0 to 500 amino acid residues and located at the C-terminal end of the polypeptide of formula (I).

According to one particular embodiment, the immunogenic compound comprises or consists of an antigenic peptide of formula (Ia) or (Ib):

PepNt-CORE(Ia); or

CORE-PepCt(Ib).

wherein "PepNt" and "PepCt" and CORE are as defined above.

According to some even more particular embodiments, the antigenic peptide or immunogenic above, as defined above, comprises from 9 to 1000 amino acids; which includes 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67? 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900 and 1000 amino acids.

According to said embodiment, the length of "PepNt" and "PepCt", if applicable, are defined accordingly.

Thus, "PepNt" and "PepCt", as defined above, may comprise from 0 to 500 amino acid residues; which includes 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, and 500 amino acid residues.

The types of carrier molecules used for generating an immunogenic compound of the invention, such as the ones comprising or consisting of a peptide of formula (I) linked to a carrier molecule, are well in the general knowledge of the one skilled in the art. The function of the carrier molecule is to provide cytokine help (or T-cell help) in order to enhance the immune response against tumor antigen.

Preferably, the antigenic peptide is linked to a carrier molecule, in particular to a carrier protein, preferably by covalent or non-covalent bond. The carrier molecule to which the peptide is optionally bound can be selected from a wide variety of known carriers. Examples of carrier molecules for vaccine purposes encompass proteins such as human or bovine serum albumin and keyhole limpet haemocyanin (KLH) and fatty acids. Other embodiments of carrier molecules to which an antigenic peptide of formula (I) may be covalently linked include bacterial toxins or toxoids, such as diphtheria, cholera, E. coli heat labile or tetanus toxoids, the N. meningitidis outer membrane protein (European patent application n° EP0372501), synthetic peptides (European patent applications n° EP0378881 and n° EP0427347), heat shock proteins (PCT application n° WO93/17712), Pertussis proteins (PCT application n° WO98/58668), protein D from H. influenzae (PCT application n° WO00/56360.) and toxin A or B from C. difficile (International patent application WO00/61761).

According to one embodiment, the carrier protein or carrier peptide is a HHD-DR3 carrier peptide MAKTIAYDEEARRGLERGLN (SEQ ID NO:144).

According to one embodiment, "PepNt" and/or "PepCt" may correspond to a carrier protein or carrier peptide, such as the HHD-DR3 carrier peptide MAKTIAYDEEARRGLERGLN (SEQ ID NO:144).

According to one embodiment, the immunogenic compound comprises or consists of the carrier peptide of sequence SEQ ID NO:144 linked covalently to the N-terminus of the antigenic peptide of sequence SEQ ID NO:71.

More preferably, the carrier protein or carrier peptide is a protein/peptide having immuno-adjuvant properties, such as providing stimulation of CD4+Th1 cells as described herein. A preferred example thereof is a non-tumor antigen that recalls immune memory or provides a non-specific help or could be a specific tumor-derived helper peptide, such as tetanus helper peptide, keyhole limpet hemocyanin peptide or PADRE peptide. Another preferred example is a specific tumor derived helper peptide, which may be presented by MHC II, in particular by HLA-DR, HLA-DP or HLA-DQ, such as fragments of shared overexpressed tumor antigens, e.g. HER2, NY-ESO-1, hTERT or IL13RA2, as described above.

Accordingly, "PepNt" and/or "PepCt" may preferably correspond to such a protein/peptide having immuno-adjuvant properties, such as providing stimulation of CD4+Th1 cells as described herein.

Moreover, the immunogenic compound comprises or consists of such a protein/peptide having immuno-adjuvant properties, such as providing stimulation of CD4+Th1 cells as described herein, linked covalently to the N-terminus of the antigenic peptide having an amino acid sequence selected from the group consisting of SEQ ID NO: 1 to 106 (which includes SEQ ID NO:71), in particular an amino acid sequence as set forth in any one of SEQ ID NOs: 26, 28, 47, 51, 52, 55, 56, 77, 93, 101 or 102 or an amino acid sequence as set forth in any one of 17, 31, 32, 51, 52, 55, 56, 59, 68, 89, 94, 100, 101 or 102, such as an amino acid sequence as set forth in any one of SEQ ID NOs: 51, 52, 55, 56, 101 or 102.

According to one embodiment, the said antigenic peptide is covalently bound to the carrier molecule through a linker moiety.

The said restricted family of linker agents encompasses, or even consists of, the linker agents named GMBS, sulfo-GMBS, SMPB and sulfo-SMPB.

In some embodiments of an immunogenic compound as defined above, the said linker agent is selected form the group consisting of GMBS (N-[γ-maleimidobutyryl-oxy]succinimide ester), Sulfo-GMBS (N-[γ-maleimidobutyryl-oxy]sulfosuccinimide ester), SMPB (succinimidyl 4-[p-maleimidophenyl]butyrate) and Sulfo-SMPB (sulfosuccinimidyl 4-[p-maleimidophenyl]butyrate).

Methods for conjugating two proteins with a linker agent in general, and more particularly with a linker agent selected from the group consisting of GMBS, Sulfo-GMBS, SMPB and Sulfo-SMPB, are well known by the one skilled in the art. Illustratively, such protocols are disclosed in the leaflets that are made publicly available by the Pierce Company (Illinois, USA). GMBS, Sulfo-GMBS, SMPB and Sulfo-SMPB consist of heterobifunctional linker agents that contain both a N-hydroxysuccinimide (NHS) ester group and a maleimide group. Conjugation using GMBS, Sulfo-GMBS, SMPB or Sulfo-SMPB is usually performed by a two-step procedure. In a first step, the amine-containing protein is reacted with a several-fold molar excess of the linker agent at pH 7-9 to form amide bonds, followed by removal of excess non-reacted linker agent, usually by desalting or dialysis. In a second step, the sulfhydryl-containing molecule (e.g. peptide of formula (I)) is added to react with the maleimide groups already attached to the first protein at pH 6.5-7.5 to form stable thioether bonds.

Using SMPB or Sulfo-SMPB as linker agents for covalently linking peptides of formula (I) to the amine-containing carrier protein, leads to a conjugate of formula (II) below:

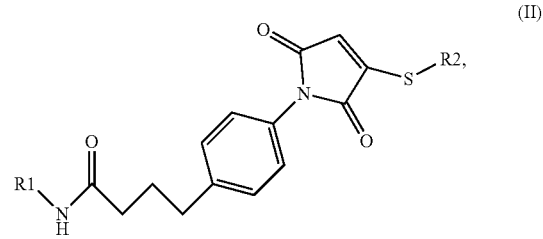

(II)

wherein:
R1 consists of one reactive group of the amine-containing carrier protein, and wherein the NH group attached thereto derives from (i) the alpha amino group located at the N-terminal end of the amine-containing carrier protein or (ii) a lateral chain amino group from a Lysine (K) amino acid residue of the amine-containing carrier protein.

R2 consists of a peptide of formula (I), and wherein the sulphur(S) atom attached thereto derives from a sulfhydryl (SH) group of a cysteine residue located at the N-terminal end or at the C-terminal end of a peptide of formula (I). In some embodiments, the sulfhydryl moiety could be part of an unnatural amino acid, or any other molecule present at the end of the peptide of formula (I).

Using GMBS or Sulfo-GMBS as linker agents for covalently linking peptides of formula (I) to the amine-containing carrier protein, in particular the CRM197 carrier, protein leads to a conjugate of formula (III) below:

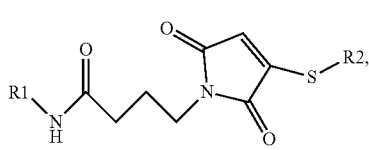

(III)

wherein:
R1 consists of one reactive group of the amine-containing carrier protein, and wherein the NH group attached thereto derives from (i) the alpha amino group located at the N-terminal end of the amine-containing carrier proteinor (ii) a lateral chain amino group from a Lysine (K) amino acid residue of the amine-containing carrier protein.
R2 consists of a peptide of formula (I), and wherein the sulphur(S) atom attached thereto derives from a sulfhydryl (SH) group of a cysteine residue located at the N-terminal end or at the C-terminal end of a peptide of formula (I). In some embodiments, the sulfhydryl moiety could be part of an unnatural amino acid, or any other molecule present at the end of the peptide of formula (I).

In a further aspect the present invention provides a cell loaded with at least one immunogenic compound according to the present invention or with at least one antigenic peptide according to the present invention. A preferred antigenic peptide is a peptide or polypeptide having an amino acid sequence as set forth in in any one of SEQ ID NOs: 26, 28, 47, 51, 52, 55, 56, 77, 93, 101 or 102 or an amino acid sequence as set forth in any one of 17, 31, 32, 51, 52, 55, 56, 59, 68, 89, 94, 100, 101 or 102, such as an amino acid sequence as set forth in any one of SEQ ID NOs: 51, 52, 55, 56, 101 or 102. Also combinations thereof are preferred, namely, cells loaded with distinct antigenic peptides according to the present invention (or with the respective immunogenic compound(s)).

A preferred cell is an antigen presenting cell (APC), more preferably a dendritic cell (DC).

Antigen-presenting cells (APCs) are of particular interest, as their main function is to process antigens and present it on the cell surface to the T cells of the immune system, so as to initiate and modulate T-cell responses in vivo. In the context of the present invention, it is preferred that the APCs are loaded with the antigenic peptide(s) and/or immunogenic compound(s) according to the invention, which can be done by exposing APCs in vitro with said antigenic peptide(s) and/or immunogenic compound(s) (Rizzo M M, Alaniz L, Mazzolini G.Ex vivo loading of autologous dendritic cells with tumor antigens. Methods Mol Biol. 2014; 1139:41-4; Rolinski J, Hus I. Breaking immunotolerance of tumors: a new perspective for dendritic cell therapy. J Immunotoxicol. 2014 October; 11 (4): 311-8).

Preferred antigen-presenting cells according to the invention are dendritic cells (DCs). It can indeed be advantageous to combine at least one antigenic peptide or immunogenic compound according to the invention with dendritic cells, as those are the most potent antigen-presenting cells and have been reported to be frequently functionally defective in cancer patients. Dendritic cells can be easily obtained by the skilled person in the art from either healthy compatible donors (i.e. the dendritic cells are HLA-related) or from the patient himself provided that they are functional (i.e. the dendritic cells are autologous), for example by direct isolation from the peripheral blood, or by derivation from peripheral blood cells such as CD14+ monocytes or CD34+ hematopoietic precursors (Figdor C G, de Vries I J, Lesterhuis W J, Melief C J. Dendritic cell immunotherapy: mapping the way. Nat Med. 2004 May; 10 (5): 475-80). Dendritic cells can indeed be distinguished from other cells of peripheral blood by their surface markers, such as S100, p55, CD83, and/or OX62, and may thus be isolated and purified based on said markers using cell cultures techniques well-known in the art.

In a further aspect, the present invention provides a nucleic acid encoding an antigenic peptide according to the present invention or an immunogenic compound according to the present invention, wherein the immunogenic compound is a peptide or a protein. Preferably, the antigenic peptide is a peptide or polypeptide having an amino acid sequence as set forth in in any one of SEQ ID NOs: 26, 28, 47, 51, 52, 55, 56, 77, 93, 101 or 102 or an amino acid sequence as set forth in any one of 17, 31, 32, 51, 52, 55, 56, 59, 68, 89, 94, 100, 101 or 102, such as an amino acid sequence as set forth in any one of SEQ ID NOs: 51, 52, 55, 56, 101 or 102; and/or an antigenic peptide of formula (I) as described above.

Nucleic acids preferably comprise single stranded, double stranded or partially double stranded nucleic acids, preferably selected from genomic DNA, cDNA, RNA, antisense DNA, antisense RNA, complementary RNA/DNA sequences with or without expression elements, a mini-gene, gene fragments, regulatory elements, promoters, and combinations thereof. Further preferred examples of nucleic acid (molecules) and/or polynucleotides include, e.g., a recombinant polynucleotide, a vector, an oligonucleotide, an RNA molecule such as an rRNA, an mRNA, or a tRNA, or a DNA molecule as described above. It is thus preferred that the nucleic acid (molecule) is a DNA molecule or an RNA molecule; preferably selected from genomic DNA; cDNA; rRNA; mRNA; antisense DNA; antisense RNA; complementary RNA and/or DNA sequences; RNA and/or DNA sequences with or without expression elements, regulatory elements, and/or promoters; a vector; and combinations thereof.

Accordingly, the nucleic acid molecule may be a vector. The term "vector", as used in the context of the present invention, refers to a nucleic acid molecule, preferably to an artificial nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired antigenic peptide according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector that is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector. Preferably, a vector in the context of the present application is an expression vector. A preferred vector is a vector for expression in bacterial cells. More preferably, the vector is useful for expression in so-called "live bacterial vaccine vectors", wherein live bacterial cells (such as bacteria or bacterial spores, e.g., endospores, exospores or microbial cysts) can serve as vaccines. Preferred examples thereof are described in da Silva et al., Live bacterial vaccine vectors: an overview; Braz J Microbiol. 2015 Mar. 4;45 (4): 1117-29.

Nucleic acids encoding antigenic peptides according to the invention may be in the form of naked nucleic acids, or nucleic acids cloned into plasmids or viral vectors (Tregoning and Kinnear, Using Plasmids as DNA Vaccines for Infectious Diseases. Microbiol Spectr. 2014 December;2 (6). doi: 10.1128/microbiolspec.PLAS-0028-2014), the latter being particularly preferred. Examples of suitable viral vectors according to the invention include, without limitation, retrovirus, adenovirus, adeno-associated virus (AAV), herpes virus and poxvirus vectors. It is within the skill of the person in the art to clone a nucleic acid into a plasmid or viral vector, using standard recombinant techniques in the art.

In a further aspect, the present invention also provides a host cell comprising the nucleic acid according to the present invention, wherein the nucleic acid is preferably a vector. Preferably, the host cell is a bacterial cell. Such a host cell may be preferably used for production of the antigenic peptide according to the present invention or the immunogenic compound according to the present invention. Moreover, such a host cell may also be an active component in a vaccine.

Preferably, the host cell is a bacterial cell, preferably a gut bacterial cell. Such a bacterial host cell may serve as "live bacterial vaccine vector", wherein live bacterial cells (such as bacteria or bacterial spores, e.g., endospores, exospores or microbial cysts) can serve as vaccines. Preferred examples thereof are described in da Silva et al., Live bacterial vaccine vectors: an overview; Braz J Microbiol. 2015 Mar. 4;45 (4): 1117-29.

Bacterial cells (such as bacteria or bacterial spores, e.g., endospores, exospores or microbial cysts), in particular (entire) gut bacterial species, can be advantageous, as they have the potential to trigger a greater immune response than the (poly)peptides or nucleic acids they contain.

Alternatively, bacterial cells, in particular gut bacteria, according to the invention may be in the form of probiotics, i.e. of live gut bacterium, which can thus be used as food additive due to the health benefits it can provide. Those can be, for example, lyophilized in granules, pills or capsules, or directly mixed with dairy products for consumption.

In a further aspect, the present invention provides a nanoparticle loaded with
  at least one of the immunogenic compounds according to the present invention, or
  at least one of the antigenic peptides according to the present invention; and, optionally, with an adjuvant.

Nanoparticles, in particular for use as vaccines, are known in the art and described, for example, in Shao et al., Nanoparticle-based immunotherapy for cancer, ACS Nano 2015, 9 (1): 16-30; Zhao et al., Nanoparticle vaccines, Vaccine 2014, 32 (3): 327-37; and Gregory et al., Vaccine delivery using nanoparticles, Front Cell Infect Microbiol. 2013, 3:13, doi: 10.3389/fcimb.2013.00013. eCollection 2013, Review. In particular, the nanoparticle is used for delivery of the antigenic peptide (or the polypeptide/protein/nucleic acid comprising the antigenic peptide) and may optionally also act as an adjuvant. The antigenic peptide (the polypeptide/protein/nucleic acid comprising the antigenic peptide) is typically either encapsulated within the nanoparticle or linked/bound to (decorated onto) the surface of the nanoparticle ("coating"). Compared to conventional approaches, nanoparticles can protect the payload (antigen/adjuvant) from the surrounding biological milieu, increase the half-life, minimize the systemic toxicity, promote the delivery to APCs, or even directly trigger the activation of TAA-specific T-cells. Preferably, the nanoparticle has a size (diameter) of no more than 300 nm, more preferably of no more than 200 nm and most preferably of no more than 100 nm. Such nanoparticles are adequately sheltered from phagocyte uptake, with high structural integrity in the circulation and long circulation times, capable of accumulating at sites of tumor growth, and able to penetrate deep into the tumor mass.

Examples of nanoparticles include polymeric nanoparticles such as poly(ethylene glycol) (PEG) and poly(D,L-lactic-coglycolic acid) (PLGA); inorganic nanoparticles such as gold nanoparticles, iron oxide beads, iron-oxide zinc-oxide nanoparticles, carbon nanotubes and mesoporous silica nanoparticles; liposomes, such as cationic liposomes; immunostimulating complexes (ISCOM); virus-like particles (VLP); and self-assembled proteins.

Polymeric nanoparticles are nanoparticles based on/comprising polymers, such as poly(d,l-lactide-co-glycolide) (PLG), poly(d,l-lactic-coglycolic acid) (PLGA), poly(g-glutamic acid) (g-PGA), poly(ethylene glycol) (PEG), and polystyrene. Polymeric nanoparticles may entrap an antigen (e.g., the antigenic peptide or a (poly)peptide comprising the same) or bind to/conjugate to an antigen (e.g., the antigenic peptide or a (poly)peptide comprising the same). Polymeric nanoparticles may be used for delivery, e.g. to certain cells, or sustain antigen release by virtue of their slow biodegradation rate. For example, g-PGA nanoparticles may be used to encapsulate hydrophobic antigens. Polystyrene nanoparticles can conjugate to a variety of antigens as they can be surface-modified with various functional groups. Polymers, such as Poly(L-lactic acid) (PLA), PLGA, PEG, and natural polymers such as polysaccharides may also be used to synthesize hydrogel nanoparticles, which are a type of nano-sized hydrophilic three-dimensional polymer network. Nanogels have favorable properties including flexible mesh size, large surface area for multivalent conjugation, high water content, and high loading capacity for antigens. Accordingly, a preferred nanoparticle is a nanogel, such as a chitosan nanogel. Preferred polymeric nanoparticles are nanoparticles based on/comprising poly(ethylene glycol) (PEG) and poly(D,L-lactic-coglycolic acid) (PLGA).

Inorganic nanoparticles are nanoparticles based on/comprising inorganic substances, and examples of such nanoparticles include gold nanoparticles, iron oxide beads, iron-oxide zinc-oxide nanoparticles, carbon nanoparticles (e.g., carbon nanotubes) and mesoporous silica nanoparticles. Inorganic nanoparticles provide a rigid structure and controllable synthesis. For example, gold nanoparticles can be easily produced in different shapes, such as spheres, rods, cubes. Inorganic nanoparticles may be surface-modified, e.g. with carbohydrates. Carbon nanoparticles provide good biocompatibility and may be produced, for example, as nanotubes or (mesoporous) spheres. For example, multiple copies of the antigenic peptide according to the present invention (or a (poly)peptide comprising the same) may be conjugated onto carbon nanoparticles, e.g. carbon nanotubes. Mesoporous carbon nanoparticles are preferred for oral administration. Silica-based nanoparticles (SiNPs) are also preferred. SiNPs are biocompatible and show excellent properties in selective tumor targeting and vaccine delivery. The abundant silanol groups on the surface of SiNPs may be used for further modification to introduce additional functionality, such as cell recognition, absorption of specific biomolecules, improvement of interaction with cells, and enhancement of cellular uptake. Mesoporous silica nanoparticles are particularly preferred.

Liposomes are typically formed by phospholipids, such as 1,2-dioleoyl-3-trimethylammonium propane (DOTAP). In general, cationic liposomes are preferred. Liposomes are self-assembling with a phospholipid bilayer shell and an aqueous core. Liposomes can be generated as unilameller vesicles (having a single phospholipid bilayer) or as multi-lameller vesicles (having several concentric phospholipid shells separated by layers of water). Accordingly, antigens can be encapsulated in the core or between different layers/shells. Preferred liposome systems are those approved for human use, such as Inflexal® V and Epaxal®.

Immunostimulating complexes (ISCOM) are cage like particles of about 40 nm (diameter), which are colloidal saponin containing micelles, for example made of the saponin adjuvant Quil A, cholesterol, phospholipids, and the (poly)peptide antigen (such as the antigenic peptide or a polypeptide comprising the same). These spherical particles can trap the antigen by apolar interactions. Two types of ISCOMs have been described, both of which consist of cholesterol, phospholipid (typically either phosphatidylethanolamine or phos-phatidylcholine) and saponin (such as QuilA).

Virus-like particles (VLP) are self-assembling nanoparticles formed by self-assembly of biocompatible capsid proteins. Due to the naturally-optimized nanoparticle size and repetitive structural order VLPs can induce potent immune responses. VLPs can be derived from a variety of viruses with sizes ranging from 20 nm to 800 nm, typically in the range of 20-150 nm. VLPs can be engineered to express additional peptides or proteins either by fusing these peptides/proteins to the particle or by expressing multiple antigens. Moreover, antigens can be chemically coupled onto the viral surface to produce bioconjugate VLPs.

Examples of self-assembled proteins include ferritin and major vault protein (MVP). Ferritin is a protein that can self-assemble into nearly-spherical 10 nm structure. Ninety-six units of MVP can self-assemble into a barrel-shaped vault nanoparticle, with a size of approximately 40 nm wide and 70 nm long. Antigens that are genetically fused with a minimal interaction domain can be packaged inside vault nanoparticles by self-assembling process when mixed with MVPs. Accordingly, the antigen (such as the antigenic peptide according to the present invention of a polypeptide comprising the same) may be fused to a self-assembling protein or to a fragment/domain thereof, such as the minimal interaction domain of MVP. Accordingly, the present invention also provides a fusion protein comprising a self-assembling protein (or a fragment/domain thereof) and the antigenic peptide according to the present invention.

In general, preferred examples of nanoparticles (NPs) include iron oxide beads, polystyrene microspheres, poly(γ-glutamic acid) (γ-PGA) NPs, iron oxide-zinc oxide NPs, cationized gelatin NPs, pluronic-stabilized poly(propylene sulfide) (PPS) NPs, PLGA NPs, (cationic) liposomes, (pH-responsive) polymeric micelles, PLGA, cancer cell membrane coated PLGA, lipid-calcium-phosphate (LCP) NPs, liposome-protamine-hyaluronic acid (LPH) NPs, polystyrene latex beads, magnetic beads, iron-dextran particles and quantum dot nanocrystals.

Preferably, the nanoparticle further comprises an adjuvant, for example a toll-like receptor (TLR) agonist. Thereby, the antigenic peptide (the polypeptide/protein/nucleic acid comprising the antigenic peptide) can be delivered together with an adjuvant, for example to antigen-presenting cells (APCs), such as dendritic cells (DCs). The adjuvant may be encapsulated by the nanoparticle or bound to/conjugated to the surface of the nanoparticle, preferably similarly to the antigenic peptide.

Particularly preferred adjuvants are polyinosinic:polycytidylic acid (also referred to as "poly I:C") and/or its derivative poly-ICLC. Poly I:C is a mismatched double-stranded RNA with one strand being a polymer of inosinic acid, the other a polymer of cytidylic acid. Poly I:C is an immunostimulant known to interact with toll-like receptor 3 (TLR3). Poly I:C is structurally similar to double-stranded RNA, which is the "natural" stimulant of TLR3. Accordingly, poly I:C may be considered a synthetic analog of double-stranded RNA. Poly-ICLC is a synthetic complex of carboxymethylcellulose, polyinosinic-polycytidylic acid, and poly-L-lysine double-stranded RNA. Similar to poly I:C, also poly-ICLC is a ligand for TLR3. Poly I:C and poly-ICLC typically stimulate the release of cytotoxic cytokines. A preferred example of poly-ICLC is Hiltonol® *.

Immunogenic Compositions and Kits

Immunogenic compositions according to the invention comprises at least one of the following:
  an antigenic peptide according to the present invention,
  an immunogenic compound according to the present invention,
  a nanoparticle according to the present invention,
  a cell according to the present invention,
  a nucleic acid according to the present invention, or
  a host cell according to the present invention.

Preferably, the immunogenic composition further comprises one or more pharmaceutically acceptable excipients or carriers.

The immunogenic composition of the invention may be in any form suitable for the purposes of the invention. For example, said composition may be in a form suitable for parenteral, enteral or topical administration, such as a liquid suspension, a solid dosage form (granules, pills, capsules or tablets), or a paste or gel. It is within the skill of the person in the art to select the appropriate form of the composition for the intended purpose.

Indeed, in the context of the present invention, it can be particularly advantageous to use (poly)peptides, or nucleic acids encoding thereof, because of their ease of manufacturing at a low cost and relative safety with no potential for reassortment, infection or recombination.

Antigenic peptides of the invention may be administered in the form of immunogenic compounds according to the present invention, cells loaded therewith according to the present invention, nanoparticles according to the present invention, nucleic acids according to the present invention, host cells according to the present invention and/or immunogenic compositions according to the present invention.

According to one embodiment, they may be administered in the form of a micro-organism such as a gut bacterial species.

Entire gut bacterial species can also be advantageous as they have the potential to trigger a greater immune response than the (poly)peptides or nucleic acids they contain.

Alternatively, gut bacteria according to the invention may be in the form of probiotics, i.e. of live gut bacterium, which can thus be used as food additive thanks to the health benefits it can provide. Those can be for example lyophilized in granules, pills or capsules, or directly mixed with dairy products for consumption.

One skilled in the art would readily understand that an antigenic peptide of the invention can be selected based upon the nature of the cancer to be prevented or treated, and/or on the human gene/human tumor antigen involved in said cancer. For example, should one wish to prevent or treat melanoma which involves a Glycoprotein 100 (gp100), a TRP1, a TRP2, a tyrosinase and/or a Melan A/MART1 antigen, one can select any of the corresponding antigenic peptide(s) as described in Table 1A.

It shall be understood that co-administration of several antigenic peptides of the invention is particularly preferred, so as to enhance the immune response.

Thus, according to a preferred embodiment, the composition of the invention comprises at least 2 antigenic peptides (which may be in the form of immunogenic compounds) as defined above, which includes at least 3 antigenic peptides, or at least 4 antigenic peptides, or at least 5 antigenic peptides, or at least 6 antigenic peptides, or at least 7 antigenic peptides, or at least 8 antigenic peptides, or at least 9 antigenic peptides, or at least 10 antigenic peptides, or at least 11 antigenic peptides, or at least 12 antigenic peptides, or at least 13 antigenic peptides, or at least 14 antigenic peptides, or at least 15 antigenic peptides, or at least 20 antigenic peptides, or at least 25 antigenic peptides, or at least 50 antigenic peptides, or at least 100 antigenic peptides, or at least 500 antigenic peptides, or at least 1000 antigenic peptides, or at least 1500 antigenic peptides. It is within the skill of the person in the art to select the combination of antigenic peptides and/or immunogenic compounds that is suitable for the intended purpose. For example, should one wish to prevent or treat melanoma which involves a tumor antigen encoded by a gene according to Table 1B, one can select any combination of the corresponding antigenic peptides as described in Table 1A.

In a particularly preferred embodiment two distinct antigenic peptides according to the present invention (e.g., relating to the same type of cancer and/or to the same reference antigen) are combined. In other words, the composition according to the present invention preferably comprises (i) two distinct immunogenic compounds according to the present invention;
(ii) two distinct antigenic peptides according to the present invention;
(iii) two distinct nanoparticles according to the present invention; or
(iv) two distinct nucleic acids according to the present invention.

The composition according to the invention can further comprise other active agents, for example such, which can enhance the effects of the antigenic peptide or immunogenic compound. Alternatively, the composition may not comprise any other active agents (i.e., other than the antigenic peptide according to the present invention, the immunogenic compound according to the present invention, the nanoparticle according to the present invention, the cell according to the present invention, the nucleic acid according to the present invention, or the host cell according to the present invention).

According to a preferred embodiment, said composition further comprises at least one immunostimulatory agent, in particular so as to potentiate the immune response mediated by the antigenic peptide. Preferred immunostimulatory agents according to the invention include, without limitation, immune adjuvants, antigen-presenting cells, and combinations thereof. Preferably, the immunostimulatory agent is an immune adjuvant or an antigen-presenting cell (APC).

Some immune adjuvants are indeed capable of favoring and prolonging the duration of interaction between an antigen and the immune system, while others are capable of recruiting and activating cells of the natural immunity so as to induce an adaptive response. The adjuvants belonging to the former category include, without limitation, mineral compounds such as alum, aluminum hydroxide, aluminum phosphate, calcium phosphate hydroxide; and oil-based emulsions such as paraffin oil, starch oil, Freund's complete/incomplete adjuvant (FCA/FIA), saponins (e.g. from the plants Quillaja, Soybean, Polygala senega). The adjuvants of belonging to the latter category include, without limitation, immunostimulatory complexes (ISCOMs) such as cytokines (e.g. GM-CSF; Interleukins such as IL-1, IL-2, IL6, IL8, or IL12; Tumor necrosis factors (TNFs) such as TNFα or TNFβ; Interferons IFNS such as IFNα, IFNβ, IFNγ or IFNδ, etc); ligands of toll-like receptors (TLRs) such as imiquimod, resiquimod or MPL; exosomes such as exosomes derived from dendritic cells (DCs) or from tumor cells; bacterial products such as heat-shock proteins (HSPs such as gp96, hsp90, hsp70, calreticulin, hsp110, hsp170), pathogen-associated molecular patterns (PAMPs), trehalose dimicolate (TDM), muramyldipeptide (MDP), polysaccharide (PLS) such as polysaccharide-K.

According to one embodiment, the immune adjuvant may be the HHD-DR3 peptide MAKTIAYDEEARRGLERGLN (SEQ ID NO:144).

More preferably, the immune adjuvants is a protein/peptide having immuno-adjuvant properties, such as providing stimulation of CD4+Th1 cells, as described herein. A preferred example thereof is a non-tumor antigen that recalls immune memory or provides a non-specific help or could be a specific tumor-derived helper peptide, such as tetanus helper peptide, keyhole limpet hemocyanin peptide or PADRE peptide, as described herein. Another preferred example is a specific tumor derived helper peptide, which may be presented by MHC II, in particular by HLA-DR, HLA-DP or HLA-DQ, such as fragments of shared overexpressed tumor antigens, e.g. HER2, NY-ESO-1, hTERT or IL13RA2, as described above.

Particularly preferred adjuvants are polyinosinic:polycytidylic acid (also referred to as "poly I:C") and/or its derivative poly-ICLC. Poly I:C is a mismatched double-stranded RNA with one strand being a polymer of inosinic acid, the other a polymer of cytidylic acid. Poly I:C is an immunostimulant known to interact with toll-like receptor 3 (TLR3). Poly I:C is structurally similar to double-stranded RNA, which is the "natural" stimulant of TLR3. Accordingly, poly I:C may be considered a synthetic analog of double-stranded RNA. Poly-ICLC is a synthetic complex of carboxymethylcellulose, polyinosinic-polycytidylic acid, and poly-L-lysine double-stranded RNA. Similar to poly I:C, also poly-ICLC is a ligand for TLR3. Poly I:C and poly-ICLC typically stimulate the release of cytotoxic cytokines. A preferred example of poly-ICLC is Hiltonol®.

Antigen-presenting cells (APCs) are also of particular interest, as their main function is to process antigens and present it on the cell surface to the T cells of the immune system, so as to initiate and modulate T-cell responses in vivo. In the present composition, it is preferred that the APCs are loaded with the antigenic peptide(s) and/or immunogenic compound(s) according to the invention, which can be done by exposing APCs in vitro with said antigenic peptide(s) and/or immunogenic compound(s) (Rizzo et al., Ex vivo loading of autologous dendritic cells with tumor antigens. Methods Mol Biol. 2014; 1139:41-4; Rolinski and Hus, Breaking immunotolerance of tumors: a new perspective for dendritic cell therapy. J Immunotoxicol. 2014 October; 11 (4): 311-8).

Preferred antigen-presenting cells according to the invention are dendritic cells (DCs). It can indeed be advantageous to combine at least one antigenic peptide or immunogenic compound according to the invention with dendritic cells, as those are the most potent antigen-presenting cells and have been reported to be frequently functionally defective in cancer patients. Dendritic cells can be easily obtained by the skilled person in the art from either healthy compatible donors (i.e. the dendritic cells are HLA-related) or from the patient himself provided that they are functional (i.e. the dendritic cells are autologous), for example by direct isolation from the peripheral blood, or by derivation from peripheral blood cells such as CD14+ monocytes or CD34+ hematopoietic precursors (Emens et al., 2008). Dendritic cells can indeed be distinguished from other cells of peripheral blood by their surface markers, such as S100, p55, CD83, and/or OX62, and may thus be isolated and purified based on said markers using cell cultures techniques well-known in the art.

According to a preferred embodiment, the pharmaceutical composition may further comprise at least one anti-cancer therapeutic agent. Said therapeutic agent is thus preferably capable of preventing and/or treating the same type of cancer than the one for which the antigenic peptide according to the invention is used. Particularly preferred anti-cancer therapeutic agents according to the invention include, without limitation, antibodies, tumor cell lysates, chemotherapeutic agents, radiotherapeutic agents and combinations thereof. Most preferably, the anti-cancer therapeutic agent is selected from antibodies, tumor cell lysates, chemotherapeutic agents, radiotherapeutic agents, immune checkpoint modulators and combinations thereof.

Antibodies are particularly advantageous in cancer therapy as they can either bind to specific antigens on cancer cell surfaces, thereby directing the therapy to the tumor (i.e. these are referred as tumor-targeting antibodies), or block immune checkpoints that are dysregulated in cancer (i.e. these are referred herein as immunomodulatory antibodies). The purpose of the later type of antibodies is to inhibit cancer immune resistance, which can notably be observed against T cells that are specific for tumor antigens. Indeed, as well-known in the art, under normal physiological conditions, immune checkpoints are crucial for the maintenance of self-tolerance (i.e. prevention of autoimmunity) and protect tissues from damage when the immune system is responding to pathogenic infection. However, in cancer, immune-checkpoints expression can be dysregulated as an important mechanism of immune resistance. Said resistance has notably been observed in melanoma, ovarian, lung, glioblastoma, breast, and pancreatic cancers with regard to the PD-L1 checkpoint (Konishi et al., B7-H1 expression on non-small cell lung cancer cells and its relationship with tumor-infiltrating lymphocytes and their PD-1 expression. Clin Cancer Res. 2004 Aug. 1;10 (15): 5094-100; Ghebeh et al., The B7-H1 (PD-L1) T lymphocyte-inhibitory molecule is expressed in breast cancer patients with infiltrating ductal carcinoma: correlation with important high-risk prognostic factors. Neoplasia. 2006 March;8 (3): 190-8; Hino et al., Tumor cell expression of programmed cell death-1 ligand 1 is a prognostic factor for malignant melanoma. Cancer. 2010 Apr. 1;116 (7): 1757-66). Other examples of immune checkpoints include, without limitation, PD-L2, PD1, CD80, CD86, CTLA4, B7H3, B7H4, PVR, TIGIT, GAL9, LAG-3, GITR, CD137, TIM3, VISTA, VISTA-R (Pico de Coaña et al., Checkpoint blockade for cancer therapy: revitalizing a suppressed immune system. Trends Mol Med. 2015 August; 21 (8): 482-91; Pardoll D M. The blockade of immune checkpoints in cancer immunotherapy. Nat Rev Cancer. 2012 Mar. 22;12 (4): 252-64).

Antibodies are usually employed for the above purposes either in the form of naked monoclonal antibodies (i.e. non-conjugated), or conjugated to another molecule which can be toxic to cells or radioactive.

Examples of well-known monoclonal tumor-targeting antibodies used in cancer immunotherapy include, without limitation, alemtuzumab (chronic lymphocytic leukemia), bevacizumab (colorectal cancer, glioblastoma multiforme, cervical cancer, lung cancer, renal cancer), brentuximab/vedotin (lymphomas), blinatumumab (acute lymphoblastic leukemia), catumaxomab (malignant ascites in EPCAM+ cancers), cetuximab (head and neck cancer, colorectal cancer), denosumab (breast, prostate and bone cancers), Gemtuzumab/ozogamicin (acute myeloid keulemia), ibritumomab/tiuxetan (non-Hodgkin lymphoma), panitumumab (colorectal cancer), pertuzumab (breast cancer), obinutuzumab (chronic lymphocytic leukemia), ofatumumab (chronic lymphocytic leukemia), opilimumab (melanoma), ramucirumab (gastric and gastro-oeasophageal cancers), rituximab (chronic lymphocytic leukemia and non-Hodgkin lymphoma), siltuximab (multicentric's Catsleman's disease), tositumomab (non-Hodgkin lymphoma), and trastuzumab (breast, gastric and gastro-oeasophageal cancers); while examples of immunomodulatory antibodies include, without limitation, ipilimumab (melanoma) which blocks the CTLA4-dependent immune checkpoint, nivolumab (melanoma, lung cancer) and prembrolizubmab (melanoma) which both block the PDCD1-dependent immune checkpoint, as well as MPDL3280A, MEDI4736, MEDI0680, and MSB0010718C which all block the PD-L1-dependent immune checkpoint (Sharma and Allison, The future of immune checkpoint therapy. Science. 2015 Apr. 3;348 (6230): 56-61).

Other antibodies for cancer immunotherapy have been described in Buqué et al., Trial Watch: Immunomodulatory monoclonal antibodies for oncological indications. Oncoimmunology. 2015 Mar. 2;4 (4): e1008814. eCollection 2015 April; Redman et al., Mechanisms of action of therapeutic antibodies for cancer. Mol Immunol. 2015 October;67 (2 Pt A): 28-45; Simpson and Caballero, Monoclonal antibodies for the therapy of cancer MC Proc. 2014; 8 (Suppl 4): 06 as well as on the antibody society website (list of therapeutic monoclonal antibodies approved or in review in the European Union or United States available on the weblink www.antibodysociety.org/news/approved_mabs.php).

Tumor cell lysates may also be combined with the antigenic peptide(s) according to the invention. Tumor cells are indeed capable of priming the immune response, by presenting endogenous peptides-MHC complexes, as well as via dendritic cells (DCs) of the host which can process and present the antigen delivered by said lysates. The range of antigens against which an immune response can be induced is thereby increased. Tumor cell lysates can be easily obtained by treating tumor cells with a heat shock and/or a chemical treatment, and can be autologous (i.e. isolated from the patient), or allogeneic (i.e. isolated from another subject).

Standard chemotherapeutic drugs and radiotherapeutic agents need not be further described herein as they have been extensively described in the literature, notably by Baskar et al. (Baskar et al., Cancer and radiation therapy: current advances and future directions. Int J Med Sci. 2012; 9 (3): 193-9), Paci et al., (Paci et al., Review of therapeutic drug monitoring of anticancer drugs part 1—cytotoxics. Eur J Cancer. 2014 August;50 (12): 2010-9) and Widmer et al. (Widmer et al., Review of therapeutic drug monitoring of anticancer drugs part two—targeted therapies. Eur J Cancer. 2014 August;50 (12): 2020-36). A list of such drugs and agents is also available on the cancer.gov website (www.cancer.gov/about-cancer/treatment/drugs).

Preferably, the immune checkpoint modulator for combination with the antigenic peptide as defined herein is an activator or an inhibitor of one or more immune checkpoint molecule(s) selected from CD27, CD28, CD40, CD122, CD137, OX40, GITR, ICOS, A2AR, B7-H3, B7-H4, BTLA, CD40, CTLA-4, IDO, KIR, LAG3, PD-1, TIM-3, VISTA, CEACAM1, GARP, PS, CSF1R, CD94/NKG2A, TDO, GITR, TNFR and/or FasR/DcR3; or an activator or an inhibitor of one or more ligands thereof.

More preferably, the immune checkpoint modulator is an activator of a (co-) stimulatory checkpoint molecule or an inhibitor of an inhibitory checkpoint molecule or a combination thereof. Accordingly, the immune checkpoint modulator is more preferably (i) an activator of CD27, CD28, CD40, CD122, CD137, OX40, GITR and/or ICOS or (ii) an inhibitor of A2AR, B7-H3, B7-H4, BTLA, CD40, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or FasR/DcR3.

Even more preferably, the immune checkpoint modulator is an inhibitor of an inhibitory checkpoint molecule (but preferably no inhibitor of a stimulatory checkpoint molecule). Accordingly, the immune checkpoint modulator is even more preferably an inhibitor of A2AR, B7-H3, B7-H4, BTLA, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or
DcR3 or of a ligand thereof.

It is also preferred that the immune checkpoint modulator is an activator of a stimulatory or costimulatory checkpoint molecule (but preferably no activator of an inhibitory checkpoint molecule). Accordingly, the immune checkpoint modulator is more preferably an activator of CD27, CD28, CD40, CD122, CD137, OX40, GITR and/or ICOS or of a ligand thereof.

It is even more preferred that the immune checkpoint modulator is a modulator of the CD40 pathway, of the IDO pathway, of the LAG3 pathway, of the CTLA-4 pathway and/or of the PD-1 pathway. In particular, the immune checkpoint modulator is preferably a modulator of CD40, LAG3, CTLA-4, PD-L1, PD-L2, PD-1 and/or IDO, more preferably the immune checkpoint modulator is an inhibitor of CTLA-4, PD-L1, PD-L2, PD-1, LAG3, and/or IDO or an activator of CD40, even more preferably the immune checkpoint modulator is an inhibitor of CTLA-4, PD-L1, PD-1, LAG3 and/or IDO, even more preferably the immune checkpoint modulator is an inhibitor of LAG3, CTLA-4 and/or PD-1, and most preferably the immune checkpoint modulator is an inhibitor of CTLA-4 and/or
PD-1.

Accordingly, the checkpoint modulator for combination with the antigenic peptide may be selected from known modulators of the CTLA-4 pathway or the PD-1 pathway. Preferably, the checkpoint modulator for combination with the antigenic peptide as defined herein may be selected from known modulators of the the CTLA-4 pathway or the PD-1 pathway. Particularly preferably, the immune checkpoint modulator is a PD-1 inhibitor. Preferred inhibitors of the CTLA-4 pathway and of the PD-1 pathway include the monoclonal antibodies YervoyR (Ipilimumab; Bristol Myers Squibb) and Tremelimumab (Pfizer/MedImmune) as well as OpdivoR (Nivolumab; Bristol Myers Squibb), KeytrudaR (Pembrolizumab; Merck), Durvalumab (MedImmune/AstraZeneca), MEDI4736 (AstraZeneca; cf. WO 2011/066389 A1), MPDL3280A (Roche/Genentech; cf. U.S. Pat. No. 8,217,149 B2), Pidilizumab (CT-011; CureTech), MEDI0680 (AMP-514; AstraZeneca), MSB-0010718C (Merck), MIH1 (Affymetrix) and Lambrolizumab (e.g. disclosed as hPD109A and its humanized derivatives h409All, h409A16 and h409A17 in WO2008/156712; Hamid et al., 2013; N. Engl. J. Med. 369:134-144). More preferred checkpoint inhibitors include the CTLA-4 inhibitors YervoyR (Ipilimumab; Bristol Myers Squibb) and Tremelimumab (Pfizer/MedImmune) as well as the PD-1 inhibitors OpdivoR (Nivolumab; Bristol Myers Squibb), KeytrudaR (Pembrolizumab; Merck), Pidilizumab (CT-011; CureTech), MEDI0680 (AMP-514; AstraZeneca), AMP-224 and Lambrolizumab (e.g. disclosed as hPD109A and its humanized derivatives h409All, h409A16 and h409A17 in WO2008/156712; Hamid O. et al., 2013; N. Engl. J. Med. 369:134-144.

It is also preferred that the immune checkpoint modulator for combination with the antigenic peptide as defined herein is selected from the group consisting of Pembrolizumab, Ipilimumab, Nivolumab, MPDL3280A, MEDI4736, Tremelimumab, Avelumab, PDR001, LAG525, INCB24360, Varlilumab, Urelumab, AMP-224 and CM-24.

It is within the skill of ordinary person in the art to select the appropriate immune anti-cancer therapeutic agent for the purposes of the invention. For example, should one wish to prevent or treat melanoma, a lysate from melanoma cells and/or the antibody opilimumab can preferably be used, along with the corresponding antigenic peptide as described in Table 1A.

The anti-cancer therapeutic agent can also be administered in association with the composition of the invention, either simultaneously, separately, or sequentially. Should the composition and the therapeutic agent be administered in a separate or sequential manner, those may be administered in distinct pharmaceutical forms.

Thus, in another aspect, the invention relates to a composition of the invention and at least one anti-cancer therapeutic agent as described above, as a combined preparation for a simultaneous, separate, or sequential administration. In other terms, the invention proposes a combined use of the composition the invention and least one anti-cancer therapeutic agent as described above, for a simultaneous, separate, or sequential administration.

In a further aspect, the present invention also relates to a kit-of-parts, preferably for use in the prevention and/or treatment of cancer, the kit comprising at least one of:
an immunogenic compound according to the present invention,
an antigenic peptide according to the present invention, a nanoparticle according to the present invention,
a cell according to the present invention,
a nucleic acid according to the present invention,
a host cell according to the present invention, or
an immunogenic composition according to the present invention.

In particular, the kit-of-parts of the invention may comprise more than one of the above described components. For example, the kit-of-parts according to the present invention may comprise at least two different immunogenic compounds, at least two different antigenic peptides, at least two different nanoparticles, at least two different cells, at least two different nucleic acids, at least two different host cells, and/or at least two different immunogenic compositions. Preferably, such different components comprised by the kit-of-parts as described above differ in the antigenic peptides according to the present invention, for example one component relating to a first antigenic peptide, and one component relating to a second antigenic peptide (distinct from the first antigenic peptide).

For example, the kit may comprise two distinct immunogenic compounds according to the present invention.

For example, the kit may comprise two distinct antigenic peptides according to the present invention.

For example, the kit may comprise two distinct nanoparticles according to the present invention.

For example, the kit may comprise two distinct nucleic acids according to the present invention.

The various components of the kit-of-parts may be packaged in one or more containers. The above components may be provided in a lyophilized or dry form or dissolved in a suitable buffer. The kit may also comprise additional reagents including, for instance, preservatives, growth media, and/or buffers for storage and/or reconstitution of the above-referenced components, washing solutions, and the like. In addition, the kit-of-parts according to the present invention may optionally contain instructions of use.

Moreover, the present invention also provides a vaccination kit for treating, preventing and/or stabilizing a cancer, comprising the immunogenic composition as described herein or a vaccine as described herein and instructions for use of said immunogenic composition or of said vaccine in the prevention and/or treatment of a cancer.

Preferably, such a kit further comprises a package insert or instruction leaflet with directions to prevent or to treat a cancer by using the immunogenic compound according to the present invention, the antigenic peptide according to the present invention, the nanoparticle according to the present invention, the cell according to the present invention, the nucleic acid according to the present invention, the host cell according to the present invention, or the immunogenic composition according to the present invention.

It is also preferred that, in addition to any of components as described above, the kit comprises an anti-cancer therapeutic agent as described herein.

Medical Treatment and Uses

As stated above, the composition of the invention can be particularly useful for therapeutic purposes, notably for triggering a specific immune response towards a particular tumor antigen/protein, so as to prevent or treat cancer in a patient in need thereof.

In a further aspect the present invention provides an immunogenic compound according to the present invention, an antigenic peptide according to the present invention, a nanoparticle according to according to the present invention, a cell according to the present invention, a nucleic acid according to the present invention, a host cell according to the present invention, or an immunogenic composition according to the present invention, for use in the prevention and/or in the treatment of a cancer. Preferably said cancer relates to the (reference) antigen of the antigenic peptide as described above.

Accordingly, the present invention provides a method for preventing and/or treating a cancer or initiating, enhancing or prolonging an anti-tumor-response in a subject in need thereof comprising administering to the subject
the immunogenic compound according to the present invention,
the antigenic peptide according to the present invention,
the nanoparticle according to the present invention,
the cell according to the present invention,
the nucleic acid according to the present invention,
the host cell according to the present invention,
the immunogenic composition according to the present invention, or
the combination according to the present invention as described herein.

Moreover, the present invention provides a method for eliciting or improving, in a subject, an immune response against one or multiple epitopes that is dependent on $CD8^+$ cytotoxic T cells, wherein said method comprises administering to said subject any one of:
the immunogenic compound according to the present invention,
the antigenic peptide according to the present invention,
the nanoparticle according to the present invention,
the cell according to the present invention,
the nucleic acid according to the present invention,
the host cell according to the present invention,
the immunogenic composition according to the present invention, or
the combination according to the present invention as described herein.

An immune response that is dependent on CD8+ response can be determined by evaluating an inflammatory response, a pro-inflammatory cytokine response, including an increase in the expression of one or more of IFN-$\gamma$, TNF-$\alpha$ and IL-2 mRNA or protein relative to the level before administration of the compounds of the invention. It can also be measured by an increase in the frequency or absolute number of antigen-specific T cells after administration of the compounds of the invention, measured by HLA-peptide multimer staining, ELISPOT assays, and delayed type hypersensitivity tests. It can also be indirectly measured by an increase in antigen-specific serum antibodies that are dependent on antigen-specific T helper cells.

The present invention also provides a method for eliciting or improving, in a subject, an immune response against one or multiple antigens or antigenic epitopes that is restricted by multiple MHC class I molecules, wherein said method comprises administering to said subject any one of:
the immunogenic compound according to the present invention,
the antigenic peptide according to the present invention,
the nanoparticle according to the present invention,
the cell according to the present invention,
the nucleic acid according to the present invention,
the host cell according to the present invention,
the immunogenic composition according to the present invention, or
the combination according to the present invention as described herein.

A method for eliciting or improving, in a subject, an immune response against multiple epitopes as described herein, that is restricted by multiple MHC class I molecules can be determined by evaluating a cytokine response, including an increase in the expression of one or more of IFN-γ, TNF-α and IL-2 mRNA or protein relative to the level before administration of the compounds of the invention, after in vitro stimulation of T cells with individual peptides binding to discrete MHC class I molecules on antigen presenting cells. Restriction to MHC class I molecules can also be validated by using antigen presenting cells expressing MHC class I molecules, or by using MHC class I blocking antibodies. It can also be measured by an increase in the frequency or absolute number of antigen-specific T cells after administration of the compounds of the invention, measured by HLA-peptide multimer staining, using multimers assembled with MHC class I molecules.

Thus, in another aspect, the invention relates to a composition as defined above, for use as a medicament. Moreover, the immunogenic compound according to the present invention,
the antigenic peptide according to the present invention,
the nanoparticle according to the present invention,
the cell according to the present invention,
the nucleic acid according to the present invention,
the host cell according to the present invention,
the immunogenic composition according to the present invention, or
the combination according to the present invention as described herein may be used as a medicament.

The invention relates more particularly to a composition as defined above, for use as a vaccine for immunotherapy. Moreover, the immunogenic compound according to the present invention,
the antigenic peptide according to the present invention,
the nanoparticle according to the present invention,
the cell according to the present invention,
the nucleic acid according to the present invention,
the host cell according to the present invention,
the immunogenic composition according to the present invention, or
the combination according to the present invention as described herein may be used as vaccine, in particular for (cancer) immunotherapy.

As used in the context of the present invention, the term "vaccine" refers to a biological preparation that provides innate and/or adaptive immunity, typically to a particular disease, preferably cancer. Thus, a vaccine supports in particular an innate and/or an adaptive immune response of the immune system of a subject to be treated. For example, the antigenic peptide according to the present invention typically leads to or supports an adaptive immune response in the patient to be treated.

In the context of the present invention, the vaccine (composition) can induce a specific immune response against a tumor antigen, and is thus preferably used to prevent or treat cancer. It can also be referred herein as a cancer vaccine.

Accordingly, in a preferred embodiment, the invention relates to a composition as defined above, for use in the prevention and/or treatment of cancer in a subject in need thereof. More precisely, the invention relates to the use of the composition of the invention for manufacturing a medicament to prevent or treat cancer in a subject in need thereof.

In other words, the invention relates to a method for preventing or treating cancer in a subject in need thereof, comprising administering an effective amount of the composition of the invention, to said subject.

Methods of administration of a medicament are well-known to the skilled person in the art. With regard to the composition of the invention, it can be directly administered into the subject, into the affected organ (i.e. local administration) or systemically (i.e. enteral or parenteral administration), or even applied ex vivo to cells derived from the subject or a human cell line which are subsequently administered to the subject, or even used in vitro to select a subpopulation of immune cells derived from the subject, which are then re-administered to the said subject. Enteral administrations as used herein includes oral and rectal administrations, as well as administrations via gastric feeding tubes, duodenal feeding tubes or gastrostomy, while parenteral administrations includes, among others, subcutaneous, intravenous, intramuscular, intra-arterial, intradermal, intraosseous, intracerebral, and intrathecal injections. The administration method will often depend upon the antigenic peptide(s) and/or immunogenic compound(s) present in the composition, and the type of cancer to be treated and other active agents that may be contained in said composition. For example, the administration is preferably an intramuscular or an intradermal injection if the immunogenic compound is a nucleic acid as defined above, the oral/nasal administration being particularly preferred if said nucleic acid is cloned into a viral vector. Alternatively, the administration is preferably an intramuscular, an intradermal or an oral administration if the antigenic peptide and/or immunogenic compound is a (poly)peptide as defined above or if it is loaded in/on a nanoparticle as described herein. Yet, still alternatively, the administration is preferably an oral administration if the antigenic peptide and/or immunogenic compound is delivered in the form of a gut bacterium as defined above, notably if the gut bacterium is in the form of probiotics.

The antigenic peptides and/or immunogenic compounds according to the invention can further be encapsulated so as to facilitate their administration to the subject in need thereof. For example, those may be encapsulated into peptide nanocarriers (preferable if the immunogenic compound is a nucleic acid or a (poly)peptide), into virosomes (preferable if the immunogenic compound is a nucleic acid or a (poly)peptide), or into lipid-based carrier systems such as liposome-polycation-DNA complex (preferable if the immunogen is a nucleic acid or a (poly)peptide) (Trovato M, De Berardinis P. Novel antigen delivery systems. World J Virol. 2015 Aug. 12;4 (3): 156-68; Saade F, Petrovsky N. Technologies for enhanced efficacy of DNA vaccines. Expert Rev Vaccines. 2012 Feb; 11 (2): 189-209; Li et al., Peptide Vaccine: Progress and Challenges. Vaccines (Basel). 2014 Jul. 2;2 (3): 515-36).

The composition may also be administered more than once so as to achieve the desired effect. In a preferred embodiment, said composition is administered repeatedly, at least twice, and preferably more than twice. This can be done over an extended period of time, such as weekly, every other week, monthly, yearly, or even several years after the first administration to ensure that the subject is properly immunized.

According to one embodiment, an antigenic peptide or an immunogenic compound according to the invention may be used for the preparation of a composition and/or of an immunogenic composition for preventing or treating cancer in a subject in need thereof.

Combination Therapy

The administration of the antigenic peptide according to the present invention, the immunogenic compound according to the present invention, the nanoparticle according to the present invention, the cell according to the present invention, the nucleic acid according to the present invention, the host cell according to the present invention, and the immunogenic composition according to the present invention, in particular in the methods and uses according to the invention, can be carried out alone or in combination with a co-agent useful for treating and/or preventing cancer, such as an anti-cancer therapeutic agent.

Said therapeutic agent is thus preferably capable of preventing and/or treating the same type of cancer as the one for which the antigenic peptide according to the invention is used. Particularly preferred anti-cancer therapeutic agents according to the invention include, without limitation, antibodies, tumor cell lysates, chemotherapeutic agents, radiotherapeutic agents, immune checkpoint modulators and combinations thereof.

Antibodies are particularly advantageous in cancer therapy as they can either bind to specific antigens on cancer cell surfaces, thereby directing the therapy to the tumor (i.e. these are referred as tumor-targeting antibodies), or block immune checkpoints that are dysregulated in cancer (i.e. these are referred herein as immunomodulatory antibodies). The purpose of the later type of antibodies is to inhibit cancer immune resistance, which can notably be observed against T cells that are specific for tumour antigens. Indeed, as well-known in the art, under normal physiological conditions, immune checkpoints are crucial for the maintenance of self-tolerance (i.e. prevention of autoimmunity) and protect tissues from damage when the immune system is responding to pathogenic infection. However, in cancer, immune-checkpoints expression can be dysregulated as an important mechanism of immune resistance. Said resistance has notably been observed in melanoma, ovarian, lung, glioblastoma, breast, and pancreatic cancers with regard to the PD-L1 checkpoint (Konishi et al., B7-H1 expression on non-small cell lung cancer cells and its relationship with tumor-infiltrating lymphocytes and their PD-1 expression. Clin Cancer Res. 2004 Aug. 1;10 (15): 5094-100; Ghebeh et al., The B7-H1 (PD-L1) T lymphocyte-inhibitory molecule is expressed in breast cancer patients with infiltrating ductal carcinoma: correlation with important high-risk prognostic factors. Neoplasia. 2006 Mar;8 (3): 190-8; Hino et al., Tumor cell expression of programmed cell death-1 ligand 1 is a prognostic factor for malignant melanoma. Cancer. 2010 Apr. 1;116 (7): 1757-66). Other examples of immune checkpoints include, without limitation, PD-L2, PD1, CD80, CD86 CTLA4, B7H3, B7H4, PVR, TIGIT, GAL9, LAG-3, GITR, CD137, TIM3, VISTA, VISTA-R (Pico de Coaña et al., Checkpoint blockade for cancer therapy: revitalizing a suppressed immune system. Trends Mol Med. 2015 August; 21 (8): 482-91; Pardoll D M1. The blockade of immune checkpoints in cancer immunotherapy. Nat Rev Cancer. 2012 Mar. 22;12 (4): 252-64).

Antibodies are usually employed for the above purposes either in the form of naked monoclonal antibodies (i.e. non-conjugated), or conjugated to another molecule which can be toxic to cells or radioactive.

Examples of well-known monoclonal tumor-targeting antibodies used in cancer immunotherapy include, without limitation, alemtuzumab (chronic lymphocytic leukemia), bevacizumab (colorectal cancer, glioblastoma multiforme, cervical cancer, lung cancer, renal cancer), brentuximab/vedotin (lymphomas), blinatumumab (acute lymphoblastic leukemia), catumaxomab (malignant ascites in EPCAM+ cancers), cetuximab (head and neck cancer, colorectal cancer), denosumab (breast, prostate and bone cancers), Gemtuzumab/ozogamicin (acute myeloid keulemia), ibritumomab/tiuxetan (non-Hodgkin lymphoma), panitumumab (colorectal cancer), pertuzumab (breast cancer), obinutuzumab (chronic lymphocytic leukemia), ofatumumab (chronic lymphocytic leukemia), opilimumab (melanoma), ramucirumab (gastric and gastro-oeasophageal cancers), rituximab (chronic lymphocytic leukemia and non-Hodgkin lymphoma), siltuximab (multicentric's Catsleman's disease), tositumomab (non-Hodgkin lymphoma), and trastuzumab (breast, gastric and gastro-oesophageal cancers); while examples of immunomodulatory antibodies include, without limitation, ipilimumab (melanoma) which blocks the CTLA4-dependent immune checkpoint, nivolumab (melanoma, lung cancer) and prembrolizubmab (melanoma) which both block the PDCD1-dependent immune checkpoint, as well as MPDL3280A, MEDI4736, MEDI0680, and MSB0010718C which all block the PD-L1-dependent immune checkpoint (Sharma and Allison, The future of immune checkpoint therapy. Science. 2015 Apr. 3;348 (6230): 56-61).

Other antibodies for cancer immunotherapy have been described in Buqué et al. (Buqué et al., Trial Watch: Immunomodulatory monoclonal antibodies for oncological indications. Oncoimmunology. 2015 Mar. 2;4 (4): e1008814. eCollection 2015 April), Redman et al. (Redman et al., Mechanisms of action of therapeutic antibodies for cancer. Mol Immunol. 2015 October;67 (2 Pt A): 28-45), and in Simpson and Caballero, Monoclonal antibodies for the therapy of cancer MC Proc. 2014; 8 (Suppl 4): 06 as well as on the antibody society website (list of therapeutic monoclonal antibodies approved or in review in the European Union or United States available on the weblink www.antibodysociety.org/news/approved_mabs.php).

Tumor cell lysates may also be combined with the antigenic peptide(s) according to the invention. Tumor cells are indeed capable of priming the immune response, by presenting endogenous peptides-MHC complexes, as well as via dendritic cells (DCs) of the host which can process and present the antigen delivered by said lysates. The range of antigens against which an immune response can be induced is thereby increased. Tumor cell lysates can be easily obtained by treating tumor cells with a heat shock and/or a chemical treatment, and can be autologous (i.e. isolated from the patient), or allogeneic (i.e. isolated from another subject).

Standard chemotherapeutic drugs and radiotherapeutic agents need not be further described herein as they have been extensively described in the literature, notably by Baskar et al. (Baskar et al., Cancer and radiation therapy: current advances and future directions. Int J Med Sci. 2012; 9 (3): 193-9), Paci et al. (Paci et al., Review of therapeutic drug monitoring of anticancer drugs part 1—cytotoxics. Eur J Cancer. 2014 August;50 (12): 2010-9) and Widmer et al. (Widmer et al., Review of therapeutic drug monitoring of anticancer drugs part two—targeted therapies. Eur J Cancer. 2014 Aug;50 (12): 2020-36). A list of such drugs and agents is also available on the cancer.gov website (www.cancer-.gov/about-cancer/treatment/drugs).

Preferably, the immune checkpoint modulator for combination with the antigenic peptide as defined herein is an activator or an inhibitor of one or more immune checkpoint molecule(s) selected from CD27, CD28, CD40, CD122, CD137, OX40, GITR, ICOS, A2AR, B7-H3, B7-H4, BTLA, CD40, CTLA-4, IDO, KIR, LAG3, PD-1, TIM-3, VISTA, CEACAM1, GARP, PS, CSF1R, CD94/ NKG2A, TDO, GITR, TNFR and/or FasR/DcR3; or an activator or an inhibitor of one or more ligands thereof.

More preferably, the immune checkpoint modulator is an activator of a (co-) stimulatory checkpoint molecule or an inhibitor of an inhibitory checkpoint molecule or a combination thereof. Accordingly, the immune checkpoint modulator is more preferably (i) an activator of CD27, CD28, CD40, CD122, CD137, OX40, GITR and/or ICOS or (ii) an inhibitor of A2AR, B7-H3, B7-H4, BTLA, CD40, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or FasR/DcR3.

Even more preferably, the immune checkpoint modulator is an inhibitor of an inhibitory checkpoint molecule (but preferably no inhibitor of a stimulatory checkpoint molecule). Accordingly, the immune checkpoint modulator is even more preferably an inhibitor of A2AR, B7-H3, B7-H4, BTLA, CTLA-4, IDO, KIR, LAG3, PD-1, PDL-1, PD-L2, TIM-3, VISTA, CEACAM1, GARP, PS, CSF1R, CD94/ NKG2A, TDO, TNFR and/or DcR3 or of a ligand thereof.

It is also preferred that the immune checkpoint modulator is an activator of a stimulatory or costimulatory checkpoint molecule (but preferably no activator of an inhibitory checkpoint molecule). Accordingly, the immune checkpoint modulator is more preferably an activator of CD27, CD28, CD40, CD122, CD137, OX40, GITR and/or ICOS or of a ligand thereof.

It is even more preferred that the immune checkpoint modulator is a modulator of the CD40 pathway, of the IDO pathway, of the LAG3 pathway, of the CTLA-4 pathway and/or of the PD-1 pathway. In particular, the immune checkpoint modulator is preferably a modulator of CD40, LAG3, CTLA-4, PD-L1, PD-L2, PD-1 and/or IDO, more preferably the immune checkpoint modulator is an inhibitor of CTLA-4, PD-L1, PD-L2, PD-1, LAG3, and/or IDO or an activator of CD40, even more preferably the immune checkpoint modulator is an inhibitor of CTLA-4, PD-L1, PD-1, LAG3 and/or IDO, even more preferably the immune checkpoint modulator is an inhibitor of LAG3, CTLA-4 and/or PD-1, and most preferably the immune checkpoint modulator is an inhibitor of CTLA-4 and/or PD-1.

Accordingly, the checkpoint modulator for combination with the antigenic peptide may be selected from known modulators of the CTLA-4 pathway or the PD-1 pathway. Preferably, the checkpoint modulator for combination with the antigenic peptide as defined herein may be selected from known modulators of the the CTLA-4 pathway or the PD-1 pathway. Particularly preferably, the immune checkpoint modulator is a PD-1 inhibitor. Preferred inhibitors of the CTLA-4 pathway and of the PD-1 pathway include the monoclonal antibodies YervoyR (Ipilimumab; Bristol Myers Squibb) and Tremelimumab (Pfizer/MedImmune) as well as Opdivo (Nivolumab; Bristol Myers Squibb), KeytrudaR (Pembrolizumab; Merck), Durvalumab (MedImmune/AstraZeneca), MEDI4736 (AstraZeneca; cf. WO 2011/066389 A1), MPDL3280A (Roche/Genentech; cf. U.S. Pat. No. 8,217,149 B2), Pidilizumab (CT-011; CureTech), MEDI0680 (AMP-514; AstraZeneca), MSB-0010718C (Merck), MIH1 (Affymetrix) and Lambrolizumab (e.g. disclosed as hPD109A and its humanized derivatives h409All, h409A16 and h409A17 in WO2008/156712; Hamid et al., 2013; N. Engl. J. Med. 369:134-144. More preferred checkpoint inhibitors include the CTLA-4 inhibitors Yervoy (Ipilimumab; Bristol Myers Squibb) and Tremelimumab (Pfizer/MedImmune) as well as the PD-1 inhibitors Opdivo (Nivolumab; Bristol Myers Squibb), Keytruda (Pembrolizumab; Merck), Pidilizumab (CT-011; CureTech), MEDI0680 (AMP-514; AstraZeneca), AMP-224 and Lambrolizumab (e.g. disclosed as hPD109A and its humanized derivatives h409All, h409A16 and h409A17 in WO2008/ 156712; Hamid O. et al., 2013; N. Engl. J. Med. 369:134-144. It is also preferred that the immune checkpoint modulator for combination with the antigenic peptide as defined herein is selected from the group consisting of Pembrolizumab, Ipilimumab, Nivolumab, MPDL3280A, MEDI4736, Tremelimumab, Avelumab, PDR001, LAG525, INCB24360, Varlilumab, Urelumab, AMP-224 and CM-24.

It is within the skill of ordinary person in the art to select the appropriate immune anti-cancer therapeutic agent for the purposes of the invention. For example, should one wish to prevent or treat melanoma, a lysate from melanoma cells and/or the antibody opilimumab can preferably be used, along with the corresponding antigenic peptide according to the present invention as described herein.

The anti-cancer therapeutic agent can also be administered in association with the antigenic peptide according to the present invention, the immunogenic compound according to the present invention, the nanoparticle according to the present invention, the cell according to the present invention, the nucleic acid according to the present invention, the host cell according to the present invention, or the immunogenic composition according to the present invention, either at about the same time or consecutively as described herein and in the same or distinct pharmaceutical forms.

Thus, in another aspect, the invention relates to a composition of the invention and at least one anti-cancer therapeutic agent as described above, as a combined preparation for a simultaneous, separate, or sequential administration. In other terms, the invention proposes a combined use of the composition the invention and least one anti-cancer therapeutic agent as described above, for a simultaneous, separate, or sequential administration.

Moreover, the present invention also provides the combination of (at least) two distinct antigenic peptides according to the present invention as described herein. In this context, the (at least) two distinct antigenic peptides may be in any form, e.g., "naked", comprised in immunogenic compounds, nanoparticles, (immunogenic) compositions or cells loaded therewith, or encoded by nucleic acids (e.g., vectors). Accordingly, the (at least) two distinct antigenic peptides may be comprised in (at least) two distinct components (to be combined). Accordingly, the two distinct components of the combination according to the present invention refer in particular to distinct antigenic peptides according to the present invention (which are comprised by the immunogenic compounds, the nanoparticles, encoded by the nucleic acids, etc.). Such two distinct components, in particular the two distinct antigenic peptides according to the invention (comprised in the two distinct components), relate preferably to the same type of cancer, for example to the same or distinct antigens associated with this cancer and/or to the same or distinct (reference) epitopes within an antigen associated with this cancer. More preferably, the two distinct components, in particular the two distinct antigenic peptides according to the invention (comprised in the two distinct components), relate to the same tumor (associated or specific) antigen. The two distinct components, in particular the two distinct antigenic peptides according to the invention (comprised in the two distinct components), may also relate to the same or distinct (reference) tumor (associated or specific) antigen(s).

Moreover, the antigenic peptide according to the present invention may also be combined with the corresponding (human) tumor antigen epitope (as described above regarding the peptide "families"). Thereby, selection of T-cell clones, which are very efficient against the tumor, is obtained/supported. In particular, the antigenic peptide according to the present invention and the corresponding (human) tumor antigen epitope may be co-administered. Such co-administration may be at about the same time (simultaneously) or consecutively, whereby in consecutive administration it is preferred that the antigenic peptide according to the present invention is administered first and the corresponding (human) tumor antigen epitope is administered thereafter. In particular, the antigenic peptide according to the present invention may be administered first, and the corresponding (human) tumor antigen epitope may be used as (re) boost. For example, the antigenic peptide according to SEQ ID NO:47 may be combined with the reference peptide according to SEQ ID NO: 120. In another example, the antigenic peptide according to SEQ ID NOs: 51, 52, 55, or 56 may be combined with the reference peptide according to SEQ ID NO: 122. In another example, the antigenic peptide according to SEQ ID NO:77 may be combined with the reference peptide according to SEQ ID NO: 128. In another example, the antigenic peptide according to SEQ ID NO:93 may be combined with the reference peptide according to SEQ ID NO:136. In another example, the antigenic peptide according to SEQ ID NO:28 may be combined with the reference peptide according to SEQ ID NO: 115. In another example, the antigenic peptide according to SEQ ID NOs: 101 or 102 may be combined with the reference peptide according to SEQ ID NO:141. In another example, the antigenic peptide according to SEQ ID NO:26 may be combined with the reference peptide according to SEQ ID NO:113.

Both peptides, which are to be combined, such as (a) the antigenic peptide according to the present invention and the corresponding (human) tumor antigen epitope or (b) two distinct antigenic peptides according to the present invention, may be administered
- in the same immunogenic compound according to the present invention or in distinct immunogenic compounds according to the present invention,
- (loaded) in the same nanoparticle according to the present invention or in distinct nanoparticles according to the present invention,
- (loaded) in the same cell according to the present invention or in distinct cells according to the present invention,
- (encoded by) the same nucleic acid according to the present invention or by distinct nucleic acids according to the present invention,
- (expressed by) the same host cell according to the present invention or by distinct host cells according to the present invention, or
- (comprised) in the same immunogenic composition according to the present invention or in distinct immunogenic composition according to the present invention.

For example, the present invention provides a combination of
 (i) an immunogenic compound according to the present invention comprising a first antigenic peptide according to the present invention, and
 (ii) an immunogenic compound according to the present invention comprising a second antigenic peptide according to the present invention for use in the prevention and/or treatment of a cancer.

For example, the present invention provides a combination of
 (i) a first antigenic peptide according to the present invention, and
 (ii) a second antigenic peptide according to the present invention for use in the prevention and/or treatment of a cancer.

For example, the present invention provides a combination of
 (i) a nanoparticle according to the present invention comprising a first antigenic peptide according to the present invention, and
 (ii) a nanoparticle according to the present invention comprising a second antigenic peptide according to the present invention for use in the prevention and/or treatment of a cancer.

For example, the present invention provides a combination of
 (i) a nucleic acid according to the present invention comprising a polynucleotide encoding a first antigenic peptide according to the present invention and
 (ii) a nucleic acid according to the present invention comprising a polynucleotide encoding a first antigenic peptide according to the present invention for use in the prevention and/or treatment of a cancer.

Preferably, both peptides, which are to be combined, such as (a) the antigenic peptide according to the present invention and the corresponding (human) tumor antigen epitope or (b) two distinct antigenic peptides according to the present invention, in particular components (i) and (ii), are administered at about the same time. In more general, it is preferred that the first (antigenic) peptide in any formulation (e.g., in the form of the immunogenic compound according to the present invention, the nanoparticle according to the present invention, the cell according to the present invention, the nucleic acid according to the present invention, the host cell according to the present invention, or the immunogenic composition according to the present invention; referred to herein as "the first (antigenic) peptide component") is administered at about the same time as the second (antigenic) peptide in any formulation (e.g., in the form of the immunogenic compound according to the present invention, the nanoparticle according to the present invention, the cell according to the present invention, the nucleic acid according to the present invention, the host cell according to the present invention, or the immunogenic composition according to the present invention; referred to herein as "the second (antigenic) peptide component"), wherein both (antigenic) peptides are preferably administered in the same form (i.e., in the same type of formulation, e.g., both as nanoparticles, both as immunogenic compositions, etc.).

"At about the same time", as used herein, means in particular simultaneous administration or that directly after administration of (i) the first (antigenic) peptide component, (ii) the second (antigenic) peptide component is administered or directly after administration of (ii) the second (antigenic) peptide component (i) the first (antigenic) peptide component is administered. The skilled person understands that "directly after" includes the time necessary to prepare the second administration—in particular the time necessary for exposing and disinfecting the location for the second administration as well as appropriate preparation of the "administration device" (e.g., syringe, pump, etc.). Simultaneous administration also includes if the periods of administration of (i) the first (antigenic) peptide component and of (ii) the second (antigenic) peptide component overlap or if, for example, one component is administered over a longer period of time, such as 30 min, 1 h, 2 h or even more, e.g. by infusion, and the other component is administered at some time during such a long period. Administration of (i) the first (antigenic) peptide component and of (ii) the second (antigenic) peptide component at about the same time is in particular preferred if different routes of administration and/or different administration sites are used.

It is also preferred that both peptides, which are to be combined, such as (a) the antigenic peptide according to the present invention and the corresponding (human) tumor antigen epitope or (b) two distinct antigenic peptides according to the present invention, in particular components (i) and (ii), are administered consecutively. In more general, it is preferred that the first (antigenic) peptide in any formulation (e.g., in the form of the immunogenic compound according to the present invention, the nanoparticle according to the present invention, the cell according to the present invention, the nucleic acid according to the present invention, the host cell according to the present invention, or the immunogenic composition according to the present invention; referred to herein as "the first (antigenic) peptide component") and the second (antigenic) peptide in any formulation (e.g., in the form of the immunogenic compound according to the present invention, the nanoparticle according to the present invention, the cell according to the present invention, the nucleic acid according to the present invention, the host cell according to the present invention, or the immunogenic composition according to the present invention; referred to herein as "the second (antigenic) peptide component") are administered consecutively, wherein both (antigenic) peptides are preferably administered in the same form (i.e., in the same type of formulation, e.g., both as nanoparticles, both as immunogenic compositions, etc.).

This means that (i) the first (antigenic) peptide component is administered before or after (ii) the second (antigenic) peptide component. In consecutive administration, the time between administration of the first component and administration of the second component is preferably no more than one week, more preferably no more than 3 days, even more preferably no more than 2 days and most preferably no more than 24 h. It is particularly preferred that (i) the first (antigenic) peptide component and (ii) the second (antigenic) peptide component are administered at the same day with the time between administration of the first component (the first or the second (antigenic) peptide) and administration of the second component (the other of the first or the second (antigenic) peptide) being preferably no more than 6 hours, more preferably no more than 3 hours, even more preferably no more than 2 hours and most preferably no more than 1 h.

Preferably, (i) the first (antigenic) peptide component and (ii) the second (antigenic) peptide component are administered via the same route of administration. In more general, it is preferred that the first (antigenic) peptide in any formulation (e.g., in the form of the immunogenic compound according to the present invention, the nanoparticle according to the present invention, the cell according to the present invention, the nucleic acid according to the present invention, the host cell according to the present invention, or the immunogenic composition according to the present invention; referred to herein as "the first (antigenic) peptide component") and the second (antigenic) peptide in any formulation (e.g., in the form of the immunogenic compound according to the present invention, the nanoparticle according to the present invention, the cell according to the present invention, the nucleic acid according to the present invention, the host cell according to the present invention, or the immunogenic composition according to the present invention; referred to herein as "the second (antigenic) peptide component") are administered via the same route of administration, wherein both (antigenic) peptides are preferably administered in the same form (i.e., in the same type of formulation, e.g., both as nanoparticles, both as immunogenic compositions, etc.).

It is also preferred that components (i) and (ii) are administered via distinct routes of administration. In more general, it is preferred that the first (antigenic) peptide in any formulation (e.g., in the form of the immunogenic compound according to the present invention, the nanoparticle according to the present invention, the cell according to the present invention, the nucleic acid according to the present invention, the host cell according to the present invention, or the immunogenic composition according to the present invention; referred to herein as "the first (antigenic) peptide component") and the second (antigenic) peptide component in any formulation (e.g., in the form of the immunogenic compound according to the present invention, the nanoparticle according to the present invention, the cell according to the present invention, the nucleic acid according to the present invention, the host cell according to the present invention, or the immunogenic composition according to the present invention; referred to herein as "the second (antigenic) peptide component") are administered via distinct routes of administration, wherein both (antigenic) peptides are preferably administered in the same form (i.e., in the same type of formulation, e.g., both as nanoparticles, both as immunogenic compositions, etc.).

Preferably, components (i) and (ii) are comprised in the same composition. In more general, it is preferred that the first (antigenic) peptide in any formulation (e.g., in the form of the immunogenic compound according to the present invention, the nanoparticle according to the present invention, the cell according to the present invention, the nucleic acid according to the present invention, or the host cell according to the present invention; referred to herein as "the first (antigenic) peptide component") and the second (antigenic) peptide in any formulation (e.g., in the form of the immunogenic compound according to the present invention, the nanoparticle according to the present invention, the cell according to the present invention, the nucleic acid according to the present invention, or the host cell according to the present invention; referred to herein as "the second (antigenic) peptide component") are comprised in the same composition, wherein both (antigenic) peptides are preferably administered in the same form (i.e., in the same type of formulation, e.g., both as nanoparticles, etc.).

It is also preferred that components (i) and (ii) are comprised in distinct compositions. In more general, it is preferred that the first (antigenic) peptide in any formulation (e.g., in the form of the immunogenic compound according to the present invention, the nanoparticle according to the present invention, the cell according to the present invention, the nucleic acid according to the present invention, or the host cell according to the present invention; referred to herein as "the first (antigenic) peptide component") and the second (antigenic) peptide in any formulation (e.g., in the form of the immunogenic compound according to the present invention, the nanoparticle according to the present invention, the cell according to the present invention, the nucleic acid according to the present invention, or the host cell according to the present invention; referred to herein as "the second (antigenic) peptide component") are comprised in distinct compositions, wherein both (antigenic) peptides are preferably administered in the same form (i.e., in the same type of formulation, e.g., both as nanoparticles, etc.).

Examples

Examples 1 and 2 are both linked to the general protocol described in FIG. 1.

EXAMPLE 1: Identification of a candidate antigenic peptide having superior affinity to the HLA-A*0201 allele This Example provides evidence that the antigenic peptide of sequence SEQ ID NO: 71 («FLPFGFILV» also referred herein as IL13RA2-B) has high affinity to the HLA-A*0201 allele, whereas the corresponding reference human peptide derived from IL13RA2 («WLPFGFILI», SEQ ID NO:123, also referred herein as IL13RA2-H) has low affinity.

A. Materials and Methods

A1. Measuring the Affinity of the Peptide to T2 Cell Line.

The experimental protocol is similar to the one that was validated for peptides presented by the HLA-A*0201 (Tourdot et al., A general strategy to enhance immunogenicity of low-affinity HLA-A2.1-associated peptides: implication in the identification of cryptic tumor epitopes. Eur J Immunol. 2000 December; 30 (12): 3411-21). Affinity measurement of the peptides is achieved with the human tumoral cell T2 which expresses the HLA-A*0201 molecule, but which is TAP1/2 negative and incapable of presenting endogenous peptides.

T2 cells ($2.10^5$ cells per well) are incubated with decreasing concentrations of peptides from 100 µM to 0.1 µM in a AIMV medium supplemented with 100 ng/µl of human β2m at 37° C. for 16 hours. Cells are then washed two times and marked with the anti-HLA-A2 antibody coupled to PE (clone BB7.2, BD Pharmagen).

The analysis is achieved by FACS (Guava Easy Cyte).

For each peptide concentration, the geometric mean of the labelling associated with the peptide of interest is subtracted from background noise and reported as a percentage of the geometric mean of the HLA-A*0202 labelling obtained for the reference peptide HIV pol 589-597 at a concentration of 100 µM. The relative affinity is then determined as follows:

relative affinity=concentration of each peptide inducing 20% of expression of HLA-A*0201/concentration of the reference peptide inducing 20% of expression of HLA-A*0201.

A2. Solubilisation of Peptides

Each peptide is solubilized by taking into account the amino acid composition. For peptides which do not include any Cystein, Methionin, or Tryptophane, the addition of DMSO is possible to up to 10% of the total volume. Other peptides are resuspended in water or PBS pH7.4.

B. Results

For T2 ATCC Cells: Mean fluorescence intensity for variable peptidic concentrations: Regarding the couple IL13RA2 peptides (IL13RA2-H and IL13RA2-B), it appears that the human peptide does not bind to the HLA-A*0201 contrarily to the candidate peptide IL13RA2-B, which binds strongly to HLA-A*0201:112.03 vs 18.64 at 100 M; 40.77 vs 11.61 at 10 µM; 12.18 vs 9.41 at 1 µM; 9.9 vs 7.46 at 0.1 µM. Also, IL13RA2-B at 4.4 µM induces 20% of expression of the HLA-A*0201 (vs 100 µM for IL13RA2-H).

Similar results were obtained from a second distinct T2 cell clone.

EXAMPLE 2: Vaccination on Mice with the Candidate Antigenic Peptide Induces Improved T Cell Responses in a ELISPOT-IFNγ Assay A. Materials and Methods A.1 Mouse Model The features of the model used are outlined in Table 2:

TABLE 2

Model features.

| | |
|---|---|
| Mouse Model | C57BL/6J B2m $^{tm1Unc}$IAb$^{-/-}$Tg(HLA-DRA HLA-DRB1*0301)$^{\#Gjh}$ Tg(HLA-A/H2-D/B2M)$^{1Bpe}$ |
| Acronym | β/A2/DR3 |
| Description | Immunocompetent, no mouse class I and class II MHC |
| Housing | SOPF conditions (ABSL3) |
| Number of mice | 24 adults (>8 weeks of age) |

A.2. Immunization Scheme.

Figure 2:
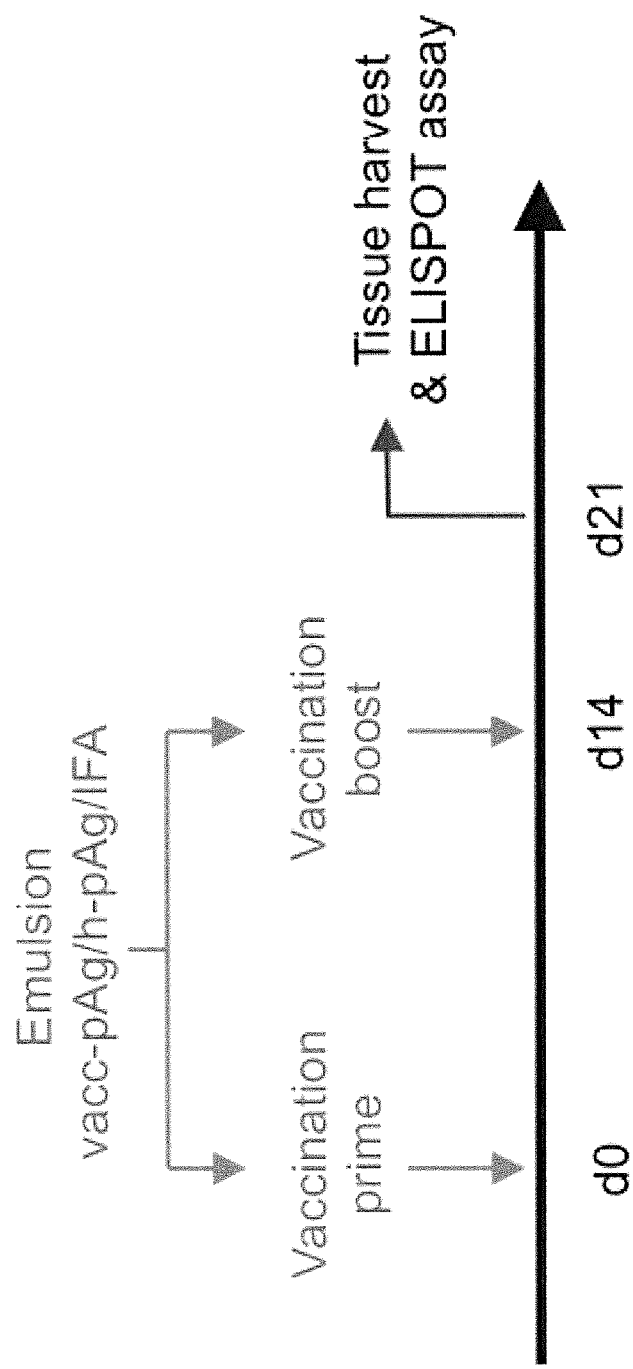
FIG. 2: Schematic view of the Immunization scheme. d: day.

The immunization scheme is shown in FIG. 2. Briefly, 14 β/A2/DR3 mice were assigned randomly (based on mouse sex and age) to two experimental groups, each immunized with a specific vaccination peptide (vacc-pAg) combined to a common helkper peptide (h-pAg) (as outlined in Table 3 below). The vacc-pAg were compared in couples (group 1 vs. group 2). Thereby, both native and optimized versions of a single peptide were compared in each wave.

TABLE 3

Experimental group composition. h-pAg: 'helper' peptide; vacc-pAg: vaccination peptide. The number of boost injections is indicated into brackets.

| Group | Peptide (vacc-pAg) | Helper (h-pAg) | Prime | Boost | Animal number |
|---|---|---|---|---|---|
| 1 | IL13RA2-B (100 µg) | HHD-DR3 (150 µg) | + | +(1X) | 6 |
| 2 | IL13RA2-H (100 µg) | HHD-DR3 (150 µg) | + | +(1X) | 6 |

The peptides were provided as follows:
couples of vacc-pAg: IL13RA2-H and IL13RA2-B; all produced and provided at a 4 mg/ml (4 mM) concentration;
h-pAg: HHD-DR3; provided lyophilized (50.6 mg; Eurogentec batch 1611166) and re-suspended in pure distilled water at a 10 mg/mL concentration;

The animals were immunized on day 0 (d0) with a prime injection, and on d14 with a boost injection. Each mouse was injected s.c. at tail base with 100 µL of an oil-based emulsion that contained:
100 µg of vacc-pAg (25 µL of 4 mg/mL stock per mouse);
150 µg of h-pAg (15 µL of 10 mg/mL stock per mouse);
10 µL of PBS to reach a total volume of 50 µL (per mouse);
Incomplete Freund's Adjuvant (IFA) added at 1:1 (v: v) ratio (50 µL per mouse).

A separate emulsion was prepared for each vacc-pAg, as follows: IFA reagent was added to the vacc-pAg/h-pAg/PBS mixture in a 15 mL tube and mixed on vortex for repeated cycles of 1 min until forming a thick emulsion.

A.3. Mouse Analysis

Seven days after the boost injection (i.e. on d21), the animals were euthanized and the spleen was harvested. Splenocytes were prepared by mechanical disruption of the organ followed by 70 μm-filtering and Ficoll density gradient purification.

The splenocytes were immediately used in an ELISPOT-IFNγ assay (Table 4). Experimental conditions were repeated in quadruplets, using 2*105 total splenocytes per well, and were cultured in presence of vacc-pAg (10 μM), Concanavalin A (ConA, 2.5 μg/mL) or medium-only to assess for their capacity to secrete IFNγ. The commercial ELISPOT-IFNγ kit (Diaclone Kit Mujrine IFNγ ELISpot) was used following the manufacturer's instructions, and the assay was performed after about 16h of incubation.

TABLE 4

Setup of the ELISPOT-IFNγ assay.

| Group | Stimulus | Wells | Animal | Total |
|---|---|---|---|---|
| 1 | IL13RA2-B (10 μM) | 4 | 6 | 24 |
|   | IL13RA2-H (10 μM) | 4 | 6 | 24 |
|   | ConA (2.5 μg/ml) | 4 | 6 | 24 |
|   | Medium | 4 | 6 | 24 |
| 2 | IL13RA2-B (10 μM) | 4 | 6 | 24 |
|   | IL13RA2-H (10 μM) | 4 | 6 | 24 |
|   | ConA (2.5 μg/ml) | 4 | 6 | 24 |
|   | Medium | 4 | 6 | 24 |

Spots were counted on a Grand ImmunoSpot® S6 Ultimate UV Image Analyzer interfaced to the ImmunoSpot 5.4 software (CTL-Europe). Data plotting and statistical analysis were performed with the Prism-5 software (GraphPad Software Inc.).

The cell suspensions were also analyzed by flow cytometry, for T cell counts normalization. The monoclonal antibody cocktail (data not shown) was applied on the purified leucocytes in presence of Fc-block reagents targeting murine (1:10 diluted 'anti-mCD16/CD32 CF11 clone'-internal source) Fc receptors. Incubations were performed in 96-well plates, in the dark and at 4° C. for 15-20 minutes. The cells were washed by centrifugation after staining to remove the excess of monoclonal antibody cocktail, and were re-suspended in PBS for data acquisition.

All data acquisitions were performed with an LSR-II Fortessa flow cytometer interfaced with the FACS-Diva software (BD Bioscience). The analysis of the data was performed using the FlowJo-9 software (TreeStar Inc.) using a gating strategy (not shown).

TABLE 5

FACS panel EXP-1.

| Target | Label | Clone | Provider | Dilution |
|---|---|---|---|---|
| mCD3εγ | FITC | 145-2C11 | Biolegend | 1/100 |
| mCD4 | PE | RM4-5 | Biolegend | 1/100 |
| mCD8α | APC | 53-6,7 | Biolegend | 1/100 |

B. Results

A total of 14 β/A2/DR3 mice were used for this experiment (see Table 6). At time of sacrifice, the spleen T cell population was analysed by flow cytometry, showing that the large majority belonged to the CD4+ T cell subset.

TABLE 6

Individual mouse features (groups 1 & 2).

| Mouse ID | Sex | Age[a] (wks) | Group (pAg) | T cells[b] (%) | T4[c] (%) | T8[c] (%) | Note[d] |
|---|---|---|---|---|---|---|---|
| 826 | M | 14 | 1 (IL13RA2-B) | 18.6 | 72.0 | 13.7 | P½ |
| 827 | M | 14 | 1 (IL13RA2-B) | 21.1 | 82.5 | 8.7 | P½ |
| 828 | M | 14 | 1 (IL13RA2-B) | 20.9 | 78.4 | 8.6 | P½ |
| 829 | F | 15 | 1 (IL13RA2-B) | 23.8 | 67.0 | 17.5 | P½ |
| 830 | F | 15 | 1 (IL13RA2-B) | 29.2 | 73.3 | 12.5 | P½ |
| 831 | F | 15 | 1 (IL13RA2-B) | N.A. | N.A. | N.A. | ID tag lost (excluded) |
| 17 | M | 9 | 1 (IL13RA2-B) | 8.3 | 83.7 | 10.4 | P5 |
| 832 | F | 15 | 2 (IL13RA2-H) | 28.3 | 83.4 | 5.7 | P½ |
| 833 | F | 15 | 2 (IL13RA2-H) | N.A. | N.A. | N.A. | ID tag lost (excluded) |
| 834 | F | 15 | 2 (IL13RA2-H) | 27.5 | 79.7 | 7.2 | P½ |
| 835 | M | 13 | 2 (IL13RA2-H) | 33.8 | 84.2 | 8.5 | P½ |
| 836 | M | 13 | 2 (IL13RA2-H) | 31.4 | 84.7 | 6.3 | P½ |
| 837 | M | 15 | 2 (IL13RA2-H) | 30.8 | 83.4 | 5.4 | P½ |
| 18 | M | 9 | 2 (IL13RA2-H) | 11.2 | 85.9 | 9.2 | P5 |

Each mouse is identified by a unique ear tag ID number.
[a]age at onset of the vaccination protocol (in weeks);
[b]percentage of T cells in total leukocytes;
[c]percentage of CD4+ or CD8+ T cells in total T cells;
[d]plate (P) number.

After plating and incubation with the appropriate stimuli, the IFNγ-producing cells were revealed and counted. The data were then normalized as a number of specific spots (the average counts obtained in the 'medium only' condition being subtracted) per 106 total T cells.

Figure 3:
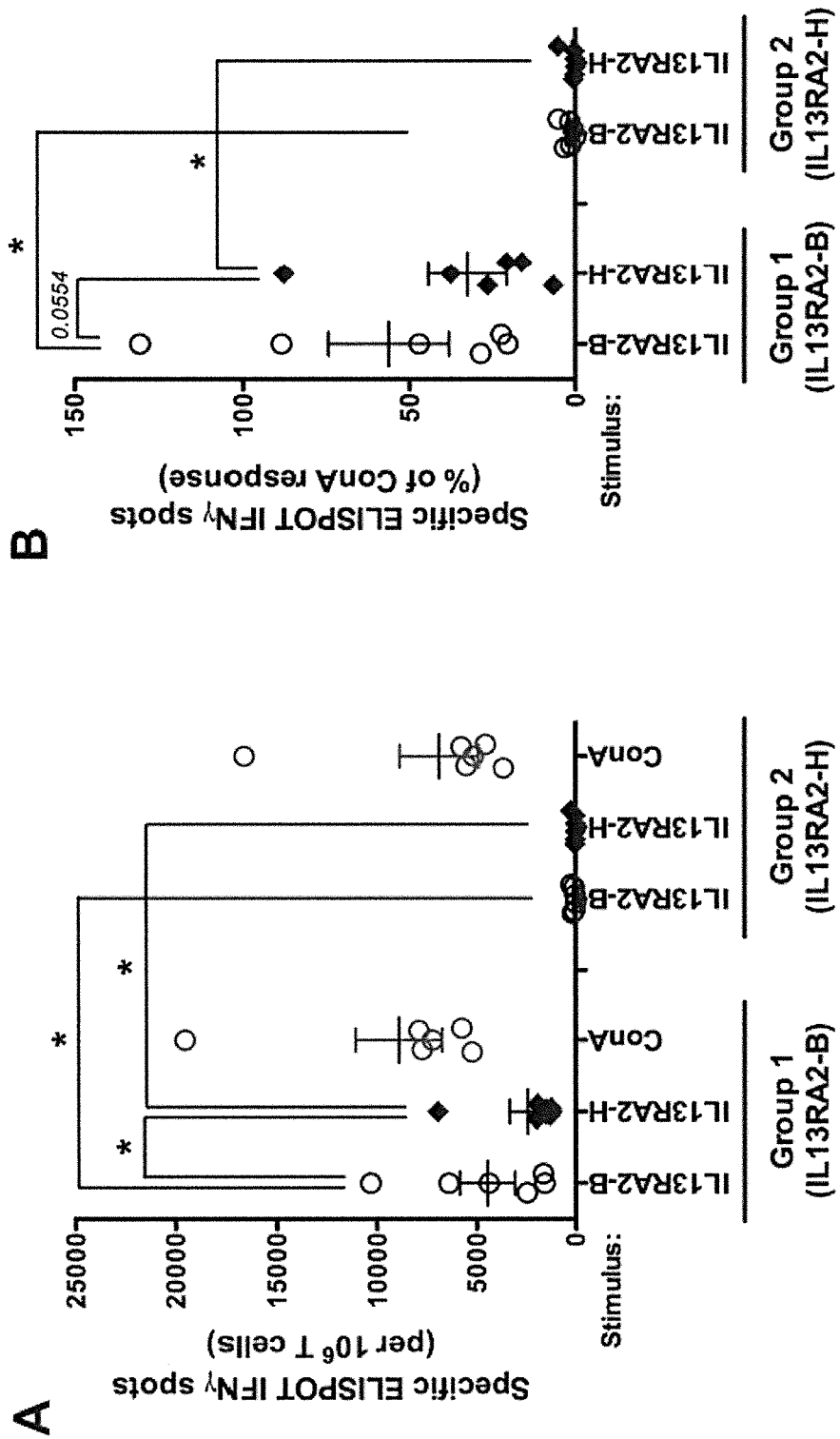
FIG. 3: ELISPOT-IFNγ results for group 1 (IL13RA2-B) and group 2 (IL13RA2-A). The peptide used for vaccination (in between brackets under each group) and the stimulus used in the ELISPOT culture (X-axis) are indicated on the graphs. (A) Number of specific ELISPOT-IFNγ spots (medium condition subtracted). Each dot represents the average value for one individual/mouse from the corresponding condition quadruplicate. (B) For each individual, the level of specific ELISPOT-IFNγ response is compared to the ConA stimulation (value: 100%). Statistical analysis: paired t-test for intra-group comparison and unpaired t-test for inter-group comparison; * p<0.05.

The individual average values (obtained from the quadruplicates) were next used to plot the group average values (see FIG. 3A). As the functional capacity of T cells might vary from individual to individual, the data were also expressed as the percentage of the ConA response per individual (see FIG. 3B).

Overall, vaccination with the IL13RA2-B pAg (candidate) peptide induced improved T cell responses in the ELISPOT-IFNγ assay, as compared to IL13RA2-H pA (reference human)-vaccinated animals (group 2). For group 1 (IL13RA2-B), ex vivo re-stimulation with the IL13RA2-B pAg promoted higher response than with the IL13RA2-H pAg. It was not the case for group 2 (IL13RA2-H). The percentage of ConA-induced response (mean+/−SEM) for each condition was as follows:

Group 1 (IL13RA2-B)/IL13RA2-B pAg: 56.3%+/−18.1
Group 1 (IL13RA2-B)/IL13RA2-H pAg: 32.3%+/−11.8.
Group 2 (IL13RA2-H)/IL13RA2-B pAg: 2.0%+/−0.8.
Group 2 (IL13RA2-H)/IL13RA2-H pAg: 1.1%+/−0.8

Accordingly, those results provide experimental evidence that tumor-antigen immunotherapy targeting IL13RA2 is able to improve T cell response in vivo and that the IL13RA2-B candidate peptide (SEQ ID NO:71) is particularly efficient for that purpose.

EXAMPLE 3: Identification of Further Candidate Antigenic Peptides Having Superior Affinity to the HLA-A*0201 Allele This Example provides evidence that the antigenic peptides of sequence SEQ ID NO: 47 («RLLEETDLV» also referred herein as ERBB2-1B); SEQ ID NO:51 («VMLGVVFGV» also referred herein as ERBB2-3β1); SEQ ID NO:52 («VLLGVVFGV» also referred herein as ERBB2-3β2); SEQ ID NO:55 («VMLGVVFGI» also referred herein as ERBB2-3β3); and SEQ ID NO:56 («ILLGVVFGI» also referred herein as ERBB2-3β4) have higher affinity to the HLA-A*0201 allele than the corresponding reference human peptides derived from ERBB2 («RLLQETELV», SEQ ID NO: 120, also referred herein as ERBB2-1H; («VVLGVVFGI», SEQ ID NO:122, also referred herein as ERBB2-3H).

A. Materials and Methods

A1. Measuring the Affinity of the Peptide to T2 Cell Line.

The experimental protocol is similar to the one that was validated for peptides presented by the HLA-A*0201 (Tourdot et al., A general strategy to enhance immunogenicity of low-affinity HLA-A2.1-associated peptides: implication in the identification of cryptic tumor epitopes. Eur J Immunol. 2000 December; 30 (12): 3411-21). Affinity measurement of the peptides is achieved with the human tumoral cell T2 which expresses the HLA-A*0201 molecule, but which is TAP1/2 negative and incapable of presenting endogenous peptides.

T2 cells ($2.10^5$ cells per well) are incubated with decreasing concentrations of peptides from 100 μM to 0.1 μM in a AIMV medium supplemented with 100 ng/μl of human β2m at 37° C. for 16 hours. Cells are then washed two times and marked with the anti-HLA-A2 antibody coupled to PE (clone BB7.2, BD Pharmagen).

The analysis is achieved by FACS (Guava Easy Cyte).

For each peptide concentration, the geometric mean of the labelling associated with the peptide of interest is subtracted from background noise and reported as a percentage of the geometric mean of the HLA-A*0202 labelling obtained for the reference peptide HIV pol 589-597 at a concentration of 100 μM. The relative affinity is then determined as follows:

relative affinity=concentration of each peptide inducing 20% of expression of HLA-A*0201/concentration of the reference peptide inducing 20% of expression of HLA-A*0201.

A2. Solubilisation of Peptides

Each peptide is solubilized by taking into account the amino acid composition. For peptides which do not include any Cystein, Methionin, or Tryptophane, the addition of DMSO is possible to up to 10% of the total volume. Other peptides are re-suspended in water or PBS pH7.4.

B. Results

Results are shown in Table 7:

| Peptide | SEQ ID NO. | 100 μM | 10 μM | 1 μM | 0.1 μM | Conc. inducing 20% of HLA-A2 expression [μM] | Relative affinity |
|---|---|---|---|---|---|---|---|
| ERBB2-1B | 47 | 296.97 | 26.39 | 2.86 | −1.18 | 9.5 | 0.26 |
| ERBB2-1H | 120 | 108.74 | 15.63 | −5.21 | −5.88 | 16.3 | 0.45 |
| ERBB2-3β1 | 51 | 122.18 | 26.72 | −12.94 | −15.97 | 9 | 0.25 |
| ERBB2-3β2 | 52 | 335.97 | 56.97 | 1.51 | −14.62 | 6.9 | 0.19 |
| ERBB2-3β3 | 55 | 178.66 | 16.64 | −10.59 | −16.3 | 12.5 | 0.35 |
| ERBB2-3β4 | 56 | 265.38 | 138.32 | 26.05 | −11.6 | 0.9 | 0.03 |
| ERBB2-3H | 122 | 196.47 | 11.93 | −24.03 | −12.61 | 16.3 | 0.45 |
| HIV pol 589-597 | | 100 | −3.03 | −5.38 | −9.24 | 36 | |

As shown in Table 7 (see, in particular, "relative affinity" calculated as described above), antigenic peptide ERBB2-1B shows higher affinity (lower value) than the corresponding human peptide ERBB2-1H. Moreover, antigenic peptides ERBB2-3β1, ERBB2-3β2, ERBB2-3β3 and ERBB2-3β4 show higher affinity (lower value) than the corresponding human peptide ERBB2-1B. Moreover, lower concentrations of the antigenic peptides ERBB2-1B, ERBB2-3β1, ERBB2-3β2, ERBB2-3β3 and ERBB2-3β4 (as compared to the human reference peptides) are required to induce 20% of expression of the HLA-A*0201.

Similar results were obtained from a second distinct T2 cell clone.

EXAMPLE 4: Identification of Further Candidate Antigenic Peptides Having Superior Affinity to the HLA-A*0201 Allele This Example provides evidence that the antigenic peptides of sequence SEQ ID NO: 77 («KLVEWLAML» also referred herein as MAGE C1B); SEQ ID NO:93 («SLPPDVQQV» also referred herein as MMP2-B); SEQ ID NO:28 («ITSDVPFSV» also referred herein as PMEL- B); SEQ ID NO:101 («MLAVFLPLV» also referred herein as STEAP-β1); and SEQ ID NO:102 («YLAVFLPIV» also referred herein as STEAP-β2) have higher affinity to the HLA-A*0201 allele than the corresponding reference human peptides derived from MAGE C1 («KVVE-FLAML», SEQ ID NO:128, also referred herein as MAGE C1H), MMP2 («GLPPDVQRV», SEQ ID NO:136, also referred herein as MMP2-H), PMEL («ITDQVPFSV», SEQ ID NO:115, also referred herein as PMEL-H), and STEAP («MIA VFLPIV», SEQ ID NO: 141, also referred herein as STEAP-H).

A. Materials and Methods

A1. Measuring the Affinity of the Peptide to T2 Cell Line.

The experimental protocol is similar to the one that was validated for peptides presented by the HLA-A*0201 (Tourdot et al., A general strategy to enhance immunogenicity of low-affinity HLA-A2.1-associated peptides: implication in the identification of cryptic tumor epitopes. Eur J Immunol. 2000 December; 30 (12): 3411-21). Affinity measurement of the peptides is achieved with the human tumoral cell T2 which expresses the HLA-A*0201 molecule, but which is TAP1/2 negative and incapable of presenting endogenous peptides.

T2 cells (2.10$^5$ cells per well) are incubated with decreasing concentrations of peptides from 100 μM to 0.1 μM in a AIMV medium supplemented with 100 ng/μl of human β2m at 37° C. for 16 hours. Cells are then washed two times and marked with the anti-HLA-A2 antibody coupled to PE (clone BB7.2, BD Pharmagen).

The analysis is achieved by FACS (Guava Easy Cyte).

For each peptide concentration, the geometric mean of the labelling associated with the peptide of interest is subtracted from background noise and reported as a percentage of the geometric mean of the HLA-A*0202 labelling obtained for the reference peptide HIV pol 589-597 at a concentration of 100 μM. The relative affinity is then determined as follows:

relative affinity=concentration of each peptide inducing 20% of expression of HLA-A*0201/concentration of the reference peptide inducing 20% of expression of HLA-A*0201.

A2. Solubilisation of Peptides

Each peptide is solubilized by taking into account the amino acid composition. For peptides which do not include any Cystein, Methionin, or Tryptophane, the addition of DMSO is possible to up to 10% of the total volume. Other peptides are re-suspended in water or PBS pH7.4.

B. Results

Results are shown in Table 8:

As shown in Table 8 (see, in particular, "relative affinity" calculated as described above), antigenic peptide MAGE C1B shows higher affinity (lower value) than the corresponding human peptide MAGE C1H. Moreover, antigenic peptide MMP2-B shows higher affinity (lower value) than the corresponding human peptide MMP2-H. Moreover, antigenic peptide PMEL-B shows higher affinity (lower value) than the corresponding human peptide PMEL-H. Moreover, antigenic peptides STEAP-β1 and STEAP-β2 show higher affinity (lower value) than the corresponding human peptide STEAP-H. Moreover, lower concentrations of the antigenic peptides MAGE CIB, MMP2-B, PMEL-B, STEAP-β1 and STEAP-β2 (as compared to their human reference peptides) are required to induce 20% of expression of the HLA-A*0201.

Similar results were obtained from a second distinct T2 cell clone.

EXAMPLE 5: Identification of Further Candidate Antigenic Peptides Having Superior Affinity to the HLA-A*0201 Allele This Example provides evidence that the antigenic peptide of sequence SEQ ID NO: 26 («TMNGKSSPV» also referred herein as ENAH-B) has high affinity to the HLA-A*0201 allele, whereas the corresponding reference human peptide derived from ENAH («TMNGSKSPV», SEQ ID NO:113, also referred herein as ENAH-H) has low affinity.

A. Materials and Methods

A1. Measuring the Affinity of the Peptide to T2 Cell Line.

The experimental protocol is similar to the one that was validated for peptides presented by the HLA-A*0201 (Tourdot et al., A general strategy to enhance immunogenicity of low-affinity HLA-A2.1-associated peptides: implication in the identification of cryptic tumor epitopes. Eur J Immunol. 2000 December; 30 (12): 3411-21). Affinity measurement of the peptides is achieved with the human tumoral cell T2 which expresses the HLA-A*0201 molecule, but which is TAP1/2 negative and incapable of presenting endogenous peptides.

T2 cells (2.10$^5$ cells per well) are incubated with decreasing concentrations of peptides from 100 μM to 0.1 μM in a AIMV medium supplemented with 100 ng/μl of human β2m at 37° C. for 16 hours. Cells are then washed two times and marked with the anti-HLA-A2 antibody coupled to PE (clone BB7.2, BD Pharmagen).

| Peptide | SEQ ID NO. | 100 μM | 10 μM | 1 μM | 0.1 μM | Conc. inducing 20% of HLA-A2 expression [μM] | Relative affinity |
|---|---|---|---|---|---|---|---|
| MAGE C1B | 77 | 108.8 | 21.4 | 3.97 | 2.45 | 30.91 | 0.31 |
| MAGE C1H | 128 | 32.27 | 7.84 | 7.12 | 5.77 | 60.07 | 1.94 |
| MMP2-B | 93 | 131.08 | 95.96 | 24.64 | 4.69 | 0.88 | 0.03 |
| MMP2-H | 136 | 154.17 | 66.31 | 17.81 | 5.41 | 1.76 | 0.06 |
| PMEL-B | 28 | 74.85 | 7.93 | 3.62 | 4.69 | 18.24 | 0.59 |
| PMEL-H | 115 | 112.58 | 9.09 | 5.32 | 1.01 | 23.94 | 0.77 |
| STEAP-B1 | 101 | 131.62 | 45.12 | 8.92 | 6.67 | 5 | 0.16 |
| STEAP-B2 | 102 | 97.93 | 27.69 | 4.87 | −0.34 | 8.22 | 0.27 |
| STEAP-H | 141 | 101.98 | 14.93 | −4.47 | 0.11 | 33.45 | 1.08 |
| HIV pol 589-597 | | 100 | 3.8 | −2.54 | 2.58 | 30.91 | |

The analysis is achieved by FACS (Guava Easy Cyte).

For each peptide concentration, the geometric mean of the labelling associated with the peptide of interest is subtracted from background noise and reported as a percentage of the geometric mean of the HLA-A*0202 labelling obtained for the reference peptide HIV pol 589-597 at a concentration of 100 μM. The relative affinity is then determined as follows:

relative affinity=concentration of each peptide inducing 20% of expression of HLA-A*0201/concentration of the reference peptide inducing 20% of expression of HLA-A*0201.

A2. Solubilisation of Peptides

Each peptide is solubilized by taking into account the amino acid composition. For peptides which do not include any Cystein, Methionin, or Tryptophane, the addition of DMSO is possible to up to 10% of the total volume. Other peptides are re-suspended in water or PBS pH7.4.

B. Results

Results are shown in Table 9:

| Peptide | SEQ ID NO. | 100 μM | 10 μM | 1 μM | 0.1 μM | Conc. inducing 20% of HLA-A2 expression [μM] | Relative affinity |
|---|---|---|---|---|---|---|---|
| ENAH-1B | 26 | 100.24 | 2.93 | 14.18 | 12.71 | 33.45 | 1.26 |
| ENAH-1H | 113 | 18.58 | 19.07 | −2.93 | 8.31 | ND | ND |
| HIV pol 589-597 | | 100 | 8.8 | 4.65 | 5.62 | 26.48 | |

As shown in Table 9 (see, in particular, "relative affinity" calculated as described above), antigenic peptide ENAH-B shows higher affinity (lower value) than the corresponding human peptide ENAH-H. In particular, it appears that the human peptide ENAH-H does not bind to the HLA-A*0201 (ND . . . not determined).

Moreover, lower concentrations of the antigenic peptide ENAH-B (as compared to the human reference peptide ENAH-H) were required to induce 20% of expression of the HLA-A*0201.

Similar results were obtained from a second distinct T2 cell clone.

---

The invention claimed is:

1. An immunogenic composition comprising:
 (i) an immunogenic compound comprising or consisting of an antigenic peptide off formula (I):

PepNt-CORE-PepCt(I), wherein:
  "PepNt" consists of a polypeptide having an amino acid length varying from 0 to 50 amino acid residues and located at the N-terminal end of the polypeptide off formula (I);
  "CORE" consists of a polypeptide consisting of [,] an amino acid sequence selected from the group consisting of SEQ ID NOs: 51, SEQ ID NOs: 53 to 67, and SEQ ID NOs: 69 to 70; and
  "PepCt" consists of a polypeptide having an amino acid length varying from 0 to 50 amino acid residues and located at the C-terminal end of the polypeptide of formula (I)
 (ii) an antigenic peptide as defined in (i),
 (iii) a nanoparticle loaded with at least one immunogenic compound of (i) or at least one antigenic peptide of (ii),
 (iv) a cell loaded with at least one immunogenic compound of (i) or at least one antigenic peptide of (ii),
 (v) a nucleic acid comprising a polynucleotide encoding (a) the immunogenic compound of (i), wherein the immunogenic compound is a peptide or a protein, or (b) the antigenic peptide of (ii), or
 (vi) a host cell comprising the nucleic acid of (v);

wherein the immunogenic composition comprises one or more pharmaceutically acceptable excipients and one or more immunostimulatory agents comprising antigen-presenting cells.

2. The immunogenic composition according to claim 1, wherein the antigen-presenting cells comprise or consist of dendritic cells.

3. The immunogenic composition according to claim 1, wherein the composition comprises:
   (i) two distinct immunogenic compounds;
   (ii) two distinct antigenic peptides;
   (iii) two distinct nanoparticles; or
   (iv) two distinct nucleic acids.

4. The immunogenic composition according to claim 1, wherein the antigenic peptide is linked to a carrier protein.

5. An immunogenic composition comprising:
   (i) an immunogenic compound comprising or consisting of an antigenic peptide off formula (I):

PepNt-CORE-PepCt(I), wherein:
      "PepNt" consists of a polypeptide having an amino acid length varying from 0 to 50 amino acid residues and located at the N-terminal end of the polypeptide off formula (I);
      "CORE" consists of a polypeptide consisting of an amino acid sequence selected from the group consisting of SEQ ID NOS: 51, SEQ ID NOs: 53 to 67, and SEQ ID NOs: 69 to 70; and
      "PepCt" consists of a polypeptide having an amino acid length varying from 0 to 50 amino acid residues and located at the C-terminal end of the polypeptide of formula (I)
   (ii) an antigenic peptide as defined in (i),
   (iii) a nanoparticle loaded with at least one immunogenic compound of (i) or at least one antigenic peptide of (ii),
   (iv) a cell loaded with at least one immunogenic compound of (i) or at least one antigenic peptide of (ii),
   (v) a nucleic acid comprising a polynucleotide encoding (a) the immunogenic compound of (i), wherein the immunogenic compound is a peptide or a protein, or (b) the antigenic peptide of (ii), or
   (vi) a host cell comprising the nucleic acid of (v);
wherein the immunogenic composition comprises one or more pharmaceutically acceptable excipient(s) and one or more immuno-adjuvant(s) selected from the group consisting of mineral compounds, oil-based emulsions, immunostimulatory complexes (ISCOMs), Interleukins, Tumor necrosis factors (TNFs), Interferons (IFNs), imiquimod, resiquimod, MPL, exosomes, tetanus helper peptide, keyhole limpet hemocyanin peptide, PADRE peptide, HHD-DR3 peptide, specific tumor derived helper peptides, polyinosinic: polycytidylic acid (poly I:C) and/or its derivative poly-ICLC, and any combination thereof.

6. The immunogenic composition according to claim 5, wherein the antigenic peptide is linked to a carrier protein.

7. An antigen presenting cell loaded with:
   (i) an immunogenic compound comprising or consisting of an antigenic peptide having an amino acid sequence selected from the group consisting SEQ ID NO: 51, SEQ ID NOs: 53 to 67, and SEQ ID NOs: 69 to 70;
   (ii) an antigenic peptide as defined in (i);
   (iii) an immunogenic compound comprising or consisting of an antigenic peptide off formula (I):

PepNt-CORE-PepCt(1), wherein:
      "PepNt" consists of a polypeptide having an amino acid length varying from 0 to 50 amino acid residues and located at the N-terminal end of the polypeptide off formula (I);
      "CORE" consists of a polypeptide consisting of an amino acid sequence selected from the group consisting of SEQ ID NOs: 51, SEQ ID NOs: 53 to 67, and SEQ ID NOs: 69 to 70; and
      "PepCt" consists of a polypeptide having an amino acid length varying from 0 to 50 amino acid residues and located at the C-terminal end of the polypeptide of formula (I); or
   (iv) an antigenic peptide as defined in (iii).

8. The antigen presenting cell according to claim 7, wherein the antigenic peptide is linked to a carrier protein.

9. A method for treating a cancer or initiating, enhancing or prolonging an anti-tumor response in a subject in need thereof, the method comprising:
   (A) administering to the subject:
      (i) an immunogenic compound comprising or consisting of an antigenic peptide off formula (I):

PepNt-CORE-PepCt(I), wherein:
         "PepNt" consists of a polypeptide having an amino acid length varying from 0 to 50 amino acid residues and located at the N-terminal end of the polypeptide off formula (I);
         "CORE" consists of a polypeptide consisting of an amino acid sequence selected from the group consisting of SEQ ID NOs: 51, SEQ ID NOs: 53 to 67, and SEQ ID NOs: 69 to 70; and
         "PepCt" consists of a polypeptide having an amino acid length varying from 0 to 50 amino acid residues and located at the C-terminal end of the polypeptide of formula (I),
      (ii) an antigenic peptide as defined in (i),
      (iii) a nanoparticle loaded with at least one immunogenic compound of (i) or at least one antigenic peptide of (ii),
      (iv) a cell loaded with at least one immunogenic compound of (i) or at least one antigenic peptide of (ii),
      (v) a nucleic acid comprising a polynucleotide encoding (a) the immunogenic compound of (i), wherein the immunogenic compound is a peptide or a protein, or (b) the antigenic peptide of (ii),
      (vi) a host cell comprising the nucleic acid of (v),
      (vii) an immunogenic composition comprising (i), (ii), (iv), (v), or (vi), or
      (ix) an antigen presenting cell according to any one of claims 7 and 8,
      and one or more pharmaceutically acceptable excipients; or
   (B) administering to the subject an immunogenic composition according to any one of claims 1, 2, 3, 4, 5, and 6;
      one or more immuno-adjuvants, and one or more immunostimulatory agents selected from the group consisting of antigen-presenting cells.

10. The method according to claim 9, wherein the cancer is selected from the group consisting of melanoma, colorectal cancer, and clear cell renal cell carcinoma.

11. The method according to claim 9, wherein at least two distinct immunogenic compounds, at least two distinct antigenic peptides, at least two distinct nanoparticles, or at least two distinct nucleic acids are administered to the subject.

12. The method according to claim 11, wherein the at least two distinct immunogenic compounds, at least two distinct antigenic peptides, at least two distinct nanoparticles, or at least two distinct nucleic acids are comprised in distinct compositions.

13. The method according to claim 11, wherein the at least two distinct immunogenic compounds, at least two distinct antigenic peptides, at least two distinct nanoparticles, or at least two distinct nucleic acids are comprised in the same composition.

14. The method according to claim 11, wherein the at least two distinct immunogenic compounds, at least two distinct antigenic peptides, at least two distinct nanoparticles, or at least two distinct nucleic acids are administered via distinct routes of administration.

15. The method according to claim 11, wherein the at least two distinct immunogenic compounds, at least two distinct antigenic peptides, at least two distinct nanoparticles, or at least two distinct nucleic acids are administered via the same route of administration.

16. The method according to claim 11, wherein the at least two distinct immunogenic compounds, at least two distinct antigenic peptides, at least two distinct nanoparticles, or at least two distinct nucleic acids are administered consecutively.

17. The method according to claim 11, wherein the at least two distinct immunogenic compounds, at least two distinct antigenic peptides, at least two distinct nanoparticles, or at least two distinct nucleic acids are administered at about the same time.

18. A kit comprising:
   (i) an immunogenic composition according to any one of claims 1, 2, 3, 4, 5, and 6, or
      (ii) an antigen presenting cell according to claim 7 or 8; and one or more pharmaceutically acceptable excipients.

19. The kit according to claim 18, further comprising a package insert or instruction leaflet with directions to treat a cancer.

* * * * *